United States Patent
Landstrom et al.

(10) Patent No.: US 9,296,818 B2
(45) Date of Patent: Mar. 29, 2016

(54) CLEAVAGE INHIBITORS OF TRANSFORMING GROWTH FACTOR BETA TYPE I RECEPTOR AND USES THEREOF IN CANCER THERAPY

(76) Inventors: Marene Inga-Britt Landstrom, Alunda (SE); Yabing Mu, Uppsala (SE); Reshma Sundar, Umeå (SE); Noopur Thakur, Uppsala (SE); Shyam Kumar Gudey, Uppsala (SE); Maria Ekman, Uppsala (SE); Carl-Henrik Heldin, Uppsala (DE)

( * ) Notice: Subject to any disclaimer, the term of this patent is extended or adjusted under 35 U.S.C. 154(b) by 101 days.

(21) Appl. No.: 14/004,490

(22) PCT Filed: Mar. 13, 2012

(86) PCT No.: PCT/US2012/028903
§ 371 (c)(1),
(2), (4) Date: Jan. 30, 2014

(87) PCT Pub. No.: WO2012/125623
PCT Pub. Date: Sep. 20, 2012

(65) Prior Publication Data
US 2014/0140998 A1    May 22, 2014
US 2014/0377268 A9    Dec. 25, 2014

Related U.S. Application Data

(60) Provisional application No. 61/452,549, filed on Mar. 14, 2011.

(51) Int. Cl.
| | | |
|---|---|---|
| *A61K 39/395* | (2006.01) | |
| *C07K 16/28* | (2006.01) | |
| *A61K 31/00* | (2006.01) | |
| *C07K 14/71* | (2006.01) | |
| *G01N 33/574* | (2006.01) | |
| *A61K 31/4709* | (2006.01) | |
| *A61K 31/65* | (2006.01) | |
| *C12Q 1/68* | (2006.01) | |

(52) U.S. Cl.
CPC ............. *C07K 16/2863* (2013.01); *A61K 31/00* (2013.01); *A61K 31/4709* (2013.01); *A61K 31/65* (2013.01); *A61K 39/395* (2013.01); *C07K 14/71* (2013.01); *C12Q 1/686* (2013.01); *G01N 33/57496* (2013.01); *C07K 2317/34* (2013.01); *C07K 2317/70* (2013.01); *G01N 2333/495* (2013.01)

(58) Field of Classification Search
CPC .......... C07K 16/2863; C07K 2317/34; C07K 2317/70; A61K 39/00; A61K 39/3955; A61K 2039/505; A61L 39/395
See application file for complete search history.

(56) References Cited

PUBLICATIONS

Lu et al., Oncol Rep. May 2011;25(5):1329-1335.*
Shapira et al. J Biol Chem. Aug. 3, 2012;287(32):26876-26889.*
[No Author Listed] Santa Cruz Biotechnology, Inc., TGFβ RI (H-100): sc-9048. Retrieved from http://datasheets.scbt.com/sc-9048.pdf Apr. 24, 2014.
Liu et al., TACE-mediated ectodomain shedding of the type I TGF-beta receptor downregulates TGF-beta signaling. Mol Cell. Jul. 10, 2009;35(1):26-36. doi: 10.1016/j.molcel.2009.06.018.
Moyano et al., Autocrine transforming growth factor-{beta}1 activation mediated by integrin {alpha}V{beta}3 regulates transcriptional expression of laminin-332 in Madin-Darby canine kidney epithelial cells. Mol Biol Cell. Nov. 1, 2010;21(21):3654-68. doi: 10.1091/mbc.E10-06-0523. Epub Sep. 15, 2010.
Mu et al., TRAF6 ubiquitinates TGFβ type I receptor to promote its cleavage and nuclear translocation in cancer. Nat Commun. 2011;2:330. doi: 10.1038/ncomms1332.

* cited by examiner

*Primary Examiner* — Daniel C Gamett
(74) *Attorney, Agent, or Firm* — Wolf, Greenfield & Sacks, P.C.

(57) ABSTRACT

Disclosed herein are methods to inhibit cleavage of a type I receptor of transforming growth factor beta (TβRI) and reduce cancer cell invasiveness/metastasis, and agents and pharmaceutical compositions for use in these methods. Also disclosed herein are methods for identifying agents that inhibit cleavage of TβRI and methods for diagnosing and/or prognosing cancer based on nuclear localization of a intracellular domain of TβRI, which is a product of TβRI cleavage.

10 Claims, 33 Drawing Sheets a.

b.

SEQUENCE LISTING

```
<160> NUMBER OF SEQ ID NOS: 21

<210> SEQ ID NO 1
<211> LENGTH: 503
<212> TYPE: PRT
<213> ORGANISM: H. sapiens

<400> SEQUENCE: 1
```

```
Met Glu Ala Ala Val Ala Ala Pro Arg Pro Arg Leu Leu Leu Val
 1               5                  10                  15

Leu Ala Ala Ala Ala Ala Ala Ala Leu Leu Pro Gly Ala Thr
            20                  25                  30

Ala Leu Gln Cys Phe Cys His Leu Cys Thr Lys Asp Asn Phe Thr Cys
        35                  40                  45

Val Thr Asp Gly Leu Cys Phe Val Ser Val Thr Glu Thr Thr Asp Lys
50                  55                  60

Val Ile His Asn Ser Met Cys Ile Ala Glu Ile Asp Leu Ile Pro Arg
65                  70                  75                  80

Asp Arg Pro Phe Val Cys Ala Pro Ser Ser Lys Thr Gly Ser Val Thr
                85                  90                  95

Thr Thr Tyr Cys Cys Asn Gln Asp His Cys Asn Lys Ile Glu Leu Pro
            100                 105                 110

Thr Thr Val Lys Ser Ser Pro Gly Leu Gly Pro Val Glu Leu Ala Ala
        115                 120                 125

Val Ile Ala Gly Pro Val Cys Phe Val Cys Ile Ser Leu Met Leu Met
        130                 135                 140

Val Tyr Ile Cys His Asn Arg Thr Val Ile His His Arg Val Pro Asn
145                 150                 155                 160

Glu Glu Asp Pro Ser Leu Asp Arg Pro Phe Ile Ser Glu Gly Thr Thr
                165                 170                 175

Leu Lys Asp Leu Ile Tyr Asp Met Thr Thr Ser Gly Ser Gly Ser Gly
            180                 185                 190

Leu Pro Leu Leu Val Gln Arg Thr Ile Ala Arg Thr Ile Val Leu Gln
        195                 200                 205

Glu Ser Ile Gly Lys Gly Arg Phe Gly Glu Val Trp Arg Gly Lys Trp
        210                 215                 220

Arg Gly Glu Glu Val Ala Val Lys Ile Phe Ser Ser Arg Glu Glu Arg
225                 230                 235                 240

Ser Trp Phe Arg Glu Ala Glu Ile Tyr Gln Thr Val Met Leu Arg His
                245                 250                 255

Glu Asn Ile Leu Gly Phe Ile Ala Ala Asp Asn Lys Asp Asn Gly Thr
            260                 265                 270

Trp Thr Gln Leu Trp Leu Val Ser Asp Tyr His Glu His Gly Ser Leu
        275                 280                 285

Phe Asp Tyr Leu Asn Arg Tyr Thr Val Thr Val Glu Gly Met Ile Lys
        290                 295                 300

Leu Ala Leu Ser Thr Ala Ser Gly Leu Ala His Leu His Met Glu Ile
305                 310                 315                 320

Val Gly Thr Gln Gly Lys Pro Ala Ile Ala His Arg Asp Leu Lys Ser
                325                 330                 335

Lys Asn Ile Leu Val Lys Lys Asn Gly Thr Cys Cys Ile Ala Asp Leu
            340                 345                 350

Gly Leu Ala Val Arg His Asp Ser Ala Thr Asp Thr Ile Asp Ile Ala
        355                 360                 365

Pro Asn His Arg Val Gly Thr Lys Arg Tyr Met Ala Pro Glu Val Leu
        370                 375                 380

Asp Asp Ser Ile Asn Met Lys His Phe Glu Ser Phe Lys Arg Ala Asp
385                 390                 395                 400

Ile Tyr Ala Met Gly Leu Val Phe Trp Glu Ile Ala Arg Arg Cys Ser
                405                 410                 415

Ile Gly Gly Ile His Glu Asp Tyr Gln Leu Pro Tyr Tyr Asp Leu Val
```

```
                    420                 425                 430
Pro Ser Asp Pro Ser Val Glu Glu Met Arg Lys Val Val Cys Glu Gln
            435                 440                 445

Lys Leu Arg Pro Asn Ile Pro Asn Arg Trp Gln Ser Cys Glu Ala Leu
        450                 455                 460

Arg Val Met Ala Lys Ile Met Arg Glu Cys Trp Tyr Ala Asn Gly Ala
465                 470                 475                 480

Ala Arg Leu Thr Ala Leu Arg Ile Lys Lys Thr Leu Ser Gln Leu Ser
            485                 490                 495

Gln Gln Glu Gly Ile Lys Met
            500

<210> SEQ ID NO 2
<211> LENGTH: 21
<212> TYPE: RNA
<213> ORGANISM: Artificial Sequence
<220> FEATURE:
<223> OTHER INFORMATION: siRNA targeting ALK5

<400> SEQUENCE: 2
aacauauugc ugcaaccagg a                                              21

<210> SEQ ID NO 3
<211> LENGTH: 21
<212> TYPE: RNA
<213> ORGANISM: Artificial Sequence
<220> FEATURE:
<223> OTHER INFORMATION: Non-specific control siRNA

<400> SEQUENCE: 3
aacagucgcg uuugcgacug g                                              21

<210> SEQ ID NO 4
<211> LENGTH: 20
<212> TYPE: DNA
<213> ORGANISM: Artificial Sequence
<220> FEATURE:
<223> OTHER INFORMATION: TbetaRI forward primer

<400> SEQUENCE: 4
tgttggtacc caaggaaagc                                                20

<210> SEQ ID NO 5
<211> LENGTH: 20
<212> TYPE: DNA
<213> ORGANISM: Artificial Sequence
<220> FEATURE:
<223> OTHER INFORMATION: TbetaRI reverse primer

<400> SEQUENCE: 5
cactctgtgg tttggagcaa                                                20

<210> SEQ ID NO 6
<211> LENGTH: 20
<212> TYPE: DNA
<213> ORGANISM: Artificial Sequence
<220> FEATURE:
<223> OTHER INFORMATION: p300 forward primer

<400> SEQUENCE: 6
gggactaacc aatggtggtg                                                20

<210> SEQ ID NO 7
```

```
<211> LENGTH: 20
<212> TYPE: DNA
<213> ORGANISM: Artificial Sequence
<220> FEATURE:
<223> OTHER INFORMATION: p300 reverse primer

<400> SEQUENCE: 7
gtcattgggc ttttgaccat                                                 20

<210> SEQ ID NO 8
<211> LENGTH: 20
<212> TYPE: DNA
<213> ORGANISM: Artificial Sequence
<220> FEATURE:
<223> OTHER INFORMATION: SNAIL 1 forward primer

<400> SEQUENCE: 8
gagcatacag ccccatcact                                                 20

<210> SEQ ID NO 9
<211> LENGTH: 20
<212> TYPE: DNA
<213> ORGANISM: Artificial Sequence
<220> FEATURE:
<223> OTHER INFORMATION: SNAIL 1 reverse primer

<400> SEQUENCE: 9
gggtctgaaa gcttggactg                                                 20

<210> SEQ ID NO 10
<211> LENGTH: 20
<212> TYPE: DNA
<213> ORGANISM: Artificial Sequence
<220> FEATURE:
<223> OTHER INFORMATION: Smad7 forward primer

<400> SEQUENCE: 10
tcctgctgtg caaagtgttc                                                 20

<210> SEQ ID NO 11
<211> LENGTH: 20
<212> TYPE: DNA
<213> ORGANISM: Artificial Sequence
<220> FEATURE:
<223> OTHER INFORMATION: Smad7 reverse primer

<400> SEQUENCE: 11
tctggacagt ctgcagttgg                                                 20

<210> SEQ ID NO 12
<211> LENGTH: 20
<212> TYPE: DNA
<213> ORGANISM: Artificial Sequence
<220> FEATURE:
<223> OTHER INFORMATION: MMP-2 forward primer

<400> SEQUENCE: 12
aggccgacat catggtactc                                                 20

<210> SEQ ID NO 13
<211> LENGTH: 20
<212> TYPE: DNA
<213> ORGANISM: Artificial Sequence
<220> FEATURE:
<223> OTHER INFORMATION: MMP-2 reverse primer

<400> SEQUENCE: 13
```

```
ggtcagtgct ggagaaggtc                                                        20
```

<210> SEQ ID NO 14
<211> LENGTH: 20
<212> TYPE: DNA
<213> ORGANISM: Artificial Sequence
<220> FEATURE:
<223> OTHER INFORMATION: PAI 1 forward primer

<400> SEQUENCE: 14

```
ctctctctgc cctcaccaac                                                        20
```

<210> SEQ ID NO 15
<211> LENGTH: 20
<212> TYPE: DNA
<213> ORGANISM: Artificial Sequence
<220> FEATURE:
<223> OTHER INFORMATION: PAI 1 reverse primer

<400> SEQUENCE: 15

```
gtggagaggc tcttggtctg                                                        20
```

<210> SEQ ID NO 16
<211> LENGTH: 20
<212> TYPE: DNA
<213> ORGANISM: Artificial Sequence
<220> FEATURE:
<223> OTHER INFORMATION: SNAIL1 forward primer

<400> SEQUENCE: 16

```
ggactcaggg agactcatgg                                                        20
```

<210> SEQ ID NO 17
<211> LENGTH: 20
<212> TYPE: DNA
<213> ORGANISM: Artificial Sequence
<220> FEATURE:
<223> OTHER INFORMATION: SNAIL1 reverse primer

<400> SEQUENCE: 17

```
gggtctacgg aaacctctgg                                                        20
```

<210> SEQ ID NO 18
<211> LENGTH: 24
<212> TYPE: PRT
<213> ORGANISM: H. sapiens

<400> SEQUENCE: 18

```
Leu Gly Pro Val Glu Leu Ala Ala Val Ile Ala Gly Pro Val Cys Phe
1               5                   10                  15

Val Cys Ile Ser Leu Met Leu Met
            20
```

<210> SEQ ID NO 19
<211> LENGTH: 24
<212> TYPE: PRT
<213> ORGANISM: R. norvegicus

<400> SEQUENCE: 19

```
Leu Gly Pro Val Glu Leu Ala Ala Val Ile Ala Gly Pro Val Cys Phe
1               5                   10                  15

Val Cys Ile Ser Leu Met Leu Met
            20
```

```
<210> SEQ ID NO 20
<211> LENGTH: 24
<212> TYPE: PRT
<213> ORGANISM: B. taurus

<400> SEQUENCE: 20

Leu Gly Pro Val Glu Leu Ala Ala Val Ile Ala Gly Pro Val Cys Phe
1               5                   10                  15

Val Cys Ile Ala Leu Met Leu Met
            20

<210> SEQ ID NO 21
<211> LENGTH: 24
<212> TYPE: PRT
<213> ORGANISM: G. gallus

<400> SEQUENCE: 21

Leu Gly Pro Val Glu Leu Ala Ala Val Ile Ala Gly Pro Val Cys Phe
1               5                   10                  15

Val Cys Ile Ser Leu Met Leu Ile
            20
```

US 9,296,818 B2

CLEAVAGE INHIBITORS OF TRANSFORMING GROWTH FACTOR BETA TYPE I RECEPTOR AND USES THEREOF IN CANCER THERAPY

RELATED APPLICATIONS

This application is a national stage filing under 35 U.S.C. §371 of international PCT application PCT/US2012/028903, filed Mar. 13, 2012, which claims the benefit of U.S. provisional application No. 61/452,549, filed Mar. 14, 2011 under 35 U.S.C. §119, the entire contents of which are herein incorporated by reference.

BACKGROUND OF THE INVENTION

Transforming growth factor β (TGFβ) is a cytokine that plays an important role during normal embryogenesis due to its multifunctional effects on cellular responses such as proliferation, differentiation, apoptosis, and migration. TGFβ has during recent years become recognized as a potent regulator of cellular plasticity, which is a central event during embryogenesis and tumor progression. TGFβ signals through its binding to the type II and type I serine/threonine kinase receptors (TβRII and TβRI, respectively), resulting in their hetero-oligomerization, which subsequently activates various intracellular signalling pathways. For example, TGFβ activates the kinase activity of TβRI to phosphorylate the latent transcription factors Smad2 and Smad3 in early endosomes, which induces complex formation with Smad4 and nuclear translocation, allowing regulation of target genes. Sorrentino et al., Nat. Cell Biol. 10:1199-1207; 2008. In addition to the Smad pathways, TGFβ/TβR signaling can also activate non-Smad pathways.

TβRI has been found to harbour a consensus binding site for the ubiquitin ligase tumour necrosis factor receptor (TNFR)-associated factor 6 (TRAF6), which was initially identified as mediating the activation of NF-κB by Interleukin-1. Cao et al., 1996. When bound to TGFβ, TRAF6 activates the TGFβ activated kinase 1 (TAK1), which in turn activates p38 mitogen activated protein (MAP) kinase pathway. Yamashita et al., Mol. Cell. 31:918-924; 2008; and Liu et al., Mol. Cell. 35:26-36; 2009. TRAF6 was also known as an E3 ligase, which was reported to interact with TβRI (also known as activin like kinase (ALK) 5) at a highly conserved consensus motif. Sorrentino et al., Nat. Cell Biol. 10(10): 1199-1207; 2008. The TβRI-TRAF6 interaction leads to TGFβ induced TRAF6 autoubiquitination and Lys63-dependent polyubiqitination of TAK1. The activated TAK1 in turn activates MKK3/6 leading to p38 activation and resulting in apoptosis. Thakur et al., Future Oncol. 5(1):1-3; 2009 and Landstrm et al., Int. J. Biochem Cell Biol. 42(5):585-589; 2010.

Posttranslational modifications of TβRI, such as monoubiquitination or Lys63-linked polyubiquitination, have emerged as an important mechanism to control the localization or function of this protein, whereas Lys48-linked polyubiquitination of TβRI was originally described to instead target its substrate for proteasomal degradation (Hershko and Ciechanover 1998, and Ikeda and Dikic 2010). TRAF6 is known to induce Lys63-linked polyubiquitination of its substrates, including TAK1. Yamashita et al., 2008.

SUMMARY OF THE INVENTION

The present disclosure is based on unexpected discoveries that TGFβ induces polyubiquitination of its type I receptor (TβRI) via tumor necrosis factor receptor-associated factor 6 (TRAF6), which, in turn, induces cleavage of TβRI by a cleavage enzyme (e.g., tumor necrosis factor alpha converting enzyme or TACE and presenilin 1 or PS1), leading to nuclear translocation of an intracellular domain of TβRI (TβRI ICD) and activation of genes involved in cancer invasion (e.g., Snail), and that nuclear localization of TβRI ICD, which occurs in cancer cells but not in normal cells, is a reliable cancer biomarker.

Accordingly, one aspect of this disclosure relates to a method for inhibiting cleavage of a TβRI, comprising contacting a cell (e.g., a cancer cell) with a TβRI cleavage inhibitor in an amount sufficient to inhibit cleavage of a TβRI to release a TβRI ICD, thereby blocking the TβRI ICD from translocating to cell nuclei. The contacting step can be performed by administering the TβRI cleavage inhibitor to a subject in need of the treatment (e.g., a human cancer patient).

In another aspect, disclosed herein is a method for reducing invasiveness of cancer cells in a subject (e.g., a human cancer patient), comprising administering to the subject a pharmaceutical composition comprising at least a TβRI cleavage inhibitor in an amount sufficient to inhibit cleavage of a TβRI to release an ICD of the TβRI, thereby blocking the ICD from translocating to the nuclei of the cancer cells and reducing their invasiveness. In some embodiments, the TβRI cleavage inhibitor is administered to a cancer patient in an amount sufficient to reduce metastasis of a cancer (e.g., prostate cancer, renal carcinoma, bladder carcinoma, breast cancer, lung cancer, and colorectal cancer). In some embodiments, the pharmaceutical composition is free of MMP14 inhibitors.

In one example, the cleavage of the TβRI occurs between the G and L residues corresponding to $G_{120}$ and $L_{121}$ in SEQ ID NO: 1 and an amount of the TβRI cleavage inhibitor sufficient to inhibit TβRI cleavage at this site is used in any of the methods described above. In another example, the cleavage of the TβRI occurs between the V and I residues corresponding to $V_{129}$ and $I_{130}$ in SEQ ID NO: 1 and an amount of the TβRI cleavage inhibitor sufficient to inhibit this cleavage is used in the methods described herein.

The TβRI cleavage inhibitor can be (i) an antibody (e.g., a full-length antibody or an antigen-binding fragment thereof) that binds to the TβRI and blocks its cleavage; (ii) an inhibitor of TRAF6, e.g., an anti-TRAF6 antibody (full-length or antigen-binding fragment), a TRAF6-specific interfering nucleic acid, a TRAF6 inhibitory peptide, or a small molecule TRAF6 inhibitor; (iii) an inhibitor of TACE, e.g., an anti-TACE antibody (full-length or antigen-binding fragment), a TACE-specific interfering nucleic acid, or a small molecule TACE inhibitor; (iv) an inhibitor of protein kinase C zeta (PKCζ), e.g., an anti-PKCζ antibody (full-length or antigen-binding fragment), a PKCζ-specific interfering nucleic acid, a PKCζ pseudosubstrate, or a small molecule PKCζ inhibitor, (v) an inhibitor of PS1, e.g., an anti-PS1 antibody (full-length or antigen-binding fragment), a PS1-specific interfering nucleic acid, or a small molecule PS1 inhibitor; or (vi) a combination of any of (i) to (v). In some embodiments, the TβRI cleavage inhibitor is not an inhibitor of MMP14.

The antibody of (i) noted above, which is also within the scope of this disclosure, can be an antibody that binds to the TβRI and blocks cleavage of the TβRI between the G and L residues noted above. In some embodiments, the antibody binds to an antigen epitope (linear or conformational) that encompasses the G residue, the L residue, or both. Alternatively, the antibody binds to the TβRI and blocks its cleavage between the V and I residues also noted above, e.g., binding to an antigen epitope (linear or conformational) that encompasses the V residue, the L residue, or both. In some examples, the antibody binds to an epitope within residues 114-124 in SEQ ID NO:1. Any of the antibodies of (i) as described above can be bispecific antibodies that bind to both TβRI and TACE, MMP14, or PS1.

The TβRI cleavage inhibitor described herein can inhibit TβRI in various cancer cells, including, but are not limited to, prostate cancer cells, renal carcinoma cells, bladder carcinoma cells, breast cancer cells, lung cancer cells, or colorectal cancer cells. It therefore is effective in reducing cancer cell invasion in patients carrying the various types of cancer cells.

In another aspect, provided herein is a diagnostic method, comprising: (i) examining presence or absence of an TβRI ICD in the nuclei of cells in a sample, and, (ii) determining whether the sample contains cancer cells by, e.g., contacting the cells in the sample, or a fraction thereof, with an antibody that binds to the ICD. Nuclear localization of the TβRI ICD indicates presence of cancer cells in the sample. In one example, the sample is suspected of containing cancer cells, such as prostate cancer cells, renal carcinoma cells, bladder carcinoma cells, breast cancer cells, lung cancer cells, or colorectal cancer. In another example, the sample is a tissue sample obtained from, e.g., a patient suspected of having or at risk for a cancer, e.g., those listed above.

The just-described diagnostic method can further comprise a step of assessing the likelihood of cancer invasiveness/metastasis in the subject. Nuclear localization of the ICD indicates that the subject has cancer cells, which are likely to metastasize.

Further, the present disclosure provides a prognostic method comprising (i) examining presence or absence of a TβRI ICD in the nuclei of cancer cells in a tissue sample of a cancer patient, and (ii) assessing invasiveness of the cancer cells. Nuclear localization of the ICD indicates that the cancer cells are invasive. Accordingly, it is predicted that cancer metastasis is likely to occur in the patient. This method can further comprise a step of determining a treatment choice for the patient based on the result obtained from the assessing step. The prognostic methods described herein is applicable to various cancers, including, but are not limited to, prostate cancer, renal carcinoma, bladder carcinoma, breast cancer, lung cancer, or colorectal cancer.

The present disclosure also provides a method for identifying a TβRI cleavage inhibitor. The method comprises (i) contacting a cancer cell that expresses a TβRI with a candidate compound in the presence of TGFβ, which induces TβRI cleavage, (ii) examining presence or absence of an ICD in the nuclear of the cancer cell, and (iii) assessing whether the candidate compound is a TβRI cleavage inhibitor. The candidate compound is identified as a TβRI cleavage inhibitor if (i) the level of ICD nuclear localization in the cell treated with the candidate compound is lower than that in a cell not treated with the candidate compound, or (ii) the level of an extracellular domain of the TβRI in the culture medium of the cell treated with the candidate compound is lower than that in the culture medium of a cell not treated with the candidate compound. In one example, this method is performed in a high-throughput format.

Also within the scope of this disclosure are (a) pharmaceutical compositions for use in inhibiting TβRI cleavage and thus reducing cancer cell invasiveness, the composition comprising any of the TβRI cleavage inhibitors described herein or a combination thereof, and a pharmaceutically acceptable carrier, and (b) use of the TβRI cleavage inhibitors in manufacturing medicaments for the therapeutic uses described herein. Optionally, the pharmaceutical compositions are free of MMP14 inhibitors.

The details of one or more embodiments of the invention are set forth in the description below. Other features or advantages of the present disclosure will be apparent from the following drawings and detailed descriptions of two examples and also from the appended claims.

BRIEF DESCRIPTION OF THE DRAWINGS

The drawings are first described.

DETAILED DESCRIPTION OF THE INVENTION

Figure 1:
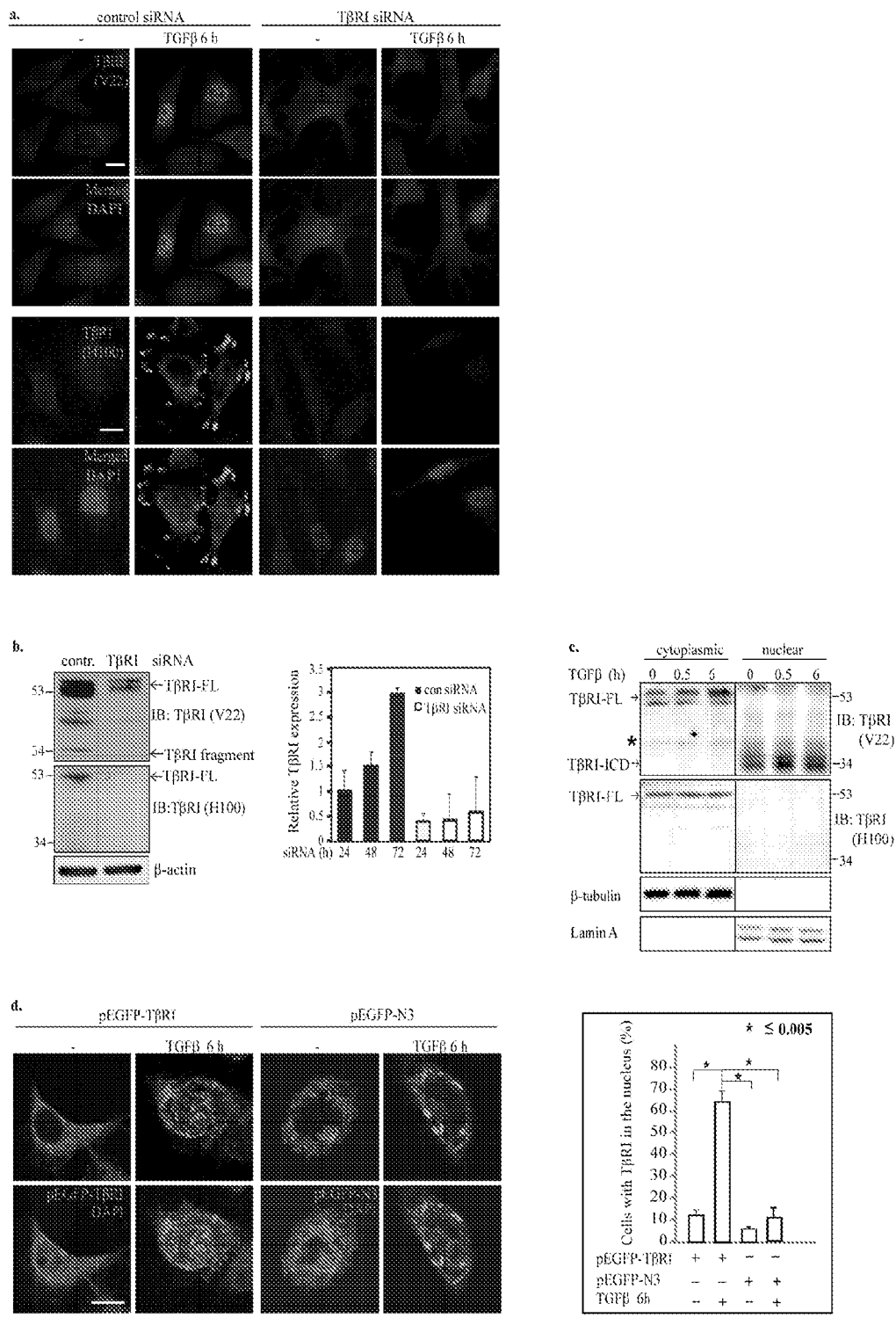
FIG. 1 is a graph showing that TGFβ induces nuclear accumulation of the TβRI intracellular domain (TβRI-ICD). Panels a and b: knockdown of TβRI by siRNA in PC-3U cells to demonstrate specificity of antibodies V22 and H100, which is specific to the C-terminal fragment and N-terminal fragment of TβRI, respectively. In panel b, β-actin served as a loading control. RNA was isolated from untreated or siRNA treated cells 24, 48, and 72 h after transfection. The TβRI mRNA was measured by qRT-PCR (mean±s.e.m., n=3 independent experiments). Panel c: Cell lysates of PC-3U cells treated with TGFβ as indicated were fractionated to produce the cytoplasmic and nuclear protein fractions, which were subjected to SDS-gel electrophoresis. Gels were immunoblotted and probed with the V22 and H100 antibodies. β-tubulin and lamin A served as loading controls for the cytoplasmic and nuclear fractions, respectively. Panel d: Representative confocal microscopy images of C-terminally GFP-tagged wt TβRI (pTβRI-EGFP) and the pEGFP-N3-vector, which were expressed in PC-3U cells treated with TGFβ for 6 h (left). 3-5 independent experiments were performed. Cell nuclei were stained with DAPI. The percent of cells having TβRI nuclear accumulation was quantified (mean±s.d., n=350 cells); scale bar 20 μm (right).

Described herein are methods and compositions for reducing cancer cell invasiveness/cancer metastasis by blocking TβRI cleavage, methods for identifying agents capable of blocking TβRI cleavage, and methods for diagnosing or prognosing cancer based on presence/absence of nuclear localization of TβRI ICD, a product of TβRI cleavage.

(I) Inhibition of TβRI Cleavage and Reduction of Cancer Invasiveness/Metastasis

It is disclosed herein that cleavage of TβRI in response to TGFβ stimulation releases an intracellular domain (ICD) of the TβRI, which subsequently translocates to the nuclei and regulates expression of genes, some of which are essential to cancer cell invasiveness. Accordingly, blocking TβRI cleavage and ICD nuclear translocation would be effective in reducing cancer cell invasion, leading to inhibiting cancer metastasis or lowering the risk of cancer metastasis.

Thus, one aspect of the present disclosure relates to methods for inhibiting TβRI cleavage and reducing cancer cell invasiveness by either inhibiting protein factors involved in this cleavage process or blocking the cleavage site(s) in TβRI, thereby disrupting the interaction between TβRI and a cleavage enzyme at the corresponding cleavage site.

(a) Inhibition of Proteins Involved in TβRI Cleavage

It is disclosed herein that a number of proteins, including TRAF6, TACE, PKCζ, and PS1, are involved in TβRI ubiquitination or the subsequent cleavage. For example, TACE has recently been shown to cleave TβRI in its extracellular domain, causing a loss of TGFβ-induced inhibition of cell proliferation. Huovila et al., Trends Biochem. Sci. 30:413-422; 2005. Thus, one or more of these proteins can be targeted in the methods disclosed herein.

All of the above-listed proteins are well known in the art. As examples, the Genbank accession numbers/Gene IDs for human TRAF6, TACE, PKCζ, and PS1 are listed below:

TRAF6: Gene ID: 7189, GenBank accession number NM_145803,

TACE: Gene ID: 6868, GenBank accession number U69611,

PKCζ: Gene ID: 5590, GenBank accession number Q05513, and

PS1: Gene ID: 5663; GenBank accession number AAC97960.

Inhibitors of the proteins listed above can be used to reduce TβRI cleavage, including, but are not limited to, antibodies specific to the protein targets, interfering nucleic acids that silence expression of these targets, pseudosubstrates, decoy (inhibitory peptides), and small molecule inhibitors.

Antibodies

Antibodies capable of binding to TRAF6, TACE, PKCζ, and PS1 and neutralizing their activities can be used in the methods described herein. Such an antibody can be a full-length antibody or an antigen-binding fragment thereof, e.g., F(ab')$_2$, Fab, or Fv. Such an antibody can be naturally-occurring or genetically engineered, e.g., a humanized antibody, a chimeric antibody, a single-chain antibody, a domain antibody, or a single variable domain (e.g., VH, VL or VHH) or multi-valent or multi-specific constructs made therefrom, or an antibody isolated from an antibody library. A naturally-occurring antibody can be obtained from any suitable species, such as human, rabbit, mouse, guinea pig, and rat, and can be of any immunoglobulin class including IgG, IgM, IgE, IgA, IgD, and any subclass thereof.

Naturally-occurring antibodies against TRAF6, TACE, PKCζ, and PS1, either polyclonal or monoclonal, can be prepared by conventional methods, using these proteins, or fragments thereof as antigens. See, e.g., Harlow and Lane, (1988) Antibodies: A Laboratory Manual, Cold Spring Harbor Laboratory, New York. A monoclonal antibody refers to a homogenous antibody population and a polyclonal antibody refers to a heterogeneous antibody population. These two terms do not limit the source of an antibody or the manner in which it is made.

To produce the above-mentioned antibodies, the protein targets or fragments thereof can be (optionally) coupled to a carrier protein, such as KLH, mixed with an adjuvant, and injected into a host animal. Antibodies produced in the animal can then be purified by a protein A column and/or by peptide affinity chromatography. Commonly employed host animals include, but are not limited to, rabbits, mice, guinea pigs, and rats. Various adjuvants that can be used to increase the immunological response depend on the host species and include Freund's adjuvant (complete and incomplete), mineral gels such as aluminum hydroxide, CpG, surface-active substances such as lysolecithin, pluronic polyols, polyanions, peptides, oil emulsions, keyhole limpet hemocyanin, and dinitrophenol. Useful human adjuvants include BCG (bacille Calmette-Guerin) and *Corynebacterium parvum*.

Polyclonal antibodies are present in the sera of the immunized subjects. Monoclonal antibodies can be prepared using standard hybridoma technology (see, for example, Kohler et al. (1975) Nature 256, 495; Kohler et al. (1976) Eur. J. Immunol. 6, 511; Kohler et al. (1976) Eur J Immunol 6, 292; and Hammerling et al. (1981) Monoclonal Antibodies and T Cell Hybridomas, Elsevier, N.Y.). In particular, monoclonal antibodies can be obtained by any technique that provides for the production of antibody molecules by continuous cell lines in culture such as described in Kohler et al. (1975) Nature 256, 495 and U.S. Pat. No. 4,376,110; the human B-cell hybridoma technique (Kosbor et al. (1983) Immunol Today 4, 72; Cole et al. (1983) Proc. Natl. Acad. Sci. USA 80, 2026, and the EBV-hybridoma technique (Cole et al. (1983) Monoclonal Antibodies and Cancer Therapy, Alan R. Liss, Inc., pp. 77-96). Such antibodies can be of any immunoglobulin class including IgG, IgM, IgE, IgA, IgD, and any subclass thereof. The hybridoma producing the monoclonal antibodies of the invention may be cultivated in vitro or in vivo. The ability to produce high titers of monoclonal antibodies in vivo makes it a particularly useful method of production. After obtaining antibodies specific to the protein targets, their ability to neutralize the activities of these proteins can be determined by routine procedures.

Fully human antibodies capable of binding to TRAF6, TACE, PKCζ, and PS1, such as those expressed in transgenic animals are also features of the invention. See, e.g., Green et al., Nature Genetics 7:13 (1994), and U.S. Pat. Nos. 5,545, 806 and 5,569,825. Fully human antibodies can also be identified by screening human antibody libraries following routine procedures.

Antigen-binding fragments (e.g., F(ab')$_2$, Fab, or Fv) of naturally-occurring antibodies can be generated by known techniques. For example, F(ab')$_2$ fragments can be produced by pepsin digestion of an antibody molecule and Fab fragments can be generated by reducing the disulfide bridges of F(ab')$_2$ fragments.

The antibodies to be used in the methods disclosed herein can also be a genetically engineered antibody, e.g., a humanized antibody, a chimeric antibody, a single chain antibody (scFv), or a domain antibody (dAb; see Ward, et al., 1989, Nature, 341:544-546).

A humanized antibody contains a human immunoglobulin (i.e., recipient antibody) in which regions/residues responsible for antigen binding (i.e., the CDRs, particularly the specificity-determining residues therein) are replaced with those from a non-human immunoglobulin (i.e., donor antibody). In some instances, one or more residues inside a frame region of the recipient antibody are also replaced with those from the donor antibody. A humanized antibody may also contain residues from neither the recipient antibody nor the donor antibody. These residues are included to further refine and optimize antibody performance. Antibodies can also be humanized by methods known in the art, e.g., recombinant technology.

A chimeric antibody is a molecule in which different portions are derived from different animal species, such as those having a variable region derived from a murine monoclonal antibody and a human immunoglobulin constant region. Such an antibody can be prepared via routine techniques described in, e.g., Morrison et al. (1984) Proc. Natl. Acad. Sci. USA 81, 6851; Neuberger et al. (1984) Nature 312, 604; and Takeda et al. (1984) Nature 314:452.

A single-chain antibody can be prepared via recombinant technology by linking a nucleotide sequence coding for a $V_H$ chain and a nucleotide sequence coding for a $V_L$ chain. Preferably, a flexible linker is incorporated between the two variable regions. Alternatively, techniques described for the production of single chain antibodies (U.S. Pat. Nos. 4,946,778 and 4,704,692) can be adapted to produce a phage scFv library and scFv clones specific to any of the target proteins disclosed herein can be identified from the library following routine procedures. Positive clones can be subjected to further screening to identify those that inhibit the activity of TRAF6, TACE, PKCζ, or PS1.

Short Interfering Nucleic Acids

Another family of inhibitory agents to be used in the methods disclosed herein are short interfering nucleic acids (e.g., RNAs) that target TRAF6, TACE, PKCζ, or PS1. These short interfering nucleic acids are oligonucleotides at least a portion of which is complementary (i.e., completely or partially) to a fragment of the nucleic acid coding for any of the protein targets (either the sense chain or the antisense chain), i.e., capable of forming a double-strand duplex via base-pairing according to the standard Watson-Crick complementarity rules. They suppress expression of these protein targets via RNA silencing, i.e., mediating RNA transcript cleavage/degradation or translational repression of the target messenger RNA (mRNA).

Short interfering nucleic acids include, but are not limited to short interfering RNA (siRNA), double-stranded RNA (dsRNA), micro-RNA (miRNA), and short hairpin RNA (shRNA) molecules capable of silencing the expression of the target genes. These nucleic acid molecules can be prepared by chemical synthesis or expressed from a vector via routine recombinant technology. They can be unmodified or chemically-modified. The use of chemically-modified siNA improves various properties of native siNA molecules through, for example, increased resistance to nuclease degradation in vivo and/or through improved cellular uptake. Furthermore, chemical modifications can help the interfering nucleic acids in retaining their RNAi activity. For example, in some cases, siRNAs are modified to alter potency, target affinity, the safety profile and/or the stability to render them resistant or partially resistant to intracellular degradation. Modifications, such as phosphorothioates, for example, can be made to siRNAs to increase resistance to nuclease degradation, binding affinity and/or uptake. In addition, hydrophobization and bioconjugation enhances siRNA delivery and targeting (De Paula et al., RNA. 13(4):431-56, 2007) and siRNAs with ribo-difluorotoluoyl nucleotides maintain gene silencing activity (Xia et al., ASC Chem. Biol. 1(3):176-83, (2006). siRNAs with amide-linked oligoribonucleosides have been generated that are more resistant to S1 nuclease degradation (Iwase R et al. 2006 Nucleic Acids Symp Ser 50: 175-176). In addition, modification of siRNA at the 2'-sugar position and phosphodiester linkage confers improved serum stability without loss of efficacy (Choung et al., Biochem. Biophys. Res. Commun. 342(3):919-26, 2006). In one study, 2'-deoxy-2'-fluoro-beta-D-arabinonucleic acid (FANA)-containing antisense oligonucleotides compared favourably to phosphorothioate oligonucleotides, 2'-O-methyl-RNA/DNA chimeric oligonucleotides and siRNAs in terms of suppression potency and resistance to degradation (Ferrari N et al. 2006 Ann N Y Acad Sci 1082: 91-102).

In some embodiments an siNA is an shRNA molecule encoded by and expressed from a genomically integrated transgene or a plasmid-based expression vector. Thus, in some embodiments a molecule capable of inhibiting gene expression is a transgene or plasmid-based expression vector that encodes a small-interfering nucleic acid. Such transgenes and expression vectors can employ either polymerase II or polymerase III promoters to drive expression of these shRNAs and result in functional siRNAs in cells. The former polymerase permits the use of classic protein expression strategies, including inducible and tissue-specific expression systems. In some embodiments, transgenes and expression vectors are controlled by tissue specific promoters. In other embodiments transgenes and expression vectors are controlled by inducible promoters, such as tetracycline inducible expression systems. Examples of making and using such hairpin RNAs for gene silencing in mammalian cells are described in, for example, (Paddison et al., Genes Dev, 2002, 16:948-58; McCaffrey et al., Nature, 2002, 418:38-9; McManus et al., RNA 2002, 8:842-50; Yu et al., Proc Natl Acad Sci USA, 2002, 99:6047-52).

Inhibitory Peptides, Small Molecule Inhibitors, and Pseudosubstrates

Other inhibitors of TRAF6, TACE, PKCζ, and PS1, including inhibitory (decoy) peptides, pseudosubstrates, and small molecules, are well known in the art. Below are some examples.

Inhibitors of TRAF6 include TRAF6 inhibitory peptides (e.g., those provided by IMGENEX, San Diego, Calif. and disclosed in US 20050130896). Such inhibitory peptides can comprise a TRAF6 binding domain in TβRI, which can be identified based on the consensus TRAF6 binding sequences as disclosed in Sorrentino et al., Nat. Cell Biol. 10(10):1199-1207 and in U.S. Patent Application No. 61/093,181, the content of which is herein incorporated by reference in its entirety.

Inhibitors of TACE include, but are not limited to, TAPI-1, TAPI-2, BMS-561392, DPC-333, Spiro-cyclic b-amino acid derivatives, INCB 3619, GW280264X, TMI-1, and TNF484, DPC-333, Sch-709156, and Doxycycline.

Inhibitors of PKCζ include, but are not limited to, 2-(6-phenyl-1H-indazol-3-yl)-1H-benzol(d)imidazol, ethyl (5E)-2-acetylimino-5-[1-(hydroxyamino)ethylidene]-4-phenyl-thiophene-3-carboxylate, and myristylated pseudosubstrates (see Example 1 below).

Inhibitors of PS1 include, but are not limited to, L685,458 (Hass et al., J. Biol. Chem. 280:9313-9319, 2005) and gamma-secretase inhibitors (e.g., LY-411,575, see US20110059114).

(b) Blockage of Cleavage Site in TβRI

TβRI is a receptor for TGFβ. There are two isoforms of this protein in humans. The GenBank accession numbers for these two isoforms are NM_004612.2 (mRNA) and NP_004603.1 (protein); and NM_001130916.1 (mRMA) and NP_001124388.1 (protein). The amino acid sequences of an exemplary human TβRI is provided below:

Amino acid sequence of TβRI isoform 1 (SEQ ID NO: 1):

```
  1 meaavaaprp rllllvlaaa aaaaaallpg atalqcfchl ctkdnftcvt dglcfvsvte 61 ttdkvihnsm ciaeidlipr drpfvcapss ktgsvtttyc cnqdhcnkie lpttvksspG 121 Lgpvelaavi agpvcfvcis lmlmvyichn rtvihhrvpn eedpsldrpf isegttlkdl 181 iydmttsgsg sglpllvqrt iartivlqes igkgrfgevw rgkwrgeeva vkifssreer 241 swfreaeiyq tvmlrhenil gfiaadnkdn gtwtqlwlvs dyhehgslfd ylnrytvtve 301 gmiklalsta sglahlhmei vgtqgkpaia hrdlksknil vkkngtccia dlglavrhds 361 atdtidiapn hrvgtkryma pevlddsinm khfesfkrad iyamglvfwe iarrcsiggi 421 hedyqlpyyd lvpsdpsvee mrkvvceqkl rpnipnrwqs cealrvmaki mrecwyanga 481 arltalrikk tlsqlsqqeg ikm
```

As disclosed herein, at least two cleavage sites close to the transmembrane domain of TβRI have been identified, i.e., the $G_{120}$-$L_{121}$ site and the $V_{129}$-$I_{130}$ site. See the bold-faced and capitalized residues in SEQ ID NO: 1. Cleavage at either site releases an ICD fragment, which can translocate into the nuclei to regulate gene expression. Thus, agents that bind to TβRI and blocks a cleavage sites from being accessible to a cleavage enzyme can used in the methods disclosed herein.

In some embodiments, the above-noted agents are antibodies that bind to TβRI and block its cleavage. Such antibodies can bind to any antigen epitope of TβRI (linear or conformational) as long as its binding interferes with the association between the cleavage site in TβRI and a cleavage enzyme. Anti-TβRI antibodies described herein can be an antibody of any kind as known in the art, e.g., those described above. In some instances, these antibodies can be full-length antibodies or antigen-binding fragments, e.g., F(ab')$_2$, Fab, or Fv. In other instances, the antibodies can be naturally-occurring antibodies or genetically-engineered antibodies, e.g., a humanized antibody, a chimeric antibody, a single-chain antibody, a domain antibody, or a single variable domain (e.g., VH, VL or VHH) or multi-valent or multi-specific constructs made therefrom, or antibodies isolated from antibody libraries. Methods for preparation of these antibodies are well known in the art, some of which are exemplified above. In one example, such antibodies bind to epitopes in TβRI that encompassing one or both of the residues in the $G_{120}$-$L_{121}$ and/or the $V_{129}$-$I_{130}$ site. Such epitopes can be either linear or conformational. The term "antigen epitope," also known as antigen determinant, refers to a specific portion of a macromolecular antigen to which an antigen binds. It can be either conformational or linear. Typically, a linear epitope is made up of about 6 amino acid residues.

To prepare these antibodies, the TβRI protein, or a fragment thereof (e.g., fragments encompassing one or both residues in the cleavage sites noted above) can be used as an antigen to induce anti-TβRI antibody production in a host system, following the conventional methods as described above. The resultant antibodies are then tested via routine procedures (e.g., see Example 1 below) for identify those that are capable of binding to TβRI and blocking its cleavage. The naturally-occurring antibodies thus obtained can then used to produce genetically engineered antibodies, following the methods also described above.

In other embodiments, the blocking antibodies used in the methods disclosed herein are bispecific, i.e., containing one portion that binds to TβRI and blocks its cleavage and another portion that binds to a protein involved in TβRI ubiquitination and the subsequent cleavage (e.g., TRAF6, TACE, PS1, and PKCζ zeta). Methods for preparing such bispecific antibodies are well known in the art.

Any of the antibodies described herein, including those that bind to TβRI and block its cleavage, and those that bind to one or more of TRAF6, TACE, PS1, and PKCζ zeta and block their activity, can be in isolated form. An isolated antibody refers to an antibody substantially free from naturally associated molecules, i.e., the naturally associated molecules constituting at most 20% by dry weight of a preparation containing the antibody. Purity can be measured by any appropriate method, e.g., column chromatography, polyacrylamide gel electrophoresis, and HPLC. The antibodies can be prepared by any methods known in the art, e.g., those described herein.

(c) Formulation of TβRI Cleavage Inhibitors and Uses Thereof.

One or more of the TβRI cleavage inhibitors disclosed herein can be mixed with carrier, (e.g., a pharmaceutically acceptable carrier) to form a composition (e.g., a pharmaceutical composition), which can be used either in vitro or in vivo. The term "pharmaceutically acceptable" means a non-toxic material that does not interfere with the effectiveness of the biological activity of the active ingredients. Such preparations may routinely contain salts, buffering agents, preservatives, compatible carriers, and optionally other therapeutic agents. When used in medicine, the salts should be pharmaceutically acceptable, but non-pharmaceutically acceptable salts may conveniently be used to prepare pharmaceutically-acceptable salts thereof and are not excluded from the scope of the invention. Such pharmacologically and pharmaceutically-acceptable salts include, but are not limited to, those prepared from the following acids: hydrochloric, hydrobromic, sulfuric, nitric, phosphoric, maleic, acetic, salicylic, citric, formic, malonic, succinic, naphthalene-2-sulphonic, and benzene sulphonic, and the like. Also, pharmaceutically-acceptable salts can be prepared as alkaline metal or alkaline earth salts, such as sodium, potassium or calcium salts.

The pharmaceutical compositions mentioned above may contain suitable buffering agents, including: acetic acid in a salt; citric acid in a salt; boric acid in a salt; and phosphoric acid in a salt.

Suitable buffering agents include: acetic acid and a salt (1-2% W/V); citric acid and a salt (1-3% W/V); boric acid and a salt (0.5-2.5% W/V); and phosphoric acid and a salt (0.8-2% W/V). Suitable preservatives include benzalkonium chloride (0.003-0.03% W/V); chlorobutanol (0.3-0.9% W/V); parabens (0.01-0.25% W/V) and thimerosal (0.004-0.02% W/V).

The pharmaceutical compositions may conveniently be presented in unit dosage form and may be prepared by any of the methods well-known in the art of pharmacy. All methods include the step of bringing the active agent into association with a carrier which constitutes one or more accessory ingredients. In general, the compositions are prepared by uniformly and intimately bringing the active compound into association with a liquid carrier, a finely divided solid carrier, or both, and then, if necessary, shaping the product. Among the acceptable vehicles and solvents that may be employed are water, Ringer's solution, and isotonic sodium chloride solution, but are not so limited. In addition, sterile, fixed oils are conventionally employed as a solvent or suspending medium. For this purpose any bland fixed oil may be employed including synthetic mono- or di-glycerides. Carrier formulations suitable for oral, subcutaneous, intravenous, intramuscular, etc. administration can be found in *Remington's Pharmaceutical Sciences*, Mack Publishing Co., Easton, Pa.

When administered in vivo, the compositions of the present invention can be administered in pharmaceutically acceptable preparations. Such preparations may routinely contain pharmaceutically acceptable concentrations of salt, buffering agents, preservatives, compatible carriers, supplementary immune potentiating agents such as adjuvants and cytokines and optionally other therapeutic agents.

The compositions used in the methods disclosed herein are sterile and in a unit of weight or volume suitable for addition to a cell culture or administration to a subject. As used herein, a subject is a human or non-human animal, including non-human primates, mice, rats, cows, pigs, horses, sheep, goats, dogs, cats, etc. Preferably the subject is a human.

A "subject (e.g., person or patient) having a cancer" is a subject, person or patient that has detectable cancerous cells. The cancer may be a malignant or non-malignant cancer. Cancers or tumors include but are not limited to biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas. Cancers also include cancer of the blood and larynx.

A "subject (e.g., person or patient) suspected of having a cancer" as used herein is a subject, person or patient who may show some clinical or other indications that may suggest to an observer that the subject, person or patient may have cancer. The subject, person or patient suspected of having cancer need not have undergone any tests or examinations to confirm the suspicion. It may later be established that the subject, person or patient suspected of having cancer indeed has cancer.

A "subject (e.g., person or patient) at risk of developing a cancer" as used herein is a subject, person or patient who has a high probability of developing cancer. These subjects include, for instance, subjects having a genetic abnormality, the presence of which has been demonstrated to have a correlative relation to a higher likelihood of developing a cancer and subjects exposed to cancer causing agents such as tobacco, asbestos, or other chemical toxins, or a subject who has previously been treated for cancer and is in apparent remission.

An effective amount of the pharmaceutical compositions described herein can be administered to a subject in need of the treatment (e.g., a human cancer patient) any conventional route, including injection or by gradual infusion over time. An "effective amount" is that amount of a TβRI inhibitor that alone, or together with further doses, produces the desired response, e.g., inhibiting cleavage of TβRI, blocking translocation of a TβRI ICD into the nucleus, and/or reducing cancer cell invasiveness and cancer metastasis. This can be monitored by routine methods known to one of ordinary skill in the art. The amount effective can be the amount of a single agent that produces a desired result or can be the amount of two or more agents in combination. Such amounts can be determined with no more than routine experimentation.

The administration may, for example, be oral, intravenous, intraperitoneal, intramuscular, intracavity, subcutaneous, intrasternal, transdermal and intratumoral. Other modes of administration include mucosal, rectal, vaginal, sublingual, intranasal, intratracheal, inhalation, ocular, and transdermal.

For oral administration, the TβRI inhibitors can be formulated readily by combining the active inhibitors with pharmaceutically acceptable carriers well known in the art. Such carriers enable the compounds of the invention to be formulated as tablets, pills, dragees, capsules, liquids, gels, syrups, slurries, suspensions and the like, for oral ingestion by a subject to be treated. Pharmaceutical preparations for oral use can be obtained as solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents may be added, such as the cross-linked polyvinyl pyrrolidone, agar, or alginic acid or a salt thereof such as sodium alginate. Optionally the oral formulations may also be formulated in saline or buffers for neutralizing internal acid conditions or may be administered without any carriers.

Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or dragee coatings for identification or to characterize different combinations of active compound doses.

Pharmaceutical preparations which can be used orally include push-fit capsules made of gelatin, as well as soft, sealed capsules made of gelatin and a plasticizer, such as glycerol or sorbitol. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In addition, stabilizers may be added. Microspheres formulated for oral administration may also be used. Such microspheres have been well defined in the art. All formulations for oral administration should be in dosages suitable for such administration.

For buccal administration, the compositions may take the form of tablets or lozenges formulated in conventional manner.

For administration by inhalation, the compounds for use according to the present invention may be conveniently delivered in the form of an aerosol spray presentation from pressurized packs or a nebulizer, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g. gelatin for use in an inhaler or insufflator may be formulated containing a powder mix of the compound and a suitable powder base such as lactose or starch.

The inhibitors, when it is desirable to deliver them systemically, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents.

Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Alternatively, the active inhibitors may be in powder form for constitution with a suitable vehicle, e.g., sterile pyrogen-free water, before use.

The inhibitors may also be formulated in rectal or vaginal compositions such as suppositories or retention enemas, e.g., containing conventional suppository bases such as cocoa butter or other glycerides.

In addition to the formulations described previously, the inhibitors may also be formulated as a depot preparation. Such long acting formulations may be formulated with suitable polymeric or hydrophobic materials (for example as an emulsion in an acceptable oil) or ion exchange resins, or as sparingly soluble derivatives, for example, as a sparingly soluble salt.

The pharmaceutical compositions also may comprise suitable solid or gel phase carriers or excipients. Examples of such carriers or excipients include but are not limited to calcium carbonate, calcium phosphate, various sugars, starches, cellulose derivatives, gelatin, and polymers such as polyethylene glycols.

Suitable liquid or solid pharmaceutical preparation forms are, for example, aqueous or saline solutions for inhalation, microencapsulated, encochleated, coated onto microscopic gold particles, contained in liposomes, nebulized, aerosols, pellets for implantation into the skin, or dried onto a sharp object to be scratched into the skin. The pharmaceutical compositions also include granules, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, flavorings, sweeteners or solubilizers are customarily used as described above. The pharmaceutical compositions are suitable for use in a variety of drug delivery systems. For a brief review of methods for drug delivery, see Langer, *Science* 249:1527-1533, 1990, which is incorporated herein by reference.

The compositions may conveniently be presented in unit dosage form and may be prepared by any of the methods well known in the art of pharmacy.

Other delivery systems can include time-release, delayed release or sustained release delivery systems. Such systems can avoid repeated administrations of the compounds of the invention, increasing convenience to the subject and the physician. Many types of release delivery systems are available and known to those of ordinary skill in the art. They include polymer based systems such as polylactic and polyglycolic acid, polyanhydrides and polycaprolactone; nonpolymer systems that are lipids including sterols such as cholesterol, cholesterol esters and fatty acids or neutral fats such as mono-, di and triglycerides; hydrogel release systems; silastic systems; peptide based systems; wax coatings, compressed tablets using conventional binders and excipients, partially fused implants and the like. Specific examples include, but are not limited to: (a) erosional systems in which the polysaccharide is contained in a form within a matrix, found in U.S. Pat. No. 4,452,775 (Kent); U.S. Pat. No. 4,667,014 (Nestor et al.); and U.S. Pat. No. 4,748,034 and U.S. Pat. No. 5,239,660 (Leonard) and (b) diffusional systems in which an active component permeates at a controlled rate through a polymer, found in U.S. Pat. No. 3,832,253 (Higuchi et al.) and U.S. Pat. No. 3,854,480 (Zaffaroni). In addition, a pump-based hardware delivery system can be used, some of which are adapted for implantation.

Controlled release of the TβRI inhibitors can also be achieved with appropriate excipient materials that are biocompatible and biodegradable. These polymeric materials which effect slow release of the inhibitors disclosed herein may be any suitable polymeric material for generating particles, including, but not limited to, nonbioerodable/non-biodegradable and bioerodable/biodegradable polymers.

Such polymers have been described in great detail in the prior art. They include, but are not limited to: polyamides, polycarbonates, polyalkylenes, polyalkylene glycols, polyalkylene oxides, polyalkylene terepthalates, polyvinyl alcohols, polyvinyl ethers, polyvinyl esters, polyvinyl halides, polyvinylpyrrolidone, polyglycolides, polysiloxanes, polyurethanes and copolymers thereof, alkyl cellulose, hydroxyalkyl celluloses, cellulose ethers, cellulose esters, nitro celluloses, polymers of acrylic and methacrylic esters, methyl cellulose, ethyl cellulose, hydroxypropyl cellulose, hydroxypropyl methyl cellulose, hydroxybutyl methyl cellulose, cellulose acetate, cellulose propionate, cellulose acetate butyrate, cellulose acetate phthalate, carboxylethyl cellulose, cellulose triacetate, cellulose sulfate sodium salt, poly (methyl methacrylate), poly(ethylmethacrylate), poly(butylmethacrylate), poly(isobutylmethacrylate), poly(hexlmethacrylate), poly(isodecylmethacrylate), poly(lauryl methacrylate), poly (phenyl methacrylate), poly(methyl acrylate), poly(isopropyl acrylate), poly(isobutyl acrylate), poly (octadecyl acrylate), polyethylene, polypropylene poly(ethylene glycol), poly(ethylene oxide), poly(ethylene terephthalate), poly(vinyl alcohols), poly(vinyl acetate, poly vinyl chloride polystyrene, polyvinylpryrrolidone, hyaluronic acid, and chondroitin sulfate.

Examples of preferred non-biodegradable polymers include ethylene vinyl acetate, poly(meth) acrylic acid, polyamides, copolymers and mixtures thereof.

Examples of preferred biodegradable polymers include synthetic polymers such as polymers of lactic acid and glycolic acid, polyanhydrides, poly(ortho)esters, polyurethanes, poly(butic acid), poly(valeric acid), poly(caprolactone), poly (hydroxybutyrate), poly(lactide-co-glycolide) and poly(lactide-co-caprolactone), and natural polymers such as alginate and other polysaccharides including dextran and cellulose, collagen, chemical derivatives thereof (substitutions, additions of chemical groups, for example, alkyl, alkylene, hydroxylations, oxidations, and other modifications routinely made by those skilled in the art), albumin and other hydrophilic proteins, zein and other prolamines and hydrophobic proteins, copolymers and mixtures thereof. In general, these materials degrade either by enzymatic hydrolysis or exposure to water in vivo, by surface or bulk erosion. The foregoing materials may be used alone, as physical mixtures (blends), or as co-polymers. The most preferred polymers are polyesters, polyanhydrides, polystyrenes and blends thereof.

(II) Diagnostic/Prognostic Methods

It is disclosed herein that nuclear accumulation of a TβRI ICD fragment occurs in cancer cells, but not in normal cells. Thus, nuclear accumulation of the ICD fragment is a reliable biomarker in cancer diagnosis. Further, as translocation of the ICD to the nuclei is associated with expression of genes involved in cancer cell invasion and metastasis, nuclear accumulation of the ICD fragment can also serve as a prognosis marker for predicting cancer progression, particularly metastasis.

Accordingly, provided herein are methods for diagnosing cancer based on presence/absence of a TβRI ICD in nuclei. To perform this method, a cell-containing sample is obtained from, e.g., a subject suspected having cancer or at risk for cancer. Presence/absence of the ICD in the nuclei is then determined via a conventional method. In one example, in situ immunostaining is performed using an antibody that specifically recognizes the ICD. In another example, the cytoplasmic and nuclear protein fractions are prepared from the cells following routine practice (see Examples below) and presence/absence of the ICD in the nuclear fraction is examined via, e.g., Western blot. Nuclear localization of the ICD indicates that the sample contains cancer cell. It also indicates that the cancer cells are invasive.

When the cell-containing sample is a tissue sample obtained from a cancer patient, nuclear localization of the ICD indicates that cancer invasion/metastasis is likely to occur in that patient.

The diagnostic/prognostic methods described above are applicable to human subjects having, suspected of having, or at risk for various types of cancer, including, but are not limited to, biliary tract cancer; brain cancer; breast cancer; cervical cancer; choriocarcinoma; colon cancer; endometrial cancer; esophageal cancer; gastric cancer; intraepithelial neoplasms; lymphomas; liver cancer; lung cancer (e.g. small cell and non-small cell); melanoma; neuroblastomas; oral cancer; ovarian cancer; pancreas cancer; prostate cancer; rectal cancer; sarcomas; skin cancer; testicular cancer; thyroid cancer; and renal cancer, as well as other carcinomas and sarcomas.

(III) Screening for TβRI Inhibitors

Also provided herein are screening methods (e.g., high-throughput screening methods) for identifying TβRI inhibitors that can be used in the treatment methods disclosed herein. Below is an example.

Cancer cells expressing TβRI are cultured in the presence of TGFβ (which induces TβRI cleavage) and a candidate compound for a suitable period of time. The levels of a TβRI ICD in the nuclei are determined as described above. A reduction in the nuclear level of the ICD in cells treated with the candidate compound as compared to that in cells not treated with the compound indicates that the candidate compound is a TβRI cleavage inhibitor.

Alternatively, the levels of an extracellular domain of the TβRI in the culture medium after treatment are determined. A reduced level of the extracellular domain in the culture medium of cells treated with the candidate compound as compared to that in the culture medium of untreated cells indicates that the candidate compound is a TβRI cleavage inhibitor.

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

Example 1

Cleavage of TβRI by TACE Results in Nuclear Translocation of an Intracellular Domain of TβRI and Increased Invasiveness in Cancer Cells Materials and Methods
(i) Cell Culture The human prostate cancer cell line, PC-3U, originating from PC-3, and LNCaP were purchased from ATCC. The cells were grown in RPMI-1640 supplemented with 10% fetal bovine serum (FBS) and L-glutamine.[20] At least 12 h before TGF-β1 stimulation, the cells were starved in RPMI-1640 supplemented with 1% FBS and L-glutamine. Wild-type MEF and TRAF6$^{-/-}$ MEF cells were grown in Dulbecco's modified Eagle's medium (DMEM) containing 10% FBS. Normal human primary prostate epithelial cells (PrEC) were purchased from Cambrex Bio Science, Walkersville. The cells were grown according to the manufacturer's recommendation in Prostate Epithelial Cell Basal Medium supplemented with the Clonetics PrEGM bullet kit, which contains bovine pituitary extract (BPE), hydrocortisone, human epithelial growth factor (hEGF), epinephrine, transferrin, insulin, retinoic acid, triiodothyronine, and GA-1000.

Before TGF-β1 stimulation, the cells were starved for 12-18 h in medium supplemented with 1% FBS. In all assays, the cells were stimulated with 10 ng/ml TGFβ1 (R&D System, UK).

(ii) Antibodies and Reagents

Antibodies or antisera against the following proteins were used: HA (Y-11), ubiquitin (P4D1), TβRI (V22; the specificity of this antibody was previously reported)[21,22], TRAF6 (D10), and p300 (NM11). All of the antibodies were purchased from Santa Cruz Biotechnology. P-Smad2 and TβRI (VPN) antisera were generated in rabbits in-house. Antibodies specific to lamin A, β-tubulin, TACE/ADAM17, pPKCζ/λ (Thr410/403), PKCζ, p-p38, p38, Smad2, and acetyl-Lys were obtained from Cell Signalling. Antibodies against TRAF6 C-term was purchased from ZYMED Laboratories; anti-UbK63 antibodies were from Enzo Life Sciences; UbK48 Clone Apu 207 antibodies were from V.M. Dixit, Genetech; and antibodies against β-actin were from Sigma. The mouse monoclonal TS2/16 antibodies were used to activate or inactivate β1-integrin. Rat anti-human CD29 antiserum was purchased from BD Pharmingen.

Secondary antibodies were horseradish-peroxidase-linked whole anti-rabbit, -goat, or -mouse IgG antisera purchased from Sigma. In some experiments, either goat anti-mouse IgG, light chain specific, or mouse anti-rabbit IgG, light chain specific antisera, purchased from Jackson ImmunoResearch Laboratories, were used. 4,6-Diamidino-2-phenylindole dihydrochloride (DAPI) fluorescent dye (purchased from Merck) and TRITC-labelled phalloidin (from Sigma) were used to visualize cell nuclei by microscopy. Alexafluor 555 was purchased from Invitrogen.

Protein-G Sepharose was obtained from GE Healthcare.; LumiLight Western blotting substrate and Pefabloc were from Roche, PageRuler prestained protein ladder was from Fermentas; and TAPI-2 was from BIOMOL Research Laboratories Inc. TAPI-2 was used at concentrations of 10-20 μM. The p38α/β inhibitor (SB203580) was purchased from Calbiochem (it was used at a concentration of 10 μM). PKCζ pseudosubstrate was from TOCRIS Bioscience and used at concentrations of 10-50 μM. The PKCζ activator, phorbol 12-myristate 13-acetate (PMA, referred to as TPA in our paper), and a TβRI inhibitor (SB505124) were purchased from Sigma. The SB505124 inhibitor was used at a concentration of 10 μM and the TPA at a concentration of 100 nM. The general PKCζ inhibitor, GF109203X, was purchased from Sigma. All inhibitors were added to cells 1 h before TGFβ stimulation.

(iii) Western Blotting, Ubiquitination Assay and Immunofluorescence Microscopy

Cells were starved for 12-18 h and then stimulated with TGFβ for the indicated time periods, washed twice in ice-cold PBS, and lysed in ice-cold lysis buffer (150 mM NaCl, 50 mM Tris pH 8.0, 0.5% (v/v) deoxycholate, 1% (v/v) NP40, 10% (v/v) glycerol, 1 mM aprotinin, 1 mM Pefabloc and 2 mM sodium orthovanadate). After centrifugation, supernatants were collected and protein concentrations were determined using the bicinchoninic acid (BCA) protein measurement kit (Nordic Biolabs). Equal volumes were subjected to immunoprecipitation. Equal amounts of protein from total cell lysates and immunoprecipitations were subjected to electrophoresis on 6%, 10%, 12%, or 4-12% gradient SDS-polyacrylamide gels (SDS-PAGE), blotted on to polyvinylidine difluoride membranes, and subjected to immunoblotting, as previously described.[23] The A495 cell lysate from Santa Cruz was used as a positive control for TβRI. The ubiquitination assays, immunofluorescence assays, and transient transfections were performed as previously described.[5,23,24] Photomicrographs were obtained with a Zeiss 510 Meta (Carl Zeiss Microimaging, Inc.) equipped with a digital camera (RET-EXi-F-M-12-C) from Q-imaging.

(iv) Nuclear Fractionation Assays

Two different protocols for nuclear fractionation were used to evaluate further the finding that TβRI accumulated in the nucleus in response to TGFβ stimulation.

Protocol 1 was used for cell fractionation, as previously described in the experiments shown in FIG. 1d and FIG. 4d.[24] Briefly, cells were washed twice with ice-cold PBS and collected in 1 ml ice-cold PBS then centrifuged (500×g, 5 min, 4° C.). The cell pellet was resuspended in 500 μl buffer A (10 mM MES pH 6.2, 10 mM NaCl, 1.5 mM MgCl$_2$, 1 mM EDTA, 5 mM dithiothreitol, 1% Triton X-100, and protease inhibitors), vortexed for 5 s, and centrifuged (3000×g, 5 min). The resulting supernatant was collected as the cytoplasmic fraction. The nuclear pellet was washed twice with buffer B (Buffer A without Triton X-100), then resuspended in 100 μl buffer C (25 mM Tris/HCl pH 10.5, 1 mM EDTA, 0.5 M NaCl, 5 mM β-mercaptoethanol, and 0.5% Triton X-100), and incubated on ice for 20 min (vortexed every 5 min) to recover the nuclear proteins. The cytoplasmic and nuclear fractions were centrifuged at 12,000×g for 30 min and the supernatants were prepared for immunoblotting.

Protocol 2 was applied in the experiments shown in FIG. 3b. The Nuclear Complex Co-IP kit purchased from Active Motif, performed according to the manufacturer's instructions, was used in Protocol 2. Briefly, cells in a 10-cm dish were washed twice with ice-cold PBS and then scraped and collected in 1 ml ice-cold PBS. After centrifugation at 1500 rpm for 5 min at 4° C., the cell pellet was gently resuspended in 500 μl Hypotonic Buffer and incubated on ice for 15 min. Twenty-five μl of Detergent Solution was added, gently mixed, and centrifuged at 14,000×g for 30 s, at 4° C. The nuclear pellet was resuspended in 100 μl Complete Digestion Buffer. After adding 0.5 μl of Enzymatic Shearing Cocktail, the solution was vortexed gently for 2 s then incubated for 10 min at 37° C. Afterwards, 2 μl of 0.5M EDTA was added to the nuclear lysates to stop the reaction. The mixture was vortexed gently and then incubated on ice for 5 min, centrifuged (14,000×g, 10 min, 4° C.), and the supernatant was collected for immunoprecipitation.

(v) Invasion Assay

Invasion assays were performed using the CytoSelect Cell Invasion Assay (Cell Biolabs, Inc., San Diego, Calif.). Briefly, the basement membrane layer of the cell culture inserts were rehydrated in 300 μl serum-free RPMI-1640 and 2×10$^6$ cells were seeded into the upper sections of the chambers in serum-free RPMI-1640 with or without TGFβ. The lower wells of the invasion plates were filled with 500 μl RPMI supplemented with 10% FBS. Non-invasive cells were removed from the upper chamber and invasive cells were stained with crystal violet cell stain solution. Invasive cells were photographed with a Leica DMR light microscope. Colorimetric quantification was performed by transferring inserts into 200 μl of extraction solution for 10 min and then, transferring to a 96-well microtiter plate. The OD at 560 nm was determined with a plate reader (Supplementary Information FIG. S5a).

(vi) Plasmids and DNA Transfections

GFP-ca TβRI was constructed by inserting the full length ca TβRI between the immediate early promoter of CMV and the EGFP coding sequence. The C-terminus of ca TβRI was fused to the N-terminus of the pEGFP-N3 vector. The pcDNA3 and wild-type PKCζ plasmids were purchased from Addgene. HA-caTβRI and HA-TβRI KR (kinase dead (KD) mutant) with HA fused to the C-terminus of TβRI were obtained from P. ten Dijke (University of Leiden, The Netherlands). Expression vectors for C-terminally tagged HA-tagged G120I mutant of caTβRI were generated by PCR and the mutation was confirmed by sequencing. The caTβRI-E161A plasmid with HA fused to the C-terminus of the TβRI mutant construction was described previously.[5] HA-caTβRI with HA inserted between amino acid 27 and 28 was obtained from Dr. S. Corvera (University of Massachusetts Medical School, Worcester, USA). 3×Plasmids encoding TβRI with the HA epitope inserted between amino acids 27 and 28 was described in Hayes et al., JCB 2002. HA-tagged wild-type ubiquitin and the K48- and K63-only ubiquitin mutants were obtained from Genentech, San Francisco, Calif. Expression vector for GST-TβRI fusion protein, encoding the complete cytoplasmic part (amino acid 148-503) of ca TβRI (T204D) has been described previously as well as the production and purification of the protein.

(vii) siRNA Transfection

Twenty-one-base pair siRNA duplexes targeting ALK5 (5' AAC AUA UUG CUG CAA CCA GGA 3') and SMART pool siRNA targeting TRAF6 were synthesised as previously described.[5] A non-specific control siRNA (5' AAC AGU CGC GUU UGC GAC UGG 3') was synthesized by Dharmacon Research (Lafayette, Colo.). PKCζ siRNA (h2) was obtained from Santa Cruz biotechnology. The siRNAs were transfected into cells using Oligofectamine (Invitrogen), according to the manufacturer's protocol.

(viii) Expression Analysis

Total RNAs were isolated from cells with the RNeasy Minikit (Qiagen) and double-stranded cDNAs were prepared using the Thermoscript RT-PCR System (Invitrogen). Quantitative RT-PCR (qRT-PCR) was performed with the Power SYBR Green PCR Mastermix (Applied Biosystems) and the Stratagene MX3000P. The following primers were used for qRT-PCR:

```
TβRI: forward primer (FP)
5'-TGTTGGTACCCAAGGAAAGC-3', reverse primer (RP)
5'-CACTCTGTGGTTTGGAGCAA-3';

p300: FP
5'-GGGACTAACCAATGGTGGTG-3',

RP
5'-GTCATTGGGCTTTTGACCAT-3';

SNAIL 1: FP
5'-GAGCATACAGCCCCATCACT-3',

RP
5'-GGGTCTGAAAGCTTGGACTG-3';

Smad7: FP
5'-TCCTGCTGTGCAAAGTGTTC-3',

RP
5'-TCTGGACAGTCTGCAGTTGG-3';

MMP-2: FP
5'-AGGCCGACATCATGGTACTC-3',

RP
5'-GGTCAGTGCTGGAGAAGGTC-3';

PAI 1: FP
5'-CTCTCTCTGCCCTCACCAAC-3',

RP
5'-GTGGAGAGGCTCTTGGTCTG-3'.
```

(viiii) Chromatin Immunoprecipitation (ChIP)

ChIPs were performed in three or more biological replicates following the protocol was provided by Abcam, Cambridge UK. Briefly, chromatin was precipitated using the V22 rabbit antibody (Santa Cruz). After precipitation, the DNA was amplified with qRT-PCR to analyze ChIP DNA in triplicate. The following primers were used for ChIP:

Snail1 forward primer 5'-GGACTCAGGGAGACT-CATGG-3', reverse primer 5'-GG GTCTACGGAAAC-CTCTGG-3'.

(x) Histology of Human Tumors

Tissue microarrays (TMAs) on healthy and malignant tissues were performed using anti-TβRI antiserum (V22 and H100). 432 tumor samples, obtained from human patients having various cancers (20 different cancers, including prostate cancer, renal carcinoma and bladder cancer), were analyzed. These malignant samples were provided by the Human Proteome Atlas (HPA) facility (http://www.proteinatlas.org). Stained TMA sections were scanned by high-resolution scanners (ScanScope XT, Aperio Technologies), separated in individual spot images, and evaluated by experienced pathologists.

(xi) Statistical Analysis

Statistical analyses were performed with the Student's t test or ANOVA as indicated in Figure Legends. Values are expressed as mean±s.e.m. of three or more independent experiments, unless otherwise indicated. P values of <0.05 were considered statistically significant.

Results (i) Nuclear Accumulation of an Intracellular Domain (ICD) of TβRI

Figure 15:
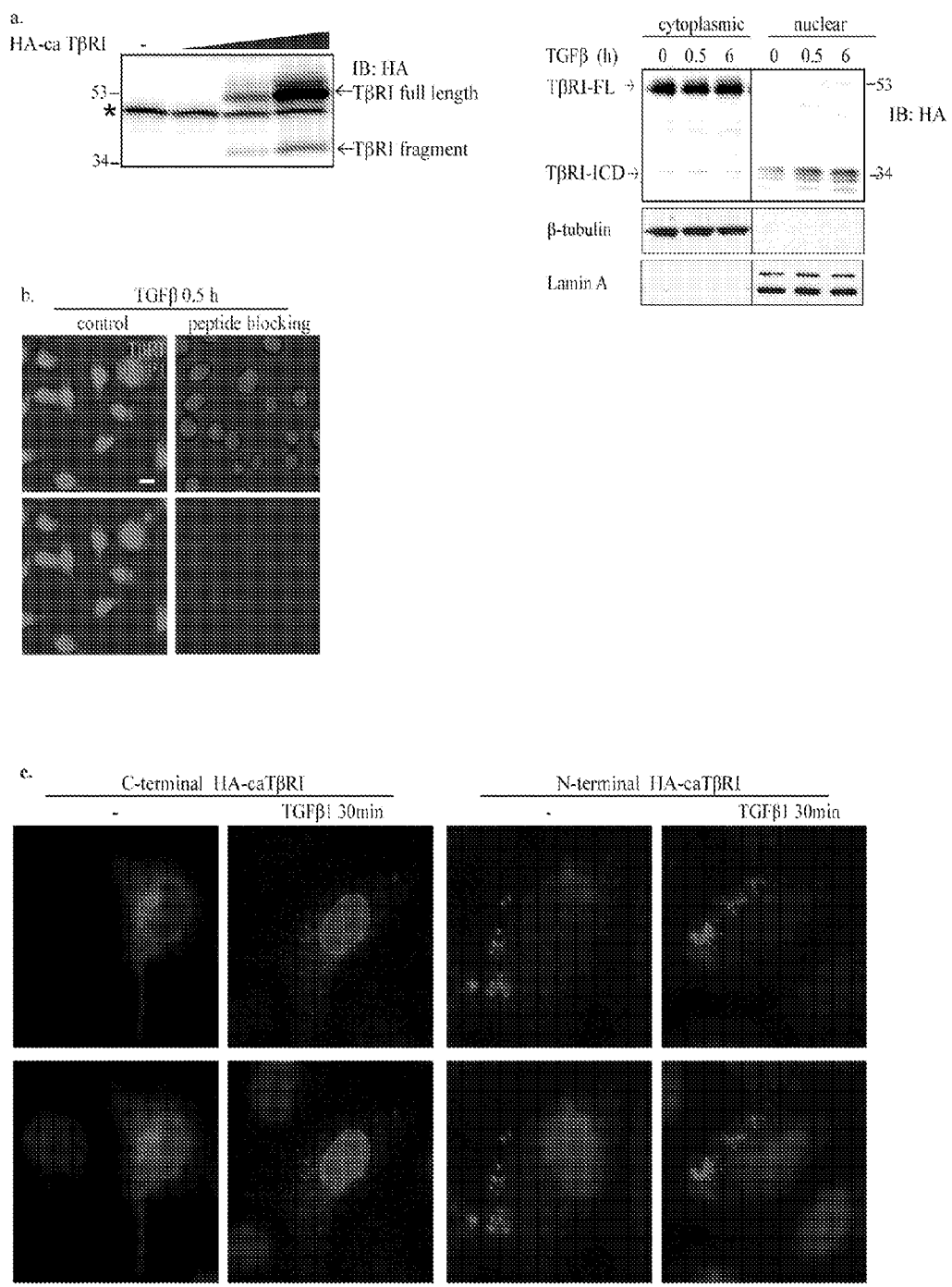
FIG. 15 is a graph showing cleavage of the TGFβ type I receptor (TβRI). Panel a: PC-3U cells were transiently transfected with various amounts of C-terminally tagged HA-TβRI (HA-ca TβRI). The full-length (FL) TβRI migrated at a position corresponding to the molecular weight of 53 kDa in SDS-gel electrophoresis and a TβRI intracellular fragment (ICD) migrated at a position corresponding to the molecular weight of 37 kDa (the asterisk indicates a background band). Panel b: Cell lysates from PC-3U cells transiently transfected with HA-ca TβRI and treated with TGFβ as indicated and fractionated for produce cytoplasmic and nuclear protein fractions, which were subjected to SDS-gel electrophoresis. Gels were immunoblotted and probed with an anti-HA antibody. β-tubulin and lamin A served as loading controls for the cytoplasmic and nuclear fractions, respectively. Panel c, left portion: The nuclear localization of TβRI was detected with the V22 antibody. PC-3U cells were treated with TGFβ for 30 minutes. Control cells (left) were stained with the V22 antibody to visualise endogenous TβRI (green). To demonstrate its specificity, the V22 antibody was incubated with the peptide used for immunization for 1 h at room temperature before adding it to the cells (right; peptide blocking). Panel c, right portion: PC-3U cells ectopically expressing HA-ca TβRI or the N-terminal HA-tagged TβRI were stimulated with TGFβ for 30 min and then stained with an anti-HA antibody (red). Staining with DAPI (blue) was used to visualise cell nuclei. Scale bar 20 µm.

Human prostate cancer cells are known to produce TGFβ2 in an autocrine manner. To investigate whether TβRI can be proteolytically cleaved in human prostate cancer cells, a C-terminally haemagglutinin-tagged, constitutively active (ca) TβRI (HA-ca TβRI) was expressed in PC-3U cells (a human prostate cancer cell line). Notably, in addition to the full length receptor, an anti-HA antiserum recognized a TβRI fragment having the estimated size of an intracellular domain of TβRI. See FIG. 15, panel a. Next, subcellular localization of endogenous TβRI in PC-3U cells was investigated by immunofluorescence and confocal microscopy, using an anti-C-terminal TβRI antibody (antibody V22) or an antibody specific to the extracellular domain of TβRI (antibody H100). As shown in FIG. 15, panel c, an enhanced nuclear accumulation of a C-terminal ICD of the TβRI, recognized by the V22 antibody, was observed after the cells were stimulated by TGFβ. In contrast, immunofluorescence staining revealed that full length TβRI, containing the N-terminal extracellular domain recognizable by the H-100 antibody, was located on the cell membrane of TGFβ-stimulated PC-3U cells. FIG. 15, panel c. To assure the specificity of the V22 bodies and H100-antibodies, siRNA was used to knock-down endogenous TβRI expression in PC-3U cells. See FIG. 1, panel a. qRT-PCR was performed to determine the mRNA levels of TβRI and the results thus obtained demonstrated that they were significantly decreases. FIG. 1, panel b.

To investigate whether nuclear translocation of the ICD fragment is TGFβ-dependent, a nuclear fractionation assay of cell lysates from TGFβ-treated PC-3U cells were performed. When nuclear extracts were immunoblotted with the V22 antibody, a TβRI fragment of approximately 34 kDa was revealed. FIG. 1, panel c. This fragment was not recognized by the H100 antibody, indicating that this fragment is a C-terminal fragment lacking the N-terminal extracellular domain. The full-length TβRI was detected in the cytoplasmic fractions of cells stimulated by TGFβ for 30 minutes, using both the V22 and H100 antibodies. FIG. 1, panel c. By contrast, the 34 kD fragment recognizable by the V-22 antibody was observed only in the nuclear fraction. The levels of TβRI was much lower in nuclear before TGFβ stimulation.

To further investigate the TGFβ-dependency of nuclear accumulation of TβRI, a fusion protein, in which GFP is linked to the C-terminus of TβRI, was expressed in PC-3U cells. After being stimulated with TGFβ for 6 h, fluorescent signal released from GFP was observed in the nuclei of the PC-3U cells that expressed the fusion protein, but not in PC-3U cells expressing GFP. FIG. 1, panel d. The nuclear localization of ectopically expressed C-terminally HA-tagged ca TβRI in PC-3U cells was also examined. The results indicated a TGFβ-induced nuclear accumulation of the HA-tagged ca TβRI-ICD. FIG. 15, panel c. This observation is consistent with the nuclear accumulation of endogenous TβRI-ICD as shown in FIG. 1, panel c. An N-terminally HA-tagged TβRI (see 4) was also expressed in PC-3U cells and the sub-cellular localization of the HA-tagged protein was examined using an anti-HA antiserum. No positive signal was observed in nuclei of PC-3U cells either treated or not treated with TGFβ, indicating that full-length TβRI or its N-terminal fragment does not enter the nucleus. FIG. 15, panel c.

Taken together, the results obtained from this study indicate that an ICD of TβRI enters into the nuclei in PC-3U cells in response to TGFβ stimulation.

(ii) Nuclear Accumulation of TβRI-ICD is Dependent on TRAF6

A consensus TRAF6 binding site for in TβRI was identified recently.[5] Ligand-induced oligomerisation of the TGFβ receptor complex results in receptor kinase-independent activation of TRAF6. This, in turn, results in Lys63-polyubiquitin-dependent activation of TGFβ-activated kinase-1 (TAK1)), which leads to activation of p38 MAPK in PC-3U cells. In contrast, activation of the canonical Smad pathway does not require TRAF6.[5]

Figure 2:
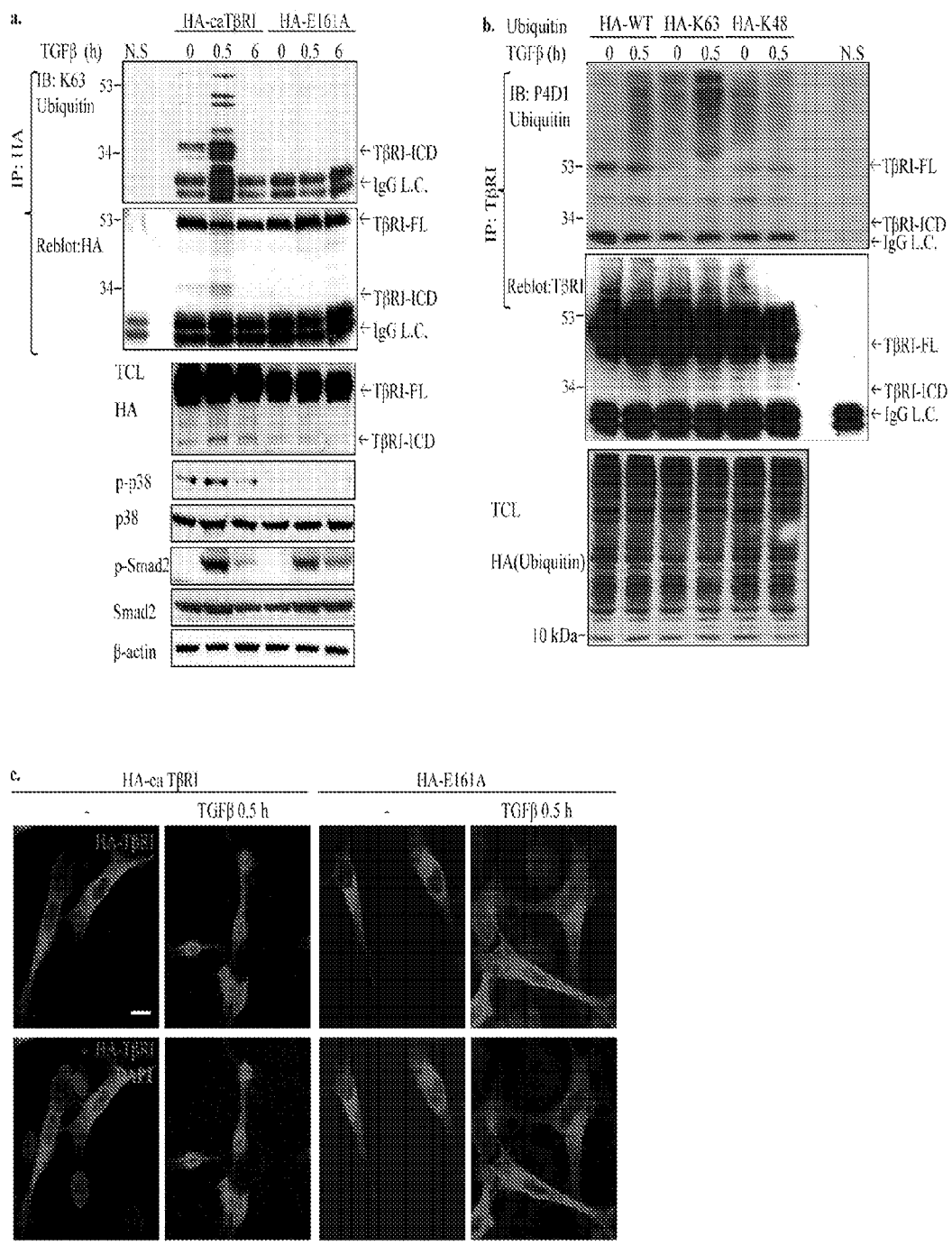
FIG. 2 is a graph showing that TRAF6 promotes Lys63-dependent polyubiquitination of wt TβRI, but not the TβRI E161A mutant. Panel a: PC-3U cells transiently transfected with C-terminally HA-tagged wt TβRI (HA-ca TβRI), or the TβRI E161A mutant (HA-E161A) were treated with or without TGFβ. Ubiquitination of TβRI was examined by an in vivo ubiquitination assay. A fraction of cell lysates was boiled in 1% SDS for 10 min to disrupt non-covalent protein-protein interactions, then diluted (1:10) in buffer. The proteins were immunoprecipitated (IP) with an anti-HA antibody and immunoblotted. Immunoblots (IB) were probed with antibodies specific for Lys63 (K63) linked polyubiquitin. A light-chain specific antibody (IgG L.C.) was used to avoid cross-reaction with the IgG heavy chain. The IP-filter was reblotted with HA to verify equal expression levels of wt TβRI and the E161A mutant. Another portion of the total cell lysates (TCL) was immunoblotted with an anti-HA antibody to detect the TβRI-ICD fragment. Phospho-specific antibodies were used to test whether transcription factors p38 and Smad2 were activated by phosphorylation (p-p38, and p-Smad2, respectively). Panel b: In vivo ubiquitination assays were performed in PC-3U cells transiently transfected with HA-tagged wt ubiquitin and K63 or K48 ubiquitin mutants. Cell lysates were immunoprecipitated with the V22 antibody. K63-dependent polyubiquitination was visualised by probing immunoblots with the P4D1-antisera. An IgG L.C. antibody was used to avoid cross-reaction with the IgG heavy chain. The IP-filter was reblotted with TβRI to verify equal expression of TβRI. The TCL-filter was subjected to immunoblotting with HA-antisera to verify equal expression the wild-type ubiquitin and the mutants. Panel c: PC-3U cells ectopically expressing HA-ca wt TβRI or the E161A mutant were stimulated with TGFβ for 30 min and then stained with an anti-HA antibody (red). Staining with DAPI (blue) was used to visualise cell nuclei (scale bar 20 μm).
Figure 16:
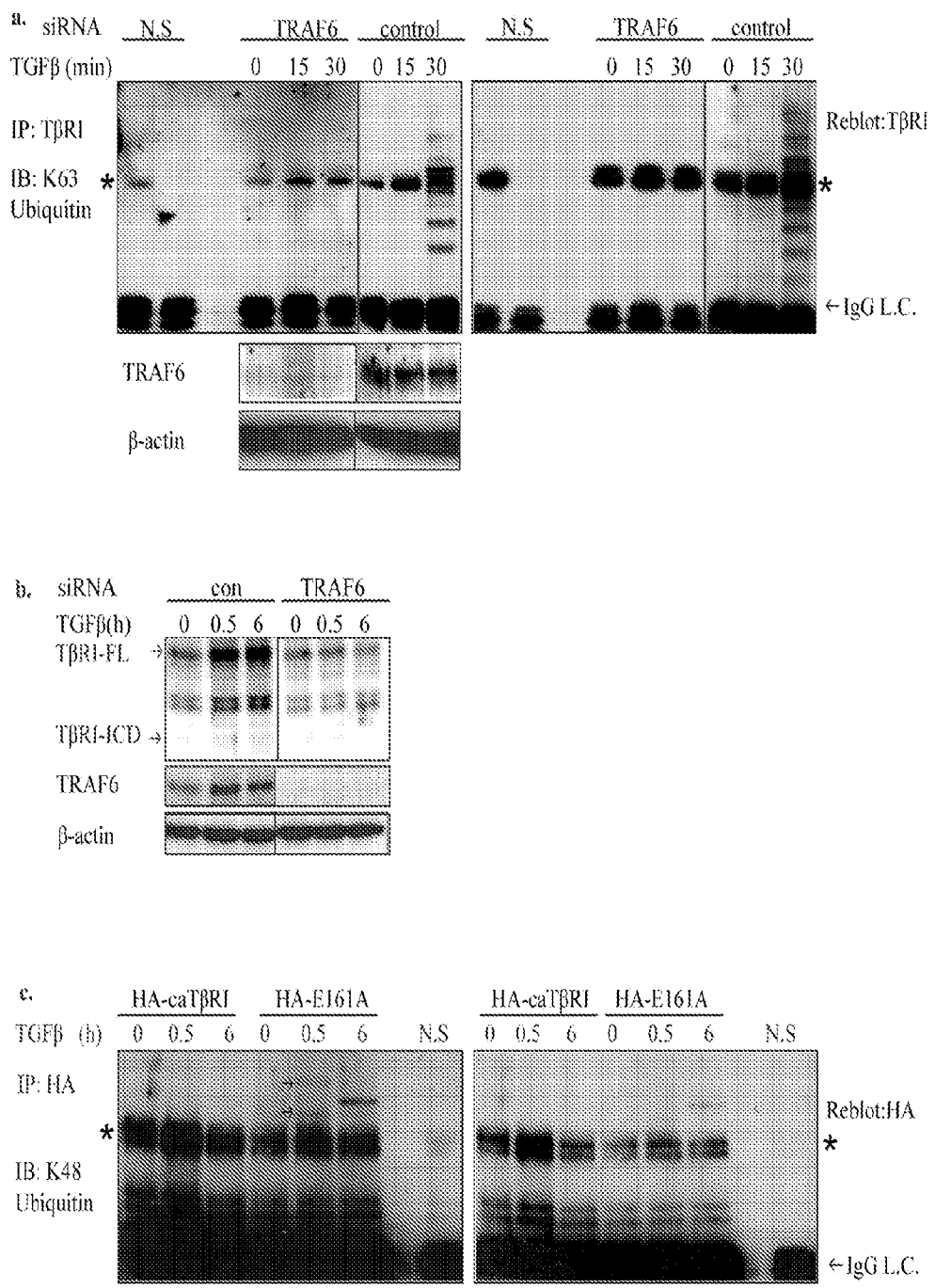
FIG. 16 is a graph showing that TRAF6 promotes TGFβ-induced Lys63-linked polyubiquitination and cleavage of TβRI. Panel a: PC-3U cells were transiently transfected with a control siRNA or an anti-TRAF6 siRNA to silence the endogenous TRAF6. The cells were treated with TGFβ. The ubiquitination of TβRI was examined by an in vivo ubiquitination assay described in Sorrentino et al., 2008. Panel b: PC3U cells were transiently transfected with the control siRNA or the anti-TRAF6 siRNA and then treated with TGFβ, as indicated. Cell lysates were immunoblotted and probed with the V22 antibody to detect endogenous TβRI (full length). Panel c: PC-3U cells were transiently transfected with C-terminally HA-tagged wt TβRI, or the TβRI E161A mutant. Cells were treated with TGFβ, and ubiquitination of TβRI was examined with an in vivo ubiquitination assay. The IP-filter was reblotted with HA to verify equal expression levels of wt and E161A mutant TβRI.

To examine whether TRAF6 is involved in the cleavage and nuclear accumulation of TβRI, a HA-tagged constitutively active TβRI (HA-caTβRI) or a HA-tagged caE161A TβRI mutant (HA-ca E161A), was expressed in PC-3U cells. HA-ca E161A does not bind to TRAF6 but is still capable of activating the canonical Smad signalling pathway.[5] As shown in FIG. 2, panel a, stimulation of PC-3U cells with TGFβ resulted in Lys63-linked polyubiquitination of HA-caTβRI, but not HA-ca E161A. Immunoblotting of total cell lysates with HA antiserum showed that HA-caTβRI was cleaved, producing an ICD fragment. FIG. 2, panel a. Moreover, HA-ca E161A failed to activate the p38 MAPK pathway but could activated Smad2. FIG. 2, panel a. In addition, a knock-down of endogenous TRAF6 in PC-3U cells with an anti-TRAF6 siRNA also resulted in loss of both Lys63-linked polyubiquitination in TβRI and the formation of the TβRI ICD in response to TGFβ stimulation. FIG. 16, panels a and b. Immunoblotting with antibodies specific to either Lys63 or Lys48 polyubiquitin indicated that, 30 min after TGFβ stimulation, wt TβRI contained Lys63 polyubiquitination, but not Lys48 polyubiquitination, in PC-3U cells. FIG. 2, panel a and FIG. 16, panels a and c.

Figure 17:
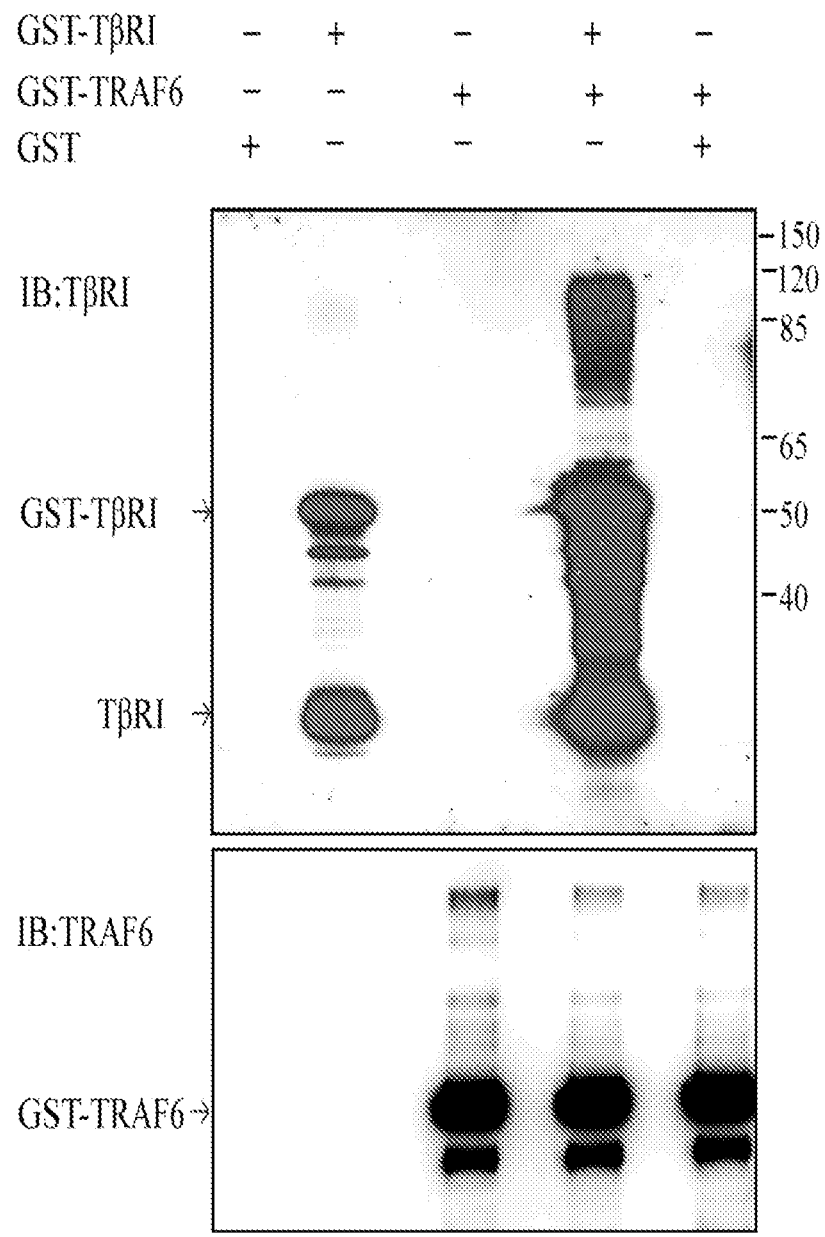
FIG. 17 is a graph showing that TRAF6 acts with the ubiquitin-conjugating enzyme, Ubc13-Uev1A, to promote the polyubiquitination of TβRI in vitro. A GST-TβRI intracellular domain fusion protein were incubated in the presence or absence of a recombinant glutathione-S-transferase-tagged TRAF6 (GST-TRAF6) fusion protein (approximately 0.1 µg at maximum concentration) in a reaction mixture containing 20 mM Tris, pH 7.4, 50 mM NaCl, 10 mM MgCl$_2$, 10 mM dithiothreitol, 10 mM ATP, 0.5 µg µl-1 ubiquitin (Sigma), 2 µM ubiquitin aldehyde (BIOMOL), 100 µM MG132 (Sigma), 0.1 µg E1 (human recombinant from Biomol), 0.2 µg E2 Ubc13-Uev1A (Biomol) at 30° C. for 1 h, then subjected to SDS-PAGE. After incubation at 30° C. for 1 h, the reaction products were immunoblotted (IB) and probed with antibodies against TβRI and TRAF6 to examine the polyubiquitination of TβRI.

The pattern of TβRI polyubiquitination was further examined in PC-3U cells that overexpress HA-tagged wt or mutant ubiquitin, in which all lysine residues were mutated except for Lys63 or Lys48 (K63 or K48). TGFβ induced polyubiquitination of TβRI in cells transiently expressed the K63 ubiquitin mutant. However, in cells expressing the K48 ubiquitin mutant, the level of TGFβ-induced ubiquitination was reduced. FIG. 2, panel b. In addition, TRAF6 was shown to induce the polyubiquitination of TβRI in an in vitro ubiquitination assay, providing firm evidence that TβRI is a substrate for TRAF6. FIG. 17.

The level of TGFβ-induced nuclear accumulation was higher in PC-3U cells expressing HA-caTβRI than in cells expressing HA-ca E161A as analyzed by immunofluorescence stainings. FIG. 2, panel c. This indicates that TRAF6 causes Lys63-dependent polyubiquitination of TβRI in a TGFβ-dependent manner, which, in turn, results in generation of an intracellular fragment of TβRI and its nuclear accumulation.

(iii) TβRI is Cleaved by TACE

When activated, TNF-alpha converting enzyme (TACE) (also known as ADAM17) and ADAM10, both of which are metalloproteases, cleave certain receptors and adhesion proteins at sites just outside cell membranes. TACE was recently shown to cleave TβRI in an ERK MAP-kinase dependent manner, leading to desensitisation of TGFβ signalling. TACE is often overexpressed in tumours and is activated by protein kinase C (PKC).[8]

Figure 3:
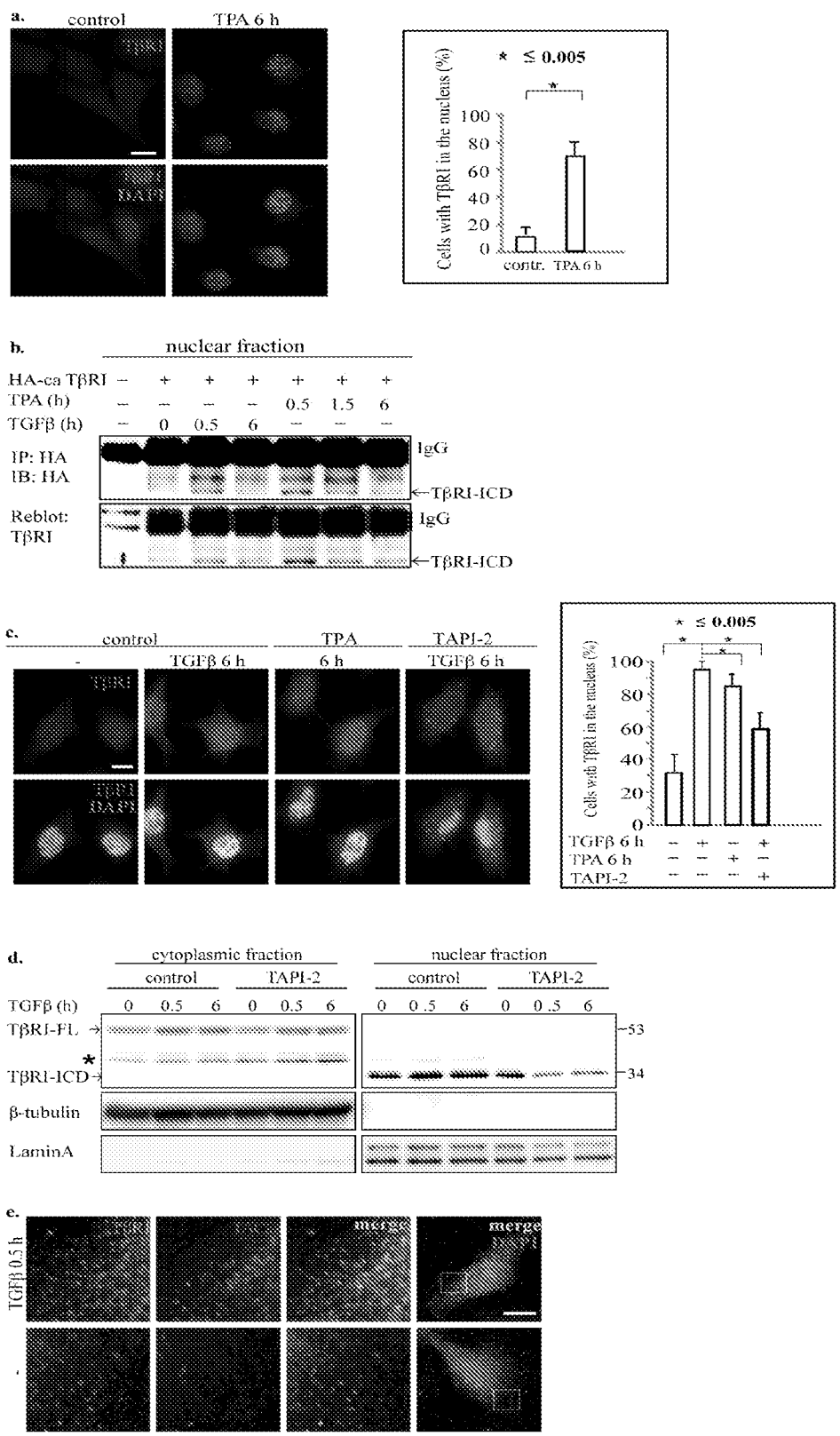
FIG. 3 is a graph showing that TACE regulates nuclear accumulation of the TβRI intracellular domain (ICD). Panel a, left portion: PC-3U cells were treated with TPA for 6 h and prepared for immunofluorescence imaging. Endogenous TβRI was visualised using the V22 antibody (red). Cell nuclei were detected by DAPI (blue) staining. Scale bar 20 μm. Panel a, right portion: Quantification of the percent of cells that showed endogenous TβRI in the nucleus (mean±s.e.m., n=3 independent experiment, where N=200-300 cells counted in each group). Panel b: Cell lysates from PC-3U cells transiently transfected with C-terminally HA-tagged TβRI (HA-ca TβRI) were subjected to immunoprecipitation with an anti-HA antibody. The TβRI-ICD was visualised by immunoblotting with the anti-HA antibody. The membrane was then stripped and reblotted with the VPN antiserum, which is specific to the ICD. Panel c, left portion: PC-3U cells were treated with TGFβ alone, TPA alone, or both TGFβ and TAPI-2 for 6 h. Endogenous TβRI was visualised by immunofluorescence using the V22 antibody (red). DAPI (blue) staining was applied to detect cell nuclei. Scale bar 20 μm. Panel c, right portion: Quantification of the percent of cells that showed endogenous TβRI in the nucleus (mean±s.e.m., n=3 independent experiments, where N=200-300 cells as counted from each group). Panel d: Cell lysates of PC-3U cells were treated with TGFβ in the presence or absence of TAPI-2 as indicated. Cell lysates were fractionated into cytoplasmic and nuclear proteins and subjected to SDS-gel electrophoresis. Gels were immunoblotted and probed with the V22 antibody. β-tubulin and lamin A served as loading controls for the cytoplasmic and nuclear fractions, respectively. Panel e: PC-3U cells were treated with or without TGFβ for 30 min as indicated. Endogenous TACE and TβRI are visualised by co-immunofluorescence with an anti-TACE antibody (TRITC-labeled, red) and the V22 antibody (FITC-labeled, green). Their colocalization is shown by the yellow color, as shown in merged images. The images on the left are enlarged from the areas enclosed in white boxes in the images to the right. DAPI staining was performed to detect cell nuclei (blue).

The role of TACE in TβRI cleavage and nuclear accumulation was investigated to further characterise the underlying molecular mechanisms. Treatment of human PC-3U cells with tetradecanoylphorbol acetate (TPA) to activate PKCζ led to nuclear accumulation of endogenous TβRI ICD, which was detected by immunofluorescence. FIG. 3, panel a. Moreover, when HA-caTβRI-expressing PC-3U cells were treated with TGFβ or TPA, the ICD accumulated in the nuclear fraction. FIG. 3, panel b. Pretreatment of cells with TNF-α protease inhibitor (TAPI)-2, which inhibits TACE, led to a reduction in nuclear translocation of TβRI ICD in response to TGFβ stimulation. FIG. 3, panels c and d. TACE was recently shown to associate with overexpression of TβRI in cells that expressed human epidermal growth factor receptor 2.[9] In a co-immunofluorescence assay, association between endogenous TβRI and TACE was observed in PC-3U cells stimulated with TGFβ. FIG. 3, panel e. These data indicate that activation of TACE, either by TPA treatment or TGFβ stimulation, leads to nuclear accumulation of the TβRI ICD.

(iv) Determination of the TACE Cleavage Site in TβRI

Figure 4:
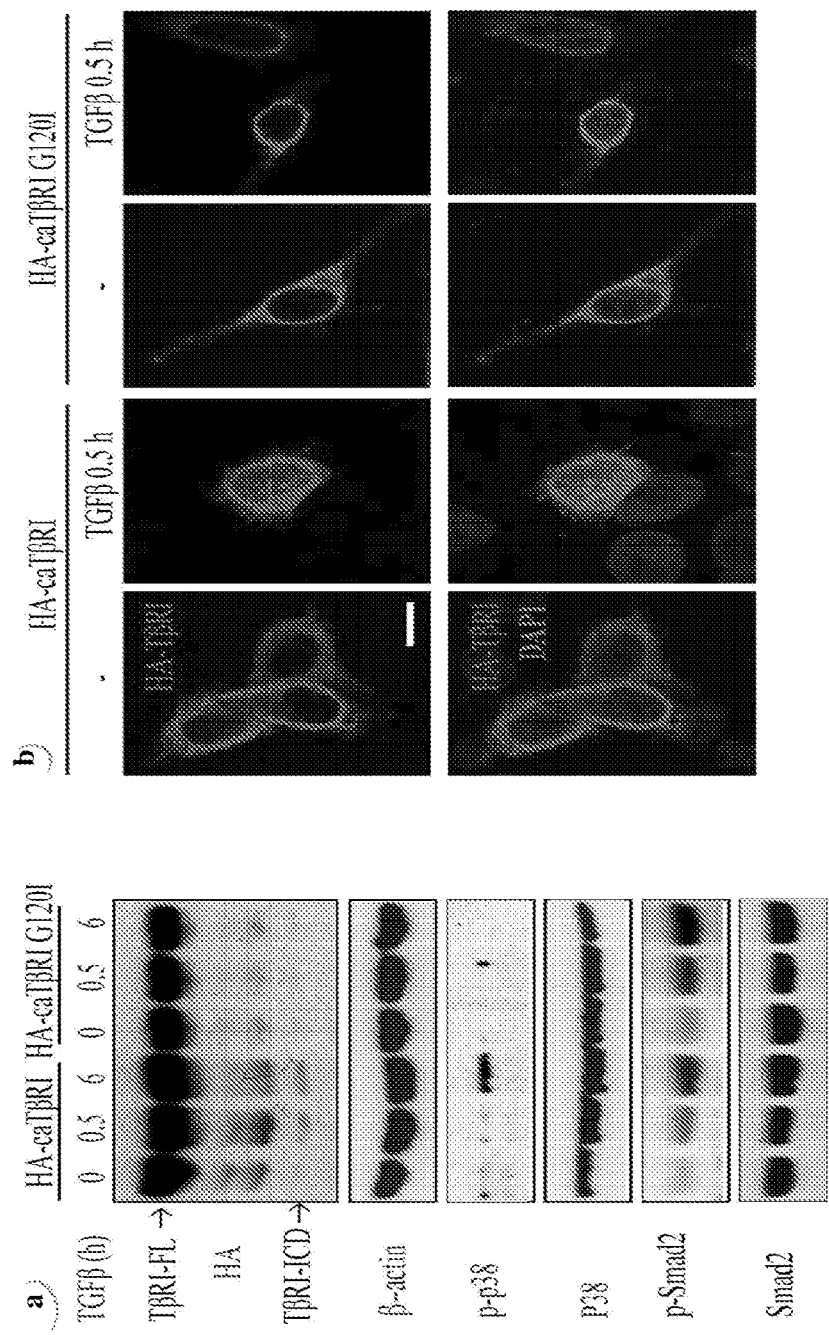
FIG. 4 is a graph showing the Identification of TGFβ induced TACE cleavage site in the extracellular domain of TβRI. Panel a: Total cell lysates, derived from PC-3U cells transiently transfected with wt TβRI or the G120I mutant and stimulated with TGFβ as indicated, were immunoblotted with an anti-HA antibody to detect the TβRI-ICD fragment (the filter was reprobed with β-actin antibodies to show equal loading of proteins in all lanes). Phospho-specific antibodies were used to examine whether transcription factors p38 and Smad2 were activated by phosphorylation (p-p38, and p-Smad2, respectively). Panel b: PC-3U cells ectopically expressing HA-ca wt TβRI or the G120I mutant were stimulated with TGFβ for 30 min and then stained with an anti-HA antibody (red). DAPI (blue) staining was performed to detect cell nuclei. Scale bar 20 μm.

Treatment of PC-3U cells with TAPI-2 partly prevented nuclear translocation of TβRI. This suggests a potential cleavage site in proximity to the transmembrane domain of TβRI. Previous studies with peptide substrates of TNF-α have shown that TACE has a strong preference for cleavage at the Ala-Val sequence and cannot cleave a TNF-α-based peptide when Ala is substituted with Ile at the P1 position. Jin et al., Anal Biochem 302, 269-275, 2002. However, no possible Ala-Val cleavage site was found in the extra-cellular domain of TβRI. TACE has also been shown to have a strong preference for the Gly-Leu sequence and that replacement of this sequence with Gly-Ile blocks cleavage. Chow et al., JBC, 2008. Two Gly-Leu sequences were found in TβRI, $Gly_{52}$-$Leu_{53}$ and $Gly_{120}$-$Leu_{121}$. The putative cleavage site is $Gly_{120}$-$Leu_{121}$, which is in close proximity to the transmembrane domain and would therefore lead to a cleavage product consisting of the complete intracellular domain, including its transmembrane part. To verify that this is the actual cleavage site, $Gly_{120}$ was mutated to Ile to product a G120I mutant. This mutation did not change the subcellular localization of TβRI in untreated PC-3U cells as confirmed by confocal imaging. FIG. 4, panel b. However, its TGFβ-induced nuclear accumulation was prevented, when compared with wt TβRI. FIG. 4, panel b. The G120I mutant preserves the kinase activity as judged by its similar capacity to phosphorylate Smad2, when compared to the wt TβRI. FIG. 4, panel a. These data demonstrate that TACE cleaves TβRI at the $G_{120}$-$L_{121}$ site.

(v) PKCζ is Needed for TACE-Induced Cleavage of TβRI

Figure 5:
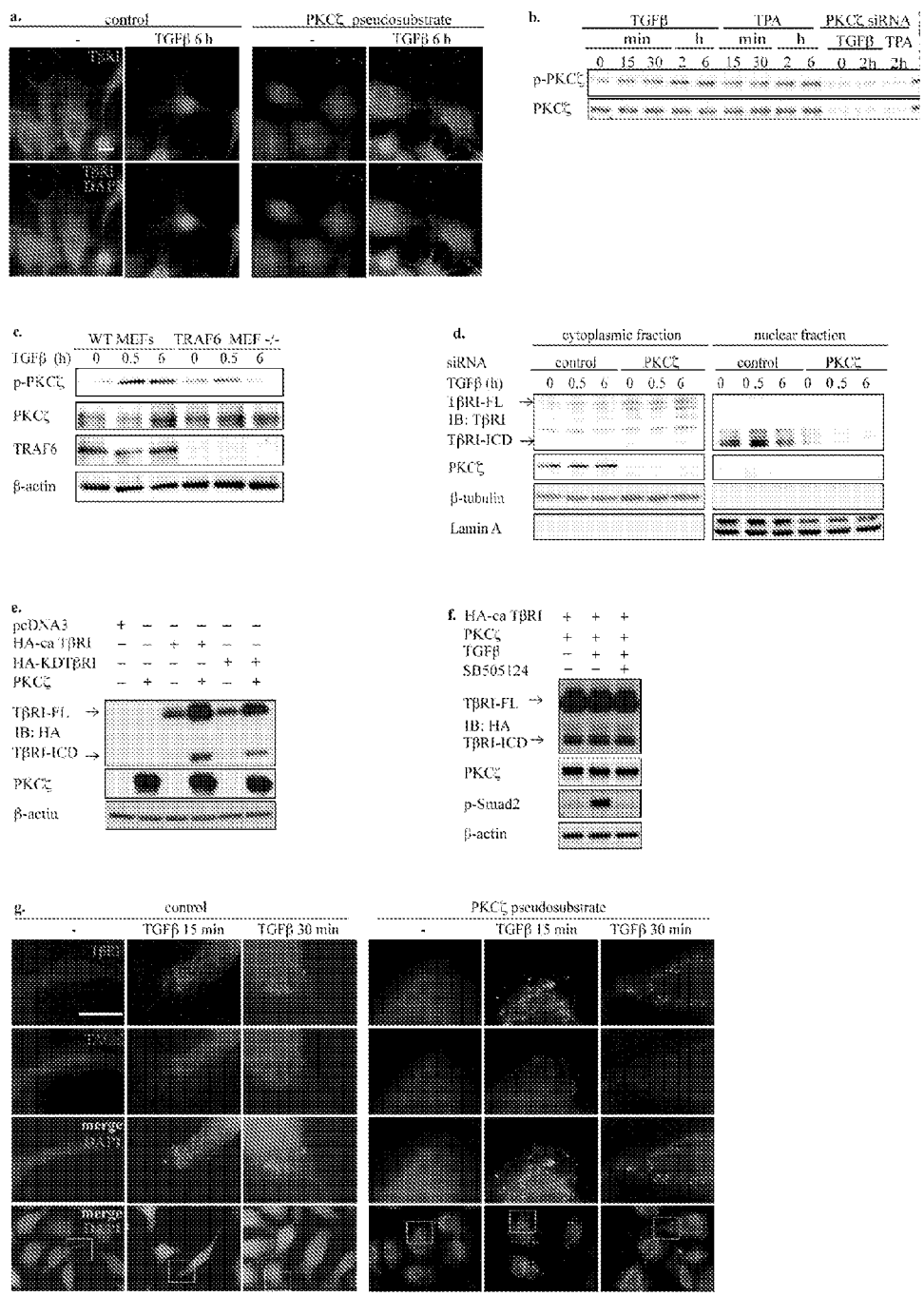
FIG. 5 is a graph showing that PKCζ promotes nuclear accumulation of TβRI. Panel a: Endogenous TβRI in PC-3U cells treated with TGFβ was examined using the V22 antibody via Immunofluorescence in the presence or absence of a PKCζ pseudosubstrate, which inhibits PKCζ. Staining with DAPI was used to visualise cell nuclei (blue). Scale bar 20 μm. Panel b: Cell lysates from PC-3U cells treated with TGFβ or TPA were subjected to immunoblotting with an antiserum against pPKCζ to detect phosphorylated PKCζ (p-PKCζ). Total cell lysates from cells transiently transfected with anti-PKCζ siRNA served as a negative control and cells treated with 10% FBS served as a positive control. The filter was reprobed with an anti-PKCζ antibody to show equal loading of proteins in all lanes. Panel c: Cell lysates from wild-type MEFs and TRAF6−/− MEFs were subjected to immunoblotting with antibodies specific for p-PKCζ. The filter was reprobed with antibodies specific to PKCζ, TRAF6 and β-actin to show, respectively, specificity, knock down of TRAF6 by siRNA, and equal loading of proteins in all lanes. Panel d: PC-3U cells were transiently transfected with siRNA to silence endogenous PKCζ. The transfected cells were treated with TGFβ, subjected to cell fractionation followed by SDS-gel electrophoresis. Samples were immunoblotted to investigate the subcellular localization of endogenous full-length (FL) or the intracellular domain (ICD) of TβRI. Lamin A and β-tubulin served as controls for the nuclear and cytoplasmic fractions, respectively. Panels e and f: PC-3U cells were transiently transfected and treated as indicated, in the presence or absence of wt PKCζ. The HA-KDTβRI is a mutant TβRI with abolished kinase activity. SB505124 is a TβRI kinase inhibitor. Cell lysates were subjected to immunoblotting to detect presence of full-length TβRI and TβRI ICD. Panel g: PC-3U cells were treated with TGFβ with the PKCζ pseudosubstrate. Endogenous TACE and TβRI were visualised by immunofluorescence with an anti-TACE antibodies (TRITC-labeled, red) and the V22 antibody (FITC-labeled, green). Their colocalization is demonstrated by the yellow colour as shown in the merged images. The images in the top three rows are enlarged from the areas enclosed in white boxes in the images below. Staining with DAPI was used to visualise cell nuclei. Scale bar 20 μm.
Figure 18:
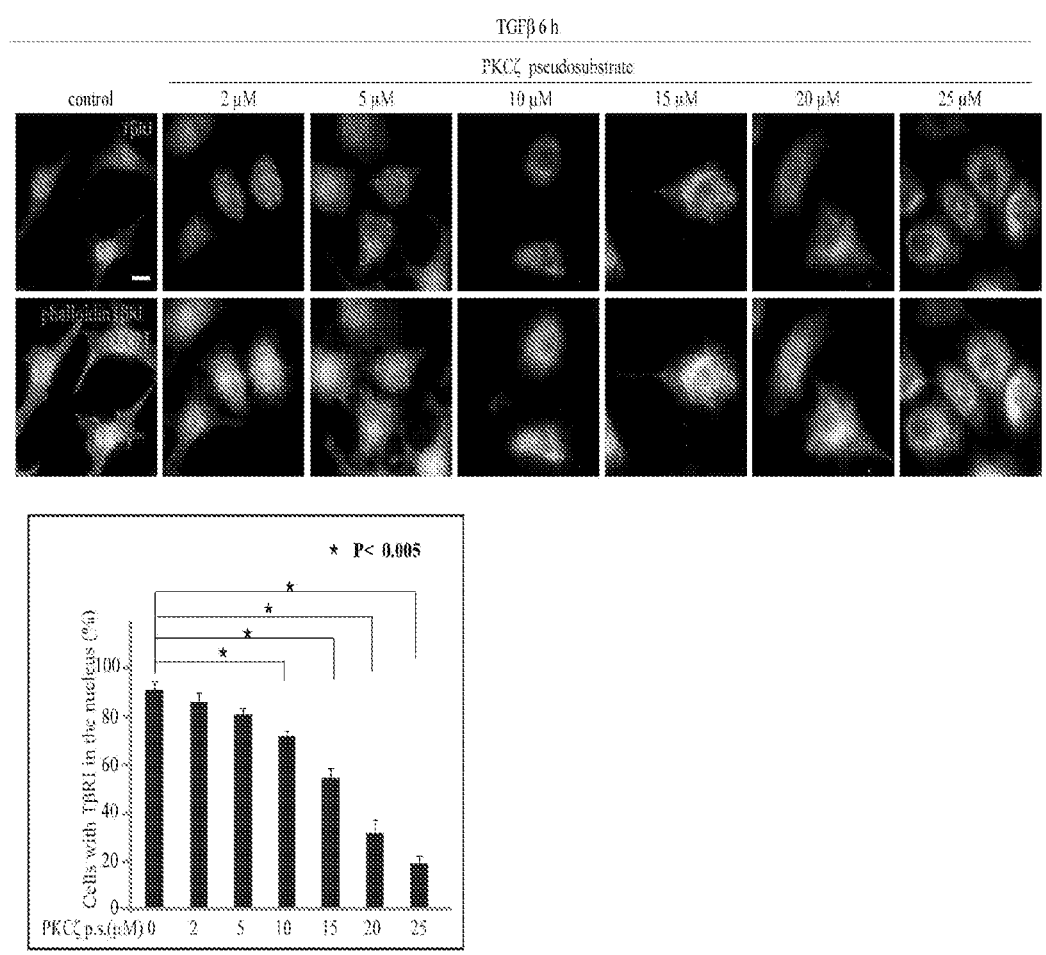
FIG. 18 is a graph showing that PKCζ promotes nuclear accumulation of TβRI. Top panel: PC-3U cells were treated with TGFβ for 6 h and stained for endogenous TβRI in the presence or absence of various amounts of the PKCζ pseudosubstrate. The subcellular localization of the endogenous TβRI was visualized with the V22 antibody (green, top row). The nuclei were stained with DAPI (blue) and the phalloidin stain (red) indicates the cytoplasm. Bottom panel: Quantification of the number of cells shows that the PKCζ pseudosubstrate (p.s.) blocked the PKCζ-induced translocation of endogenous TβRI into the nuclei (mean±s.e.m., n=3 independent experiments where 200-300 cells were counted).

PKCζ is the only member in the PKC-family known to form a multiprotein-complex with TRAF6.[12] Its involvement in TβRI cleavage and nuclear translocation was investigated. Inhibition of PKCζ with the a PKCζ pseudosubstrate completely prevented TβRI nuclear accumulation in a dose-dependent manner. FIG. 5, panel a and FIG. 18. It is well accepted that TPA can activate classical PKCζ family members but not atypical PKCζ isoforms, like PKCζ.[13-14] However, it was found in this study that PKCζ was activated by both TGFβ and TPA. FIG. 5, panel b. TGFβ stimulation did not lead to activation of PKCζ in TRAF6$^{-/-}$-knock-out mouse embryonic fibroblasts (KO MEFs; see FIG. 5, panel c), indicating that TRAF6 is important for TGFβ-induced activation of PKCζ. In a nuclear fractionation assay, siRNA-mediated silencing of PKCζ was associated with a significant loss of TGFβ-induced nuclear accumulation of TβRI ICD. FIG. 5, panel d. In addition, ectopic expression of wt PKCζ promoted expression and cleavage of the caTβRI or the kinase dead (KD) TβRI mutant. FIG. 5, panel e. Treatment of cells with the PKCζ inhibitor partially reduced the formation of the TβRI ICD, but treatment with the TβRI kinase inhibitor, SB505124, had no major effect. FIG. 18 and FIG. 5, panel f.

As shown in FIG. 5, panel g, co-localization of endogenous TβRI and TACE was induced by TGFβ and the co-localization was inhibited by the PKCζ pseudosubstrate. This indicates that PKCζ activity was necessary for proper localisation of TβRI to a subcellular compartment, where it could be cleaved by TACE. In conclusion, TGFβ caused activation of PKCζ in a TRAF6-dependent manner, which was important for the proteolytic cleavage of TβRI by TACE, leading to nuclear accumulation of TβRI ICD.

(vi) TβRI ICD Regulates Transcription

Figure 6:
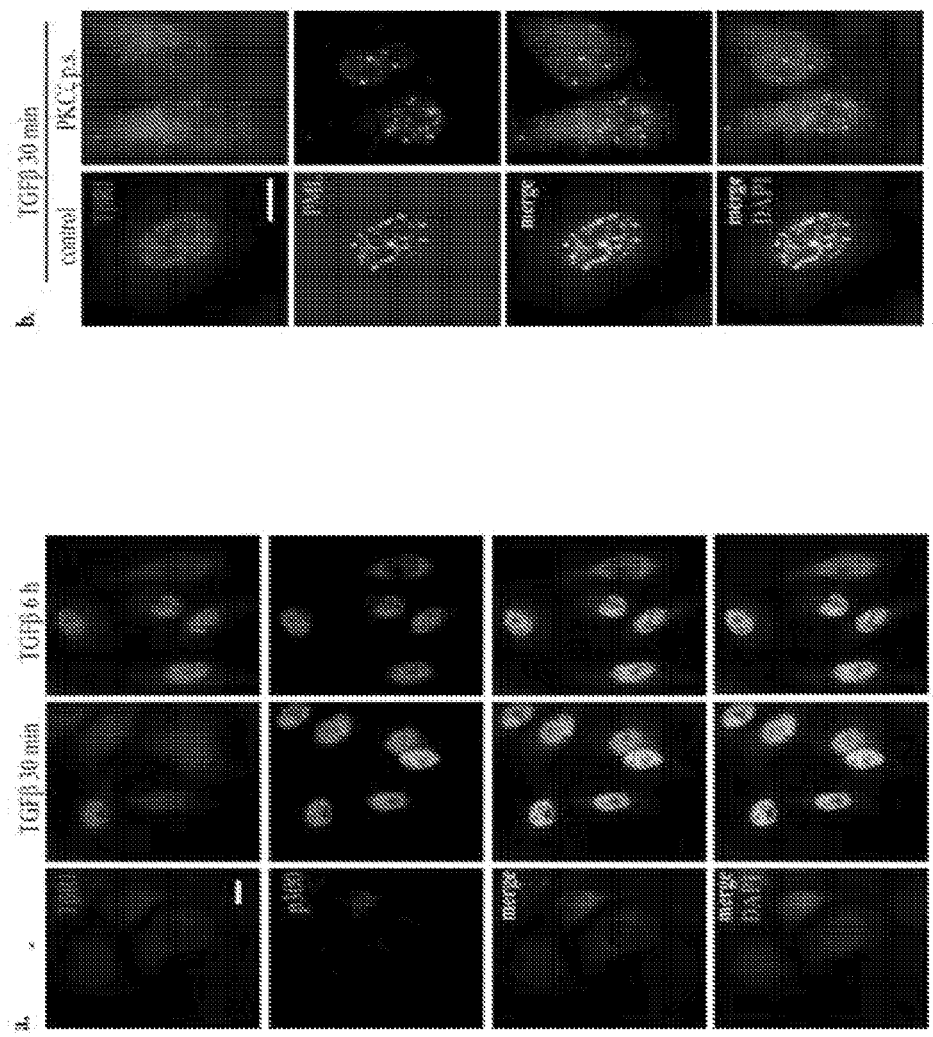
FIG. 6 is a graph showing that TβRI promotes expression of Snail and invasion of prostate cancer cells in a TGFβ-dependent manner. Panel a: PC-3U cells were starved and treated with TGFβ as indicated. Endogenous TβRI and p300 were visualised by immunofluorescence using the V22 antibody (TRITC-labeled, red) and an p300-specific antibody (FITC-labeled, green). Panel b: PC-3U cells were starved and treated with TGFβ in the absence or presence of the PKCζ pseudosubstrate (p.s.) as indicated. Endogenous TβRI and PML were shown by immunofluorescence using the V22 antibody (TRITC-labeled, red) and an anti-PML antibody (FITC-labeled, green). Panel c: TGFβ induces association between endogenous TβRI and p300. Cell lysates from PC-3U cells treated with TGFβ were immunoprecipitated (IP) with the V22 antibody, subjected to SDS-gel electrophoresis, and immunoblotted (IB) with the anti-p300 antibody. Panel d: PC-3U cells were transiently transfected with HA-tagged wt (HA-ca) TβRI or the E161A mutant and treated with TGFβ as indicated. Cell lysates were immunoprecipitated with the anti-p300 antibody, subjected to SDS-gel electrophoresis, and immunoblotted with the anti-HA antibody. Panel e: PC-3U cells were transiently transfected with HA-caTβRI or the E161A mutant and treated with TGFβ as indicated. Cell lysates were immunoprecipitated with an antiserum against HA, subjected to SDS-gel electrophoresis, and immunoblotted with an antibody specific to acetylated lysine (AcK). Panels f and g: qRT-PCR analysis to quantifying the expression levels of p300, Snail-1, MMP2, PAI1, and Smad7, using mRNAs extracted from PC-3U cells that were transiently transfected with HA-caTβRI or the E161A mutant and stimulated with TGFβ for different time periods. Error bars represent the s.e.m. n=3 independent experiments. Panel h: A chromatin immunoprecipitation assay to detect TβRI association with the Snail promoter in PC-3U cells treated with TGFβ1. Immunoblots were probed with the V22 antibody against the endogenous TβRI. Error bars represent s.d. (n=3 independent experiments). Panel i: An invasion assay on PC-3U cells transiently transfected with HA-caTβRI or the E161A mutant and treated with TGFβ or EGF. Cells were visualised by staining with crystal violet cell stain solution. The chart at right represents mean values for optical density (OD) of invasive cells. Error bars represent s.d. (n=3 independent experiments). Panel j: Immunofluorescence staining to detect cytoskeletal reorganisation of actin (phalloidin probe, red) and subcellular localization of TβRI (green) in TGFβ-treated primary prostate epithelial cells (PREC) and PC-3U cells. Staining with DAPI was used to visualise cell nuclei. Scale bar 20 µm. Panel k: Quantification of the percent of cells in panel j that showed endogenous TβRI in the nuclei (mean±s.e.m., n=3 independent experiments, where N=200 cells as counted in each group).
Figure 6:
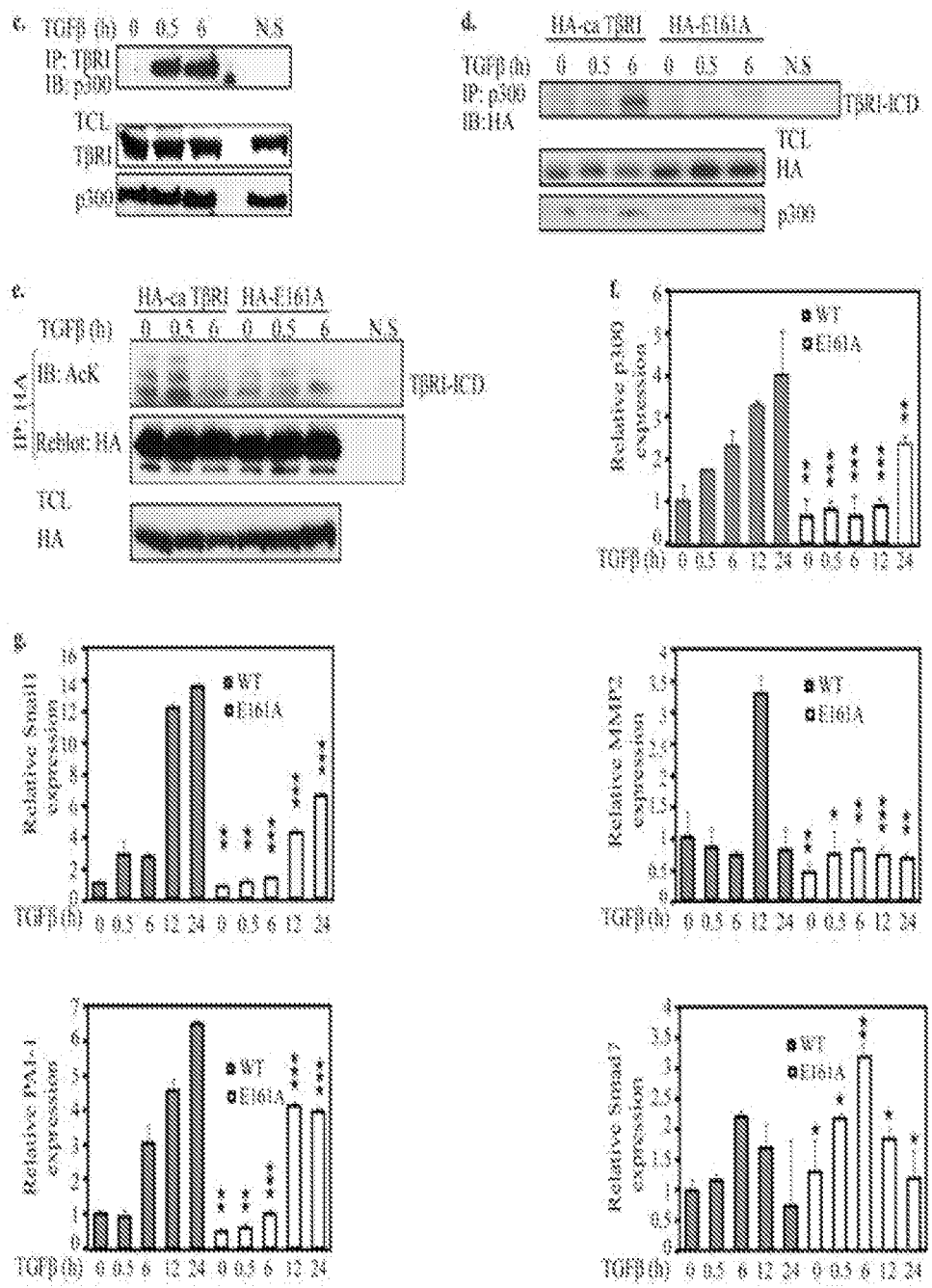
Figure 6:
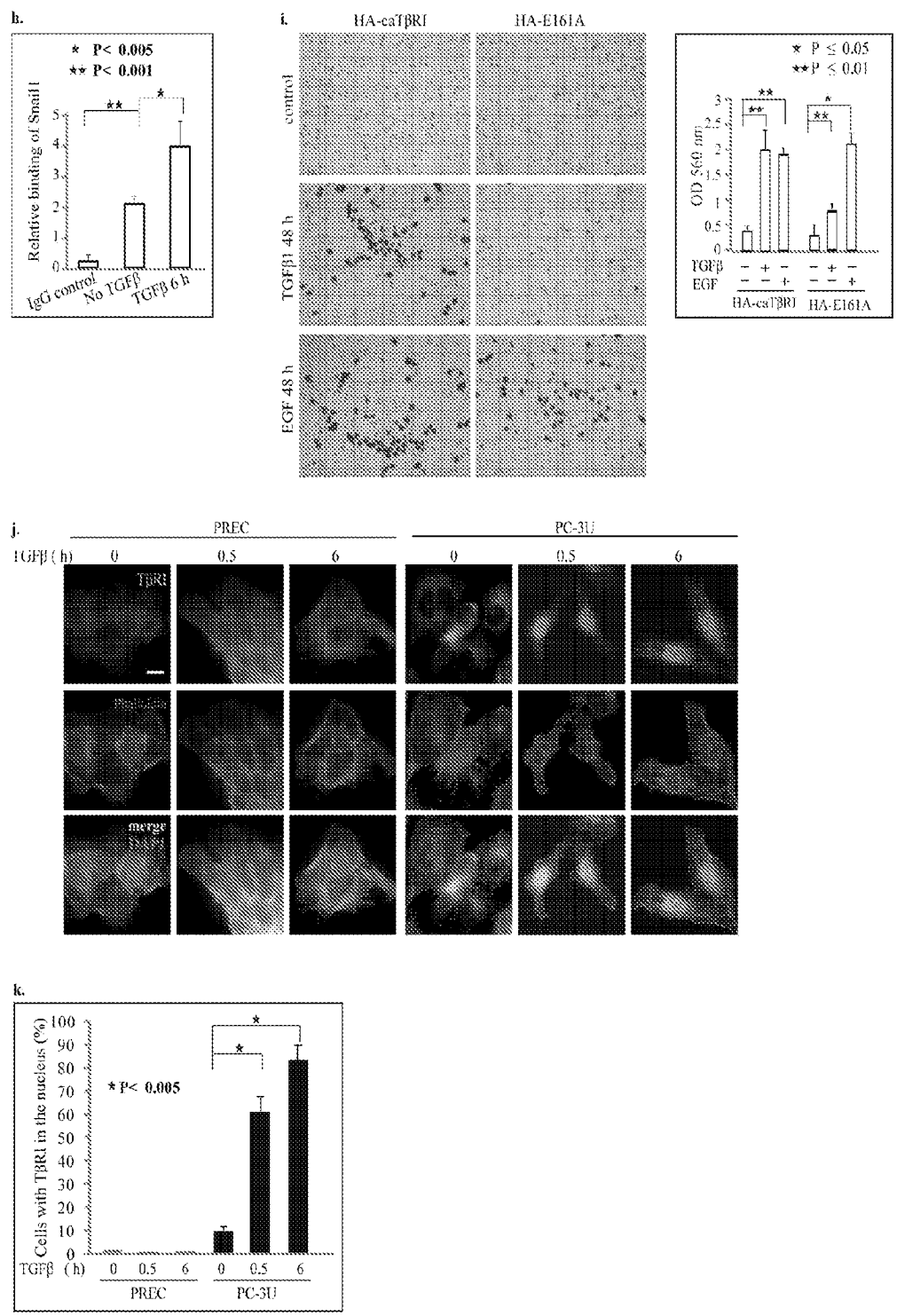

The observation that the TβRI ICD entered the nuclei of TGFβ-treated PC-3U cells suggested that it might participate in gene regulation. Whether nuclear localization of TβRI ICD is associated expression of p300, a well-known transcription regulator, was examined. TGFβ treatment of PC-3U cells led to the co-localisation of TβRI and p300 in nuclear speckles, which were indentified by co-immunofluorescence as PML nuclear bodies.[15] FIG. 6, panels a and b. The PKCζ pseudosubstrate prevented the co-localisation of TβRI with PML nuclear bodies. FIG. 6, panel b. In co-immunoprecipitation assays, the acetyltransferase p300 was found to associate with TβRI ICD in vivo (FIG. 6, panels c and d) and acetylation of the TβRI ICD was verified using an antibody specific for acetyl-lysine. FIG. 6, panel e. In contrast, in cells expressing the E161A mutant, a lower level of TβRI ICD was found to be associated with endogenous p300 and less acetylated ICD was detected. FIG. 6, panels d and e. As compared with cells expressing wt TβRI, the level of p300 was lower in cells expressing the E161A mutant, which is unable to bind TRAF6. FIG. 6, panel d. In an qRT-PCR assay, an increased level of p300 mRNA was observed in TGFβ-induced cells that express wt TβRI, but not in cells that express the E161A mutant. FIG. 6, panel f. These data indicate that TGFβ induces p300 expression in a TRAF6-dependent manner.

Figure 19:
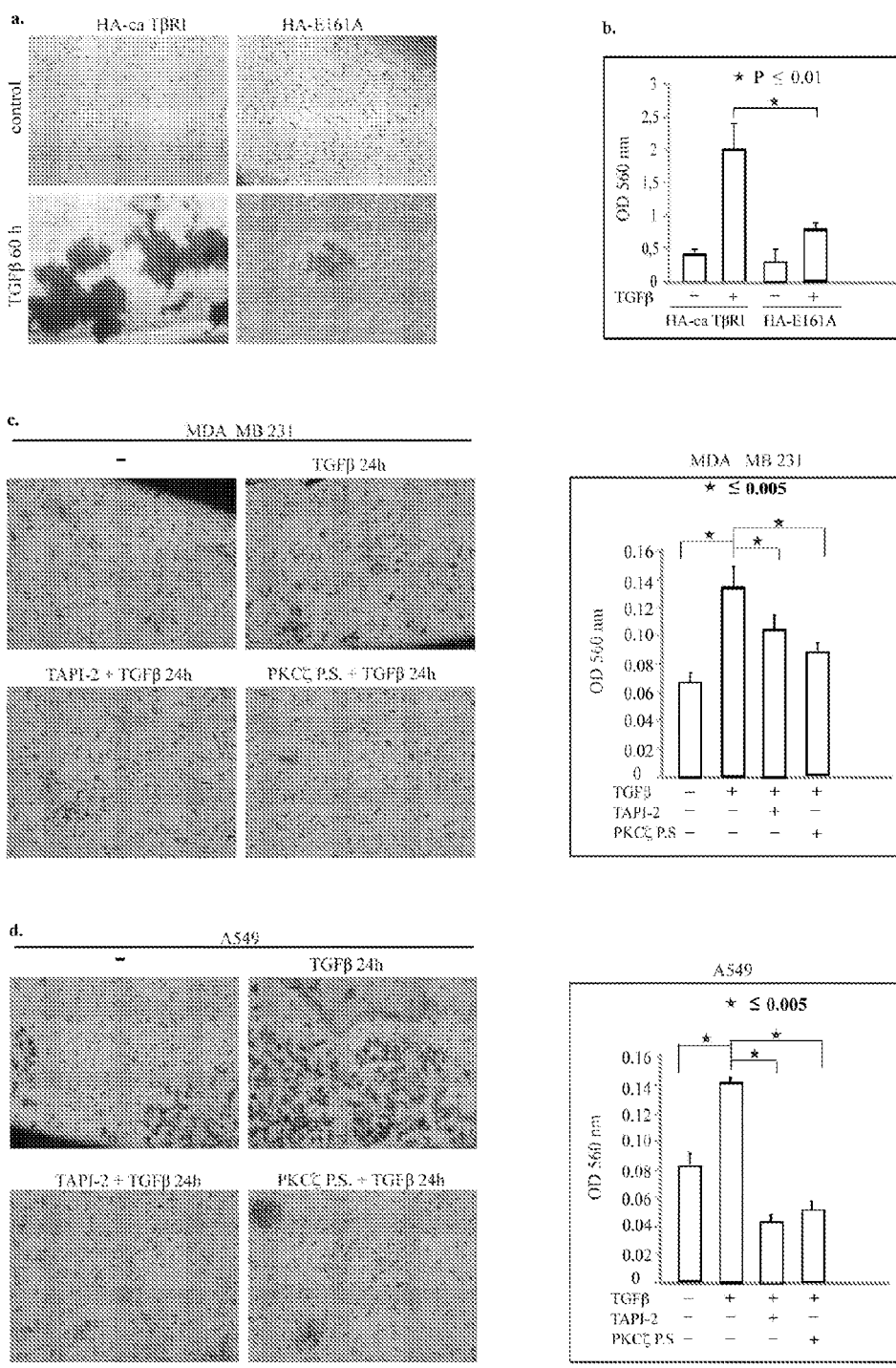
FIG. 19 is a graph showing that TβRI promotes invasion of human cancer cells. Panel a: Invasion assay for human prostate cancer LNCaP cells, which were transiently transfected with the HA-tagged wt (HA-ca TβRI; left) or the E161A mutant (HA-E161A; right) and treated with TGFβs indicated. Cells were visualiszed by staining with crystal violet cell stain solution. Panel b: Quantification of invasive LnCaP cells transiently transfected with wt or E161A mutant TβRI and treated with TGFβ. Invasive cell density was measured by optical density at 560 nm in the invasion assays, (mean±s.d., n=3 independent experiments). P<0.01 by Student's t test. Panel c: Invasiveness of human breast cancer MB 231 cells in response to TGFβ and reduction of cancer cell invasion by TACE and PKCζ inhibitors. Panel d: Invasiveness of human lung cancer A549 cells in response to TGFβ and reduction of cancer cell invasion by TACE and PKCζ inhibitors.

Next, qRT-PCR was performed to analyze the effect of TβRI ICD on known TGFβ target genes, including Snail and MMP2. Expression levels of these two genes (determined by their mRNA levels) were found to be induced by wt TβRI in a degree much greater than the E161A mutant. FIG. 6, panel g. In contrast, genes encoding plasminogen activator inhibitor-1 (PAI1) and the antagonist, Smad7, were induced by both wt TβRI and the E161A mutant. FIG. 6, panel g. A chromatin immunoprecipitation (ChIP) assay revealed binding of TβRI or TβRI ICD to the endogenous Snail promoter in a TGFβ-dependent manner in PC-3U cells. FIG. 6, panel h. The expression of Snail and MMP2 genes is linked to tumour invasiveness.[16] Therefore, PC-3U cells that expressed wt TβRI or the E161A mutant were subjected to an invasion assay. TGFβ-induced invasion occurred in PC-3U cells expressing wt TβRI but not in cells expressing the E161A mutant. By contrast, epidermal growth factor (EGF) stimulated invasion in both cells expressing wt TβRI and cells expressing the E161A mutant. FIG. 6, panel i. Similar results were observed when the experiment was repeated with human prostate cancer cell line LNCaP. More specifically, TGFβ promoted invasion of LNCaP cells that expressed wt TβRI, but not LNCaP cells that express the E161A mutant. FIG. 19, panels a and b. Taken together, the data obtained from this study indicate that the TβRI ICD associated with p300 in nuclear PML bodies in a PKCζ-dependent manner, and is acetylated by p300. Moreover, Snail and MMP2 were induced by TβRI ICD, which correlates with increased cell invasiveness.

(vii) Nuclear Accumulation of TβRI is Found in Malignant but not Normal Prostate Cells Immunofluorescence analysis and confocal microscopy were performed to investigate the subcellular localization of endogenous TβRI in primary human prostate epithelial cells (PrEC) cells and in PC-3U cells, using the V22 antibody that is specific to the C-terminal fragment of TβRI. Results thus obtained show that, after TGFβ stimulation, nuclear accumulation of TβRI or its ICD took place in the malignant PC-3U cells, but not in the normal PrEC cells. FIG. 6, panels j and k.

(viii) TGFβ-Induced Invasion of Human Breast and Lung Carcinoma Cells is Associated with Nuclear Accumulation of TβRI and is Promoted by TACE and PKCζ

Figure 7:
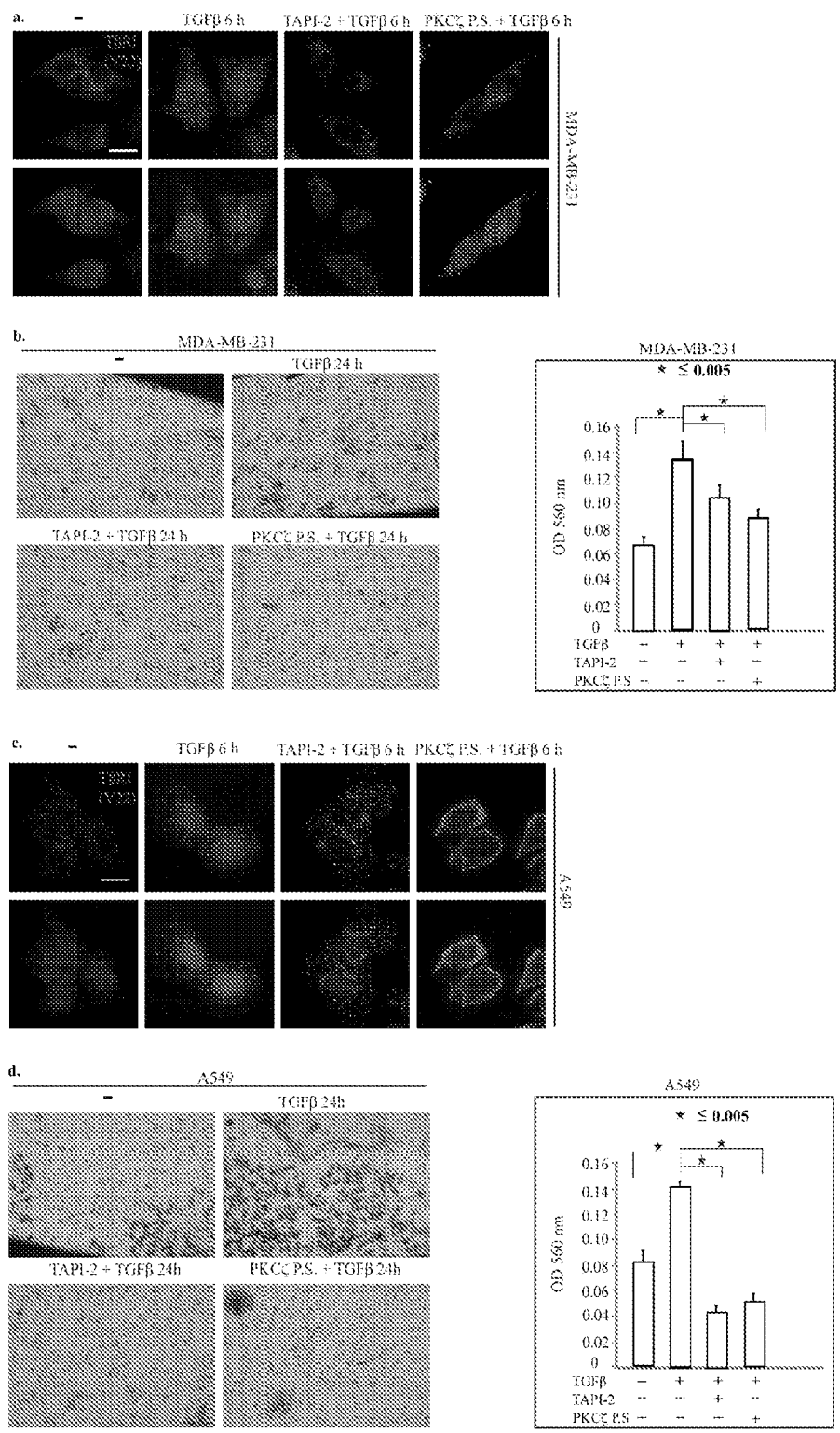
FIG. 7 is a graph showing that endogenous TβRI is localized in nuclei in human lung and breast carcinoma cells and is associated with tumor invasion. Panel a: Human lung (A549) and breast carcinoma (MDA-MB-231) cells were starved and treated with TGFβ in the presence or absence of the PKCζ pseudosubstrate or TAPI-2 as indicated. Endogenous C-terminal TβRI was detected by immunofluorescence using the V22 antibody (TRITC-labeled, red). Panels b and c: Invasion assays on MDA-MB231 and A549 cells treated with TGFβ in the absence or presence of TAPI-2 and the PKCζ pseudosubstrate. Cells were visualised by staining with crystal violet cell stain solution. The right chart shows mean values of the optical density (OD) of invasive cells. Error bars represent s.d. (n=3 independent experiments).

Human breast carcinoma cell line MDA-MB-231 and the human lung carcinoma cell line A549 were used in this study to explore whether the TGF-β induced TβRI nuclear translocation is associated with cancer cell invasiveness. As shown in an immunofluorescence and confocal microscopy assay, TGFβ promoted nuclear accumulation of the endogenous TβRI ICD in both MDA-MB-231 and A549 cells. FIG. 7, panes a-d; and FIG. 5S, panels c and d. The TβRI ICD nuclear accumulation was PKCζ- and TACE-dependent. FIG. 6, panel a.

Next, whether TACE and PKCζ are involved in TGFβ-induced invasiveness of these cancer cell lines was investigated. As shown in FIG. 5S, panels c and d, treatment of MDA MB-231 and A549 cells with TACE and PKCζ inhibitors significantly reduced TGFβ-induced invasion.

(viiii) Nuclear Accumulation of TβRI in Human Tumors In Vivo

Figure 8:
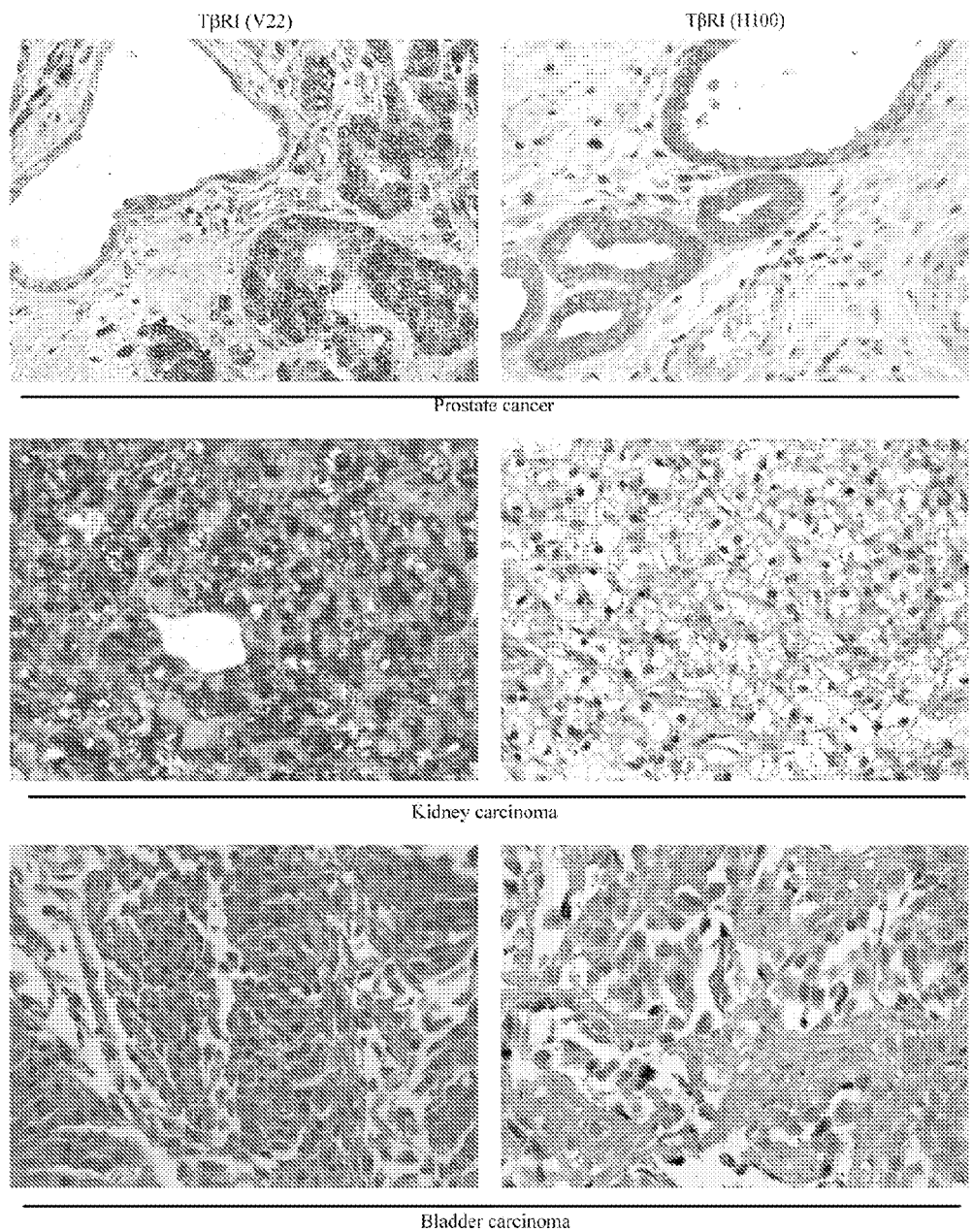
FIG. 8 is a graph showing that endogenous TβRI is localized in nuclei in various types of malignant tumors. Tumor tissues from prostate cancer, renal carcinoma, and bladder cancer were stained with the V22 and H100 antibodies.

To explore whether nuclear accumulation of the TβRI ICD occurs in human tumors, immunohistochemistry was performed to investigate the expression and localization of TβRI in a panel of prostate and renal cell carcinomas and bladder tumors. Nuclear accumulation of TβRI ICD was observed in all of the 19 investigated prostate carcinoma tissues, in 19 out of the 24 renal cell carcinomas tissue samples, and in 21 out of the 23 bladder tumors samples, using the V22 antibody. Staining with the H100 antibody, which recognizes the extracellular part of TβRI, only showed cytoplasm localization. FIG. 8. These data indicate that nuclear accumulation of TβRI or its ICD occurs in human tumours.

Discussion

Figure 20:
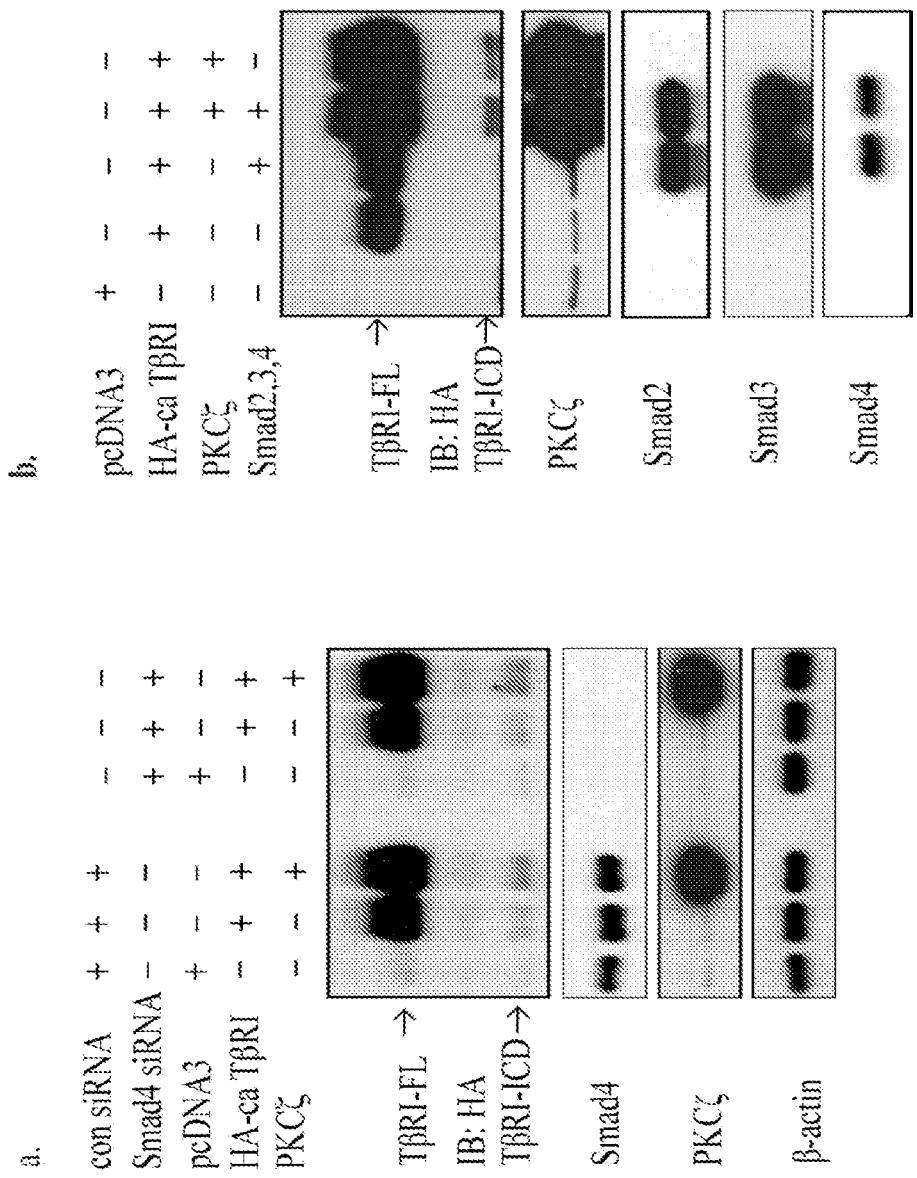
FIG. 20 is a graph showing that the levels of Smads do not influence PKCζ-dependent generation of TβRI-ICD. Panel a: PC3U cells were transiently transfected with a control siRNA and an anti-Smad4 siRNA, pcDNA3, C-terminally HA-tagged TβRI, alone or together with PKCζ as indicated. Cell lysates were immunoblotted and probed with an anti-HA antibody to detect TβRI-ICD. Total cell lysates were also subjected immunoblotting with anti-Smad4 and anti-PKCζ antibodies (full length TβRI=TβRI-FL). One of the filters was stripped and reprobed with an anti-β-actin antibody to serve as a control for equal loading of proteins. Panel b: PC3U cells were transiently transfected with C-terminally HA-tagged TβRI alone or together with Smad2, 3, 4, and PKCζ as indicated. Cell lysates were immunoblotted and probed with the anti-HA antibody to detect TβRI-ICD. Total cell lysates were subjected immunoblotting using antibodies against Smad2, Smad3, Smad4 and PKCζ.

It has been shown herein that, in response to TGFβ stimulation, TβRI undergoes cleavage by TACE in cancer cells and that an ICD segment of TβRI is translocated to the nuclei of the cancer cells to interact with transcriptional regulator p300 in nuclear PML bodies. It has also been shown herein that nuclear accumulation of the TβRI ICD is dependent on TRAF6, TACE, and PKCζ. Overexpression of Smad2, 3 or 4 in PC-3U cells did not influence PKCζ-induced generation of TβRI ICD. FIG. 20, panel a. Knock down of Smad4 by siRNA also did not affect the PKCζ-induced generation of TβRI ICD. FIG. 20, panel b. Moreover, in MDA-MB468 cells, which are Smad4-deficient, the TβRI ICD formed in cells treated with TGFβ. Since cells expressing the E161A mutant, which cannot bind to TRAF, still exhibits Smad2 activation but did not produce the TβRI ICD, it indicates that the Smad pathway can operate independently of TβRI ICD formation, which correlates with activation of the TRAF6, TAK1, and p38 MAPK pathways. FIG. 2, panel a.

Figure 21:
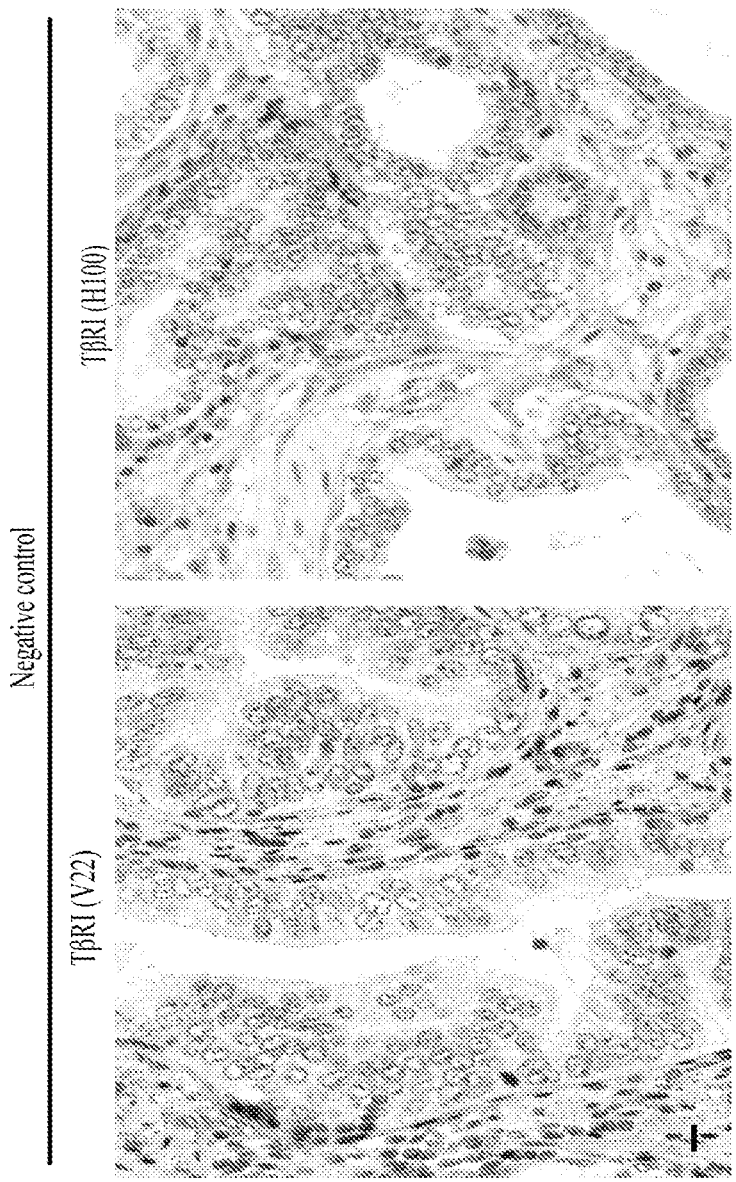
FIG. 21 shows negative controls of TbRI immunohistochemical stainings in prostate cancer tissues, using the V22 and H100 antibodies.

Integrins are essential adhesion receptors localized on the surfaces of all metazoan cells and are involved in cell migration and extracellular matrix assembly.[17] Integrins forms membrane-spanning heterodimers, which are critical for embryonic development, tissue repair, and immune responses. Anthis N J, Campbell I D, 2011. TGFβ-induced activation of the p38 MAPK pathway has been demonstrated to be related to integrin signaling and implicated in epithelial-mesenchymal transition in certain cell lines[18]. TS2 and CD29 antibodies, which promote and inhibit integrin activation, respectively, were used to investigate a possible relationship between integrin signaling and TGFβ-induced generation of TβRI ICD.[19] No major effects on TGFβ-induced formation of the TβRI ICD was observed, when integrins were activated or inhibited. FIG. 21.

Interestingly, results from this study show that the TβRI ICD associates with p300 and the Snail promoter, thereby regulating expression of a subset of genes, including Snail, MMP2, and p300, all of which correlate with increased cell invasiveness.

Nuclear accumulation of TβRI was observed in prostate, breast, and lung cancer cells and also in several cancer tissues, but not in primary prostate epithelial cells. Thus the pathway elucidated in this report occurs in different kinds of human tumors and is observed in human tumours, indicating that it contributes to tumour progression. Taken together, the data disclosed herein demonstrate that the cleavage and nuclear accumulation of TβRI is part of a tumour promoting TGFβ signalling pathway.

References for Example 1

1. J. Groppe, C. S. Hinck, P. Samavarchi-Tehrani, C. Zubieta, J. P. Schuermann, A. B. Taylor, P. M. Schwarz, J. L. Wrana, A. P. Hinck. Cooperative assembly of TGF-beta superfamily signaling complexes is mediated by two disparate mechanisms and distinct modes of receptor binding. *Mol. Cell.* 29, 157-168, (2008).
2. J. Massagué. TGFbeta in Cancer. *Cell* 134, 215-230 (2008).
3. C.-H. Heldin, M. Landstrom, A. Moustakas. Mechanism of TGF-β signaling to growth arrest, apoptosis and epithelial-mesenchymal transition. *Curr. Opin. Cell Biol.* 21, 1-11 (2009).
4. Hayes S, Chawla A, Corvera S. TGF beta receptor internalization into EEA1-enriched early endosomes: role in signaling to Smad2. J. Cell Biol. 2002 Sep. 30; 158(7): 1239-49
5. A. Sorrentino, N. Thakur, S. Grimsby, A. Marcusson, V. von Bulow, N. Schuster, S. Zhang, C. H. Heldin, M. Landstrm. The type I TGF-beta receptor engages TRAF6 to activate TAK1 in a receptor kinase-independent manner. *Nat. Cell Biol.* 10, 1199-1207 (2008).
6. M. Yamashita, K. Fatyol, C. Jin, X Wang, Z Liu, Y. E Zhang. TRAF6 mediates Smad-independent activation of JNK and p38 by TGF-beta. *Mol. Cell.* 31, 918-924, (2008).
7. C. Liu, P. Xu, S. Lamouille, J. Xu, R. Derynck. TACE-mediated ectodomain shedding of the type I TGF-beta receptor downregulates TGF-beta signaling. *Mol. Cell.* 35, 26-36 (2009).
8. A. P. Huovila, A. J. Turner, M. Pelto-Huikko, I. Kärkkäinen, R. M Ortiz. Shedding light on ADAM metalloproteinases. *Trends Biochem. Sci.* 30, 413-422 (2005).
9. S. E. Wang, B. Xiang, M. Guix, M. G. Olivares, J. Parker, C. H. Chung, A. Pandiella, C. L. Arteaga. Transforming growth factor beta engages TACE and ErbB3 to activate phosphatidylinositol-3 kinase/Akt in ErbB2-overexpressing breast cancer and desensitizes cells to trastuzumab. *Mol. Cell. Biol.* 18, 5605-5620 (2008).
10. Jin G, Huang X, Black R, Wolfson M, Rauch C, McGregor H, Ellestad G, Cowling R. A continuous fluorimetric assay for tumor necrosis factor-alpha converting enzyme. Anal Biochem. 2002 Mar. 15; 302(2):269-75.
11. Chow J P, Fujikawa A, Shimizu H, Suzuki R, Noda M. Metalloproteinase- and gamma-secretase-mediated cleavage of protein-tyrosine phosphatase receptor type Z. J Biol. Chem. 2008 Nov. 7; 283(45):30879-89.
12. Y. Feng, G. D. Longmore. The LIM protein Ajuba influences Interleukin-1-Induced NF-kB activation by affecting the assembly and activity of the protein kinase Cz/p62/TRAF6 signaling complex. *Mol and Cell. Biol.* 25, 4010-4022 (2005).
13. J. Moscat, M. T. Diaz-Meco, M. W. Wooten. Of the atypical PKCs, Par-4 and p62: recent understandings of the biology and pathology of a PB1-dominated complex. *Cell Death Differ.* 11, 1426-1437 (2009).
14. D. L. Wheeler, K. J. Ness, T. D. Oberley, A. K. Verma. Protein kinase Cepsilon is linked to 12-O-tetradecanoylphorbol-13-acetate-induced tumor necrosis factor-alpha ectodomain shedding and the development of metastatic squamous cell carcinoma in protein kinase Cepsilon transgenic mice. *Cancer Res.* 63, 6547-6555 (2003).
15. R. Bernardi, A. Papa, P. P. Pandolfi. Regulation of apoptosis by PML and the PML-NBs. *Oncogene* 27, 6299-6312 (2008).
16. J. P. Thiery, H. Acloque, R. Y. Huang, M. A. Nieto. Epithelial-mesenchymal transitions in development and disease. *Cell* 139, 871-890 (2009).
17. Anthis N J, Campbell I D. The tail of integrin activation. Trends Biochem Sci. 2011 Jan. 6.
18. Bhowmick N A, Zent R, Ghiassi M, McDonnell M, Moses H L Integrin beta 1 signaling is necessary for transforming growth factor-beta activation of p38MAPK and epithelial plasticity. J Biol. Chem. 276:46707-46713 (2001).
19. Byron A, Humphries J D, Askari J A, Craig S E, Mould A P, Humphries M J. Anti-integrin monoclonal antibodies. J Cell Sci. 2009 Nov. 15; 122(Pt 22):4009-11.
20. P. Franzen, H. Ichijo, K. Miyazono. Different signals mediate transforming growth factor-beta 1-induced growth inhibition and extracellular matrix production in prostatic carcinoma cells. *Exp. Cell Res.* 207, 1-7 (1993).
21. Castañ ares, C., Redondo-Horcajo, M., Magán-Marchal, N., ten Dijke, P., Lamas, S. and Rodríguez-Pascual, F. Signaling by ALK5 mediates TGF-beta-induced ET-1 expression in endothelial cells: a role for migration and proliferation. *J. Cell Sci.* 120, 1256-1266 (2007).
22. Medici D, Shore E M, Lounev V Y, Kaplan F S, Kalluri R, Olsen B R. Conversion of vascular endothelial cells into multipotent stem-like cells. Nat. Med. 2010 December; 16(12):1400-6. Epub 2010 Nov. 21
23. S. Edlund, S. Bu, N. Schuster, P. Aspenström, R. Heuchel, N. E. Heldin, P. ten Dijke, C. H. Heldin, M. Landstrim. Transforming growth factor-β1 (TGF-β)-induced apoptosis of prostate cancer cells involves Smad7-dependent activation of p38 by TGF-activated kinase 1 and mitogen-activated protein kinase kinase 3. *Mol. Biol. Cell* 2, 529-544 (2003).
24. S. Edlund, S Y Lee, S. Grimsby, S. Zhang, P. Aspenström, C. H. Heldin, M. Landstrim. Interaction between Smad7 and -catenin: importance for transforming growth factor beta-induced apoptosis. *Mol. Cell. Biol.* 4, 1475-1488 (2005).
25. Yakymovych I, Engstrim U, Grimsby S, Heldin C H, Souchelnytskyi S. Inhibition of transforming growth factor-beta signaling by low molecular weight compounds interfering with ATP- or substrate-binding sites of the TGF beta type I receptor kinase. Biochemistry. 2002 Sep. 10; 41(36):11000-7
26. Hayes S, Chawla A, Corvera S. TGF beta receptor internalization into EEA1-enriched early endosomes: role in signaling to Smad2. J. Cell Biol. 2002 Sep. 30; 158(7): 1239-49.

Example 2

Cleavage of TβRI by PS1 Results in Nuclear Translocation of an Intracellular Domain of TβRI Materials and Methods
(i) Cell Culture Human prostate cancer cell line PC-3U, derived from PC-3 cells (Frazen et al, 1993) and LnCap cell line were used in this study. PC-3U cells were cultured in RPMI 1640 medium supplemented with 10% fetal bovine serum (FBS), 1% glutamine and 1% penicillin/streptomycin (Pest). Cells were incubated at 37° C. with 5% $CO_2$. Transient transfection of PC-3U cells was performed using Fugene6 (Roche) following the instructions provided by the manufacturer. Cells were starved for at least 12 hours (12 h) in RPMI 1640 medium supplemented with 1% FBS, 1% glutamine and 1% penicillin/streptomycin. Later the cells were stimulated with 10 ng/ml of TGFβ1.

Wild type and presenilin-1 knock out ($PS1^{-/-}$) mouse embryo fibroblasts (MEFs) and 293T cells were also used in this study. MEF and 293T cells were grown in Dulbecco's modified Eagle's medium (DMEM) supplemented with 10% fetal bovine serum (FBS) and 1% penicillin/streptomycin. Cells were cultivated at 37° C. with 5% $CO_2$. After being starved for at least 12 h in the DEME medium supplemented with 0.5% FBS, the cells were stimulated with 10 ng/ml of TGFβ1.

(ii) Antibodies and Other Reagents

TGFβ1 was obtained from R&D systems.

Antibodies against rabbit phospho-p38, mouse p38, phospho Smad2, rabbit Smad2, rabbit lamin-A, rabbit β-tubulin, rabbit K48 monoclonal antibody were obtained from Cell signaling. Monoclonal anti-β-actin antibody (1:1000) and mouse anti-Flag M2 monoclonal antibody were from Sigma. A rabbit anti-TRAF6 (C-term) antibody was obtained from Zymed laboratories. Rat anti presenilin-1 monoclonal antibody (N-term) was from Millipore. A mouse monoclonal antibody specific to polyubiquitinated Lys63 was from Enzo life sciences. Rabbit anti-HA antibody, rabbit anti-TGFβ receptor I, C-terminal fragment (V22 antibody), and mouse anti-ubiquitin (P4D1) were from Santa Cruz Biotechnology.

Secondary HRP conjugated anti-mouse, anti-rabbit, anti-rat IgG antibodies were from GE Healthcare. Antibodies specific to light chains of rabbit and mouse IgG were from Jackson laboratory. Secondary donkey anti-rabbit antibody (Alexa fluor 555 labeled), goat anti-rabbit antibody (Alexa fluor 488 labeled), donkey anti-mouse antibody (Alexa fluor labeled), and goat anti-rat antibody (Alexa fluor labeled) were from Invitrogen. Pefabloc was from Roche.

(iii) Immunoblotting and In Vivo Protein Interaction Analysis

After being treated with TGFβ for the indicated time periods, cells were washed once with ice-cold PBS and were lysed in ice-cold RIPA lysis buffer (150 mM NaCl, 50 mM Tris, pH 8.0, 1% Triton X 100, 10% (v/v) glycerol, 1 mM aprotinin, 1 mM Pefabloc). Protein concentration in the resultant lysate was measured using the BCA protein assay kit. Equal amount of proteins were used for immunoprecipitations and subjected to electrophoresis on 10%, 12%, 4-12% SDS-polyacrylamide gels, or 7% Tris acetate gels (Invitrogen). Afterwards, the proteins were transferred from the gel to a nitrocellulose membrane using the iBlot machine (Invitrogen).

(iv) siRNA

On-TARGETplus SMARTpool siRNA targeting human Presenilin-1 (PSEN-1) and GENOME non-targeting siRNA #1 were obtained from Dharmacon Research. PC-3U cells were transfected with specific or control siRNA using oligofectamine reagent (Invitrogen) following the protocol provided by the manufacturer.

(v) Plasmids and DNA Transfections

The caTβRI-E161A plasmid construction was described in Sorrentino et al., 2008.[4] A construct for expressing constitutively active TβRI fused with the HA tag at the C-terminal (HA-caTβRI) was from P. ten Dijke (University of Leiden, The Netherlands). Amino acid substitutions were introduced into the HA-caTβRI at positions $V_{129}$ and $I_{130}$, resulting in the TβRI V129A/I130A mutant. A plasmid encoding TβRI with the HA epitope inserted between amino acids 27 and 28 was described in Hayes et al., JCB 2002. HA-tagged wild-type TβRI, K48 mutant, and K63 mutant were from Genentech, San Francisco, Calif. A plasmid expressing myc-tagged PS1 was from Prof. Bart De Strooper.

(vi) Immunofluorescence and Confocal Microscopy

PC-3U cells, grown on coverslips, were starved in 1% FCS for 24 h and stimulated with TGFβ1 for the indicated time periods. Cells were washed once in PBS and then fixed with 4% formaldehyde and then permeabilised with 2% Triton X 100 and later blocked in 5% BSA. Incubations with V22 antibody and antibodies against TRAF6, HA, and PS1 were performed for 1 hr. The cells were then incubated with Alexa 555-labeled or Alexa 488-labeled secondary antibodies. Afterwards, the coverslips were mounted in DAPI according to manufacturer's recommendations. The slides were analyzed with a Zeiss LSM 510 confocal microscope with 63× lens (numerical aperture 1.4). The specificity of primary TRAF6 or TβRI antibodies or secondary antibodies was tested and no background staining was observed.

(vii) Nuclear Cytoplasmic Fractionation Assay

After being treated with TGFβ for the indicated time periods, the cells were washed two times with ice-cold PBS and then lysed in ice-cold PBS. The cells were suspended in PBS and briefly centrifuged. After centrifugation, cell pellets were collected and incubated for 5 min in ice-cold buffer 1 (20 mM Tris HCl pH 7.0, 10 mM KCl, 2 mM $MgCl_2$, 0.5% NP40, 1 mM aprotinin, 1 mM Pefabloc). Afterwards, the cells were sheared mechanically with a syringe and needle and then centrifuged, the supernatant collected (the supernatant is the cytoplasmic protein fraction). The remaining pellet was washed three times with buffer 1, re-suspended in Buffer 2 (Buffer 1+0.5M NaCl), and centrifuged. The supernatant fraction was collected, which is the nuclear protein fraction.

(viii) Ubiquitination Assay

Ubiquitination assays for various proteins were performed following the protocol described in [9].

(viiii) RNA Isolation and RT-PCR

Total RNAs were isolated from cells using an RNeasy mini kit (Qiagen), according to the manufacturer instructions. Two microgram of total RNAs were used for complementary DNA (cDNA) synthesis using the Thermoscript RT PCR system (Invitrogen), following the manufacturer's instructions.

(x) Quantitative Real Time PCR (qRT PCR)

Two microgram of cDNAs, as prepared following the method described in (viiii) above were analyzed in duplicates by real-time PCR (RT-PCR) using the Stratagene system, with SYBR green (Applied Biosystems) to detect the PCR products. Specific primers for TRAF6, PS1 and TβRI were synthesized or purchased from Sigma Aldrich. GAPDH was used as an internal control.

Results (i) TGFβ Regulates PS1 Expression

Figure 9:
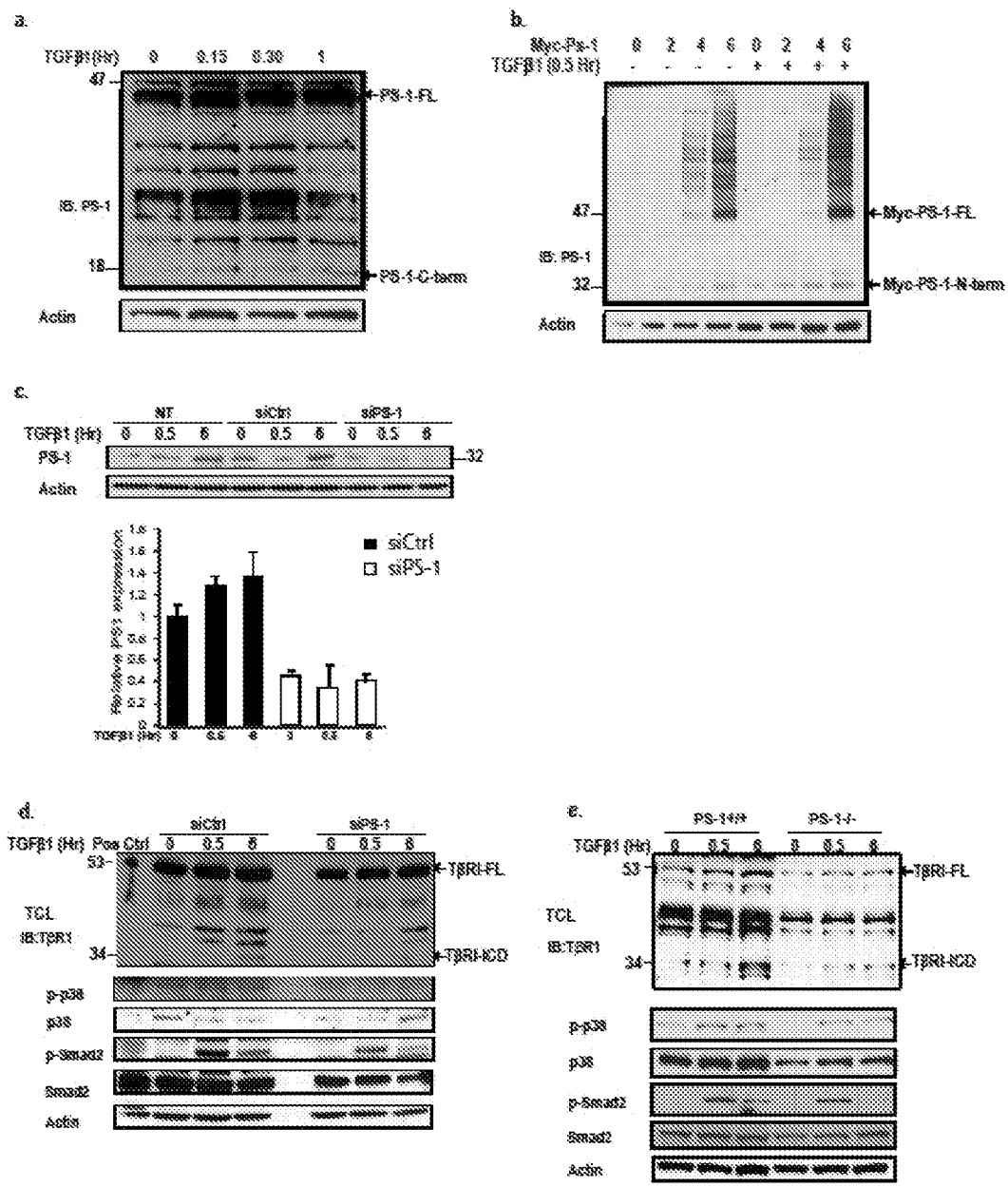
FIG. 9 is a graph showing that TGFβ induces expression and activation of PS1, which promotes cleavage of TβRI in human prostate cancer PC-3U cells. Panel a: Cell lysates derived from PC-3U cells were subjected to immunoblotting with an antibody that recognizes the PS1-holoprotein (PS1-FL; 45 kDa) and the PS1—C-terminal fragment (CTF) (18 kDa). Panel b: Cell lysates from PC-3U cells transiently transfected with Myc-PS1 at various amounts (0, 2, 4, and 6 µg) and treated with TGFβ were subjected to immunoblotting to detect PS1. Panels c and d: Cell lysates derived from PC-3U cells transiently transfected with a PS1 specific siRNA (siPS1) or a non-targeting control siRNA (siCtrl) and treated with TGFβ were subjected to immunoblotting to detect PS1. Non-transfected cells (NT) were used as a blank control in panel c. PS1 mRNA levels, obtained from RT-PCR analyses, are shown in the lower part of panel c. Panel d: Immunoblotting for detecting TβRI, p-p38, p38, p-Smad2 and Smad2 in total cell lysates (TCL) derived from PC-3U cells treated as indicated. Panel e: Cell lysates derived from wild type PS1 (+/+) and PS1 deficient (−/−) mouse embryonic fibroblast (MEFs) treated with TGFβ were subjected to immunoblotting to detect TβRI, p-p38, p38, p-Smad2, and Smad2. Immunoblotting using an anti-β-actin antibody served as an internal control for equal loading of proteins in all lanes in panels d and e.

Presenilins are synthesized as holoproteins, which are endoproteolysed to produce NTF/CTF heterodimers. In order to examine whether TGFβ regulates expression of PS1, PC-3U cells were stimulated with TGFβ for the indicated time periods. Western Blot analyses of lysates derived from the TGFβ1-treated cells was performed using an antibody that recognizes the PS1-holoprotein (45 kDa) or the PS1-C-terminal fragment (CTF) (18 kDa). Endogenous expression of PS1 holoprotein was enhanced upon TGFβ stimulation and a protein band having a molecular weight of 18 kDa, corresponding to PS1 CTF, was observed after TGFβ1 treatment for 0.15 hrs. FIG. 9, panel a; and FIG. 22, panel A. Moreover, overexpression of Myc-PS1 in PC-3U cells at increasing concentrations (0, 2, 4, 6 µg) and treatment of cells with or without TGFβ1 revealed a prominent band of 32 kDa that corresponds to the NTF of PS1. Interestingly, TGFβ1 treatment for 0.5 hrs, enhanced the expression of both full-length PS1 FL and PS1 NTF. FIG. 9, panel b; and FIG. 22, Panel B.

Next, siRNA silencing assay was perform to inhibit PS1 expression in PC-3U cells. Briefly, the cells were transiently transfected with a PS1-targeting siRNA (siPS1) or a non-targeting control siRNA (siCtrl). Non-transfected cells (NT) were used as a blank control. After transfection, the cells were treated with TGFβ1 for indicated time periods. As shown in FIG. 9, panel c; and FIG. 22, panel C. After being treated with TGFβ1 for 0.5 hr or 6 hrs, the cells transfected with the PS1-targeting siRNA showed significantly lower level of PS1 NTF expression as compared to the blank control and to the cells transfected with the control siRNA. Furthermore, RT-PCR analyses of PS1 mRNA expression indicate that TGFβ regulates the expression of PS1 as observed in the cells transfected with the control siRNA but not in the cells transfected with the PS1-targeting siRNA. FIG. 9, panel c; and FIG. 22, panel D. These data indicate that TGFβ regulates the expressions of PS1 holoprotein, PS1 NTF, and PS1 CTF.

(ii) PS1 Cleaves at an Intramembrane Region of TβRI

PS1 functions as the catalytic core of the γ-secretase complex and regulates the intracellular cleavage of various receptors. To examine whether PS1 regulates cleavage of TβRI in PC-3U cells, siCtrl or siPS1 siRNA was transfected to the cells, which was then stimulated with TGFβ1 for 0.5 hr or 6 hrs. Production of a TβRI intracellular domain (ICD, 34 kDa) was observed in the PC-3U cells transfected with the siPS1 siRNA but not in the cells transfected with the control siRNA, indicating that silencing of PS1 expression inhibited the generation of the TβRI ICD fragment. FIG. 9, panel d; and FIG. 22, panel E. However, the expression of TβRI full length (TβRI-FL; 53 kDa) was not affected by silencing of PS1 expression. FIG. 9, panel d; and FIG. 22, panel E. Immunoblotting with specific antisera against p-Smad2, Smad2, phospho-p38, and p38 showed that inhibition of PS1 expression did not affect the level of these proteins, indicating that that cleavage of TβRI does not affect the canonical Smad and p38 signaling. FIG. 9, panel d. Similar results were obtained from mouse embryonic PS1$^{+/+}$ and PS1$^{-/-}$ fibroblasts (MEFs) by immunoblotting assays. FIG. 9, panel e; and FIG. 22, pane F.

PC-3U cells were transiently transfected with PS1 specific siRNA (siPS1), a non-targeting control siRNA (siCtrl), or Myc-PS1 in the presence or absence of TGFβ. Cell lysates derived from the transfected cells were subjected to immunoblotting for PS1. The results shown in FIG. 22, panel G indicate that siPS1 significantly reduced the level of PS1 in the cancer cells.

Figure 22:
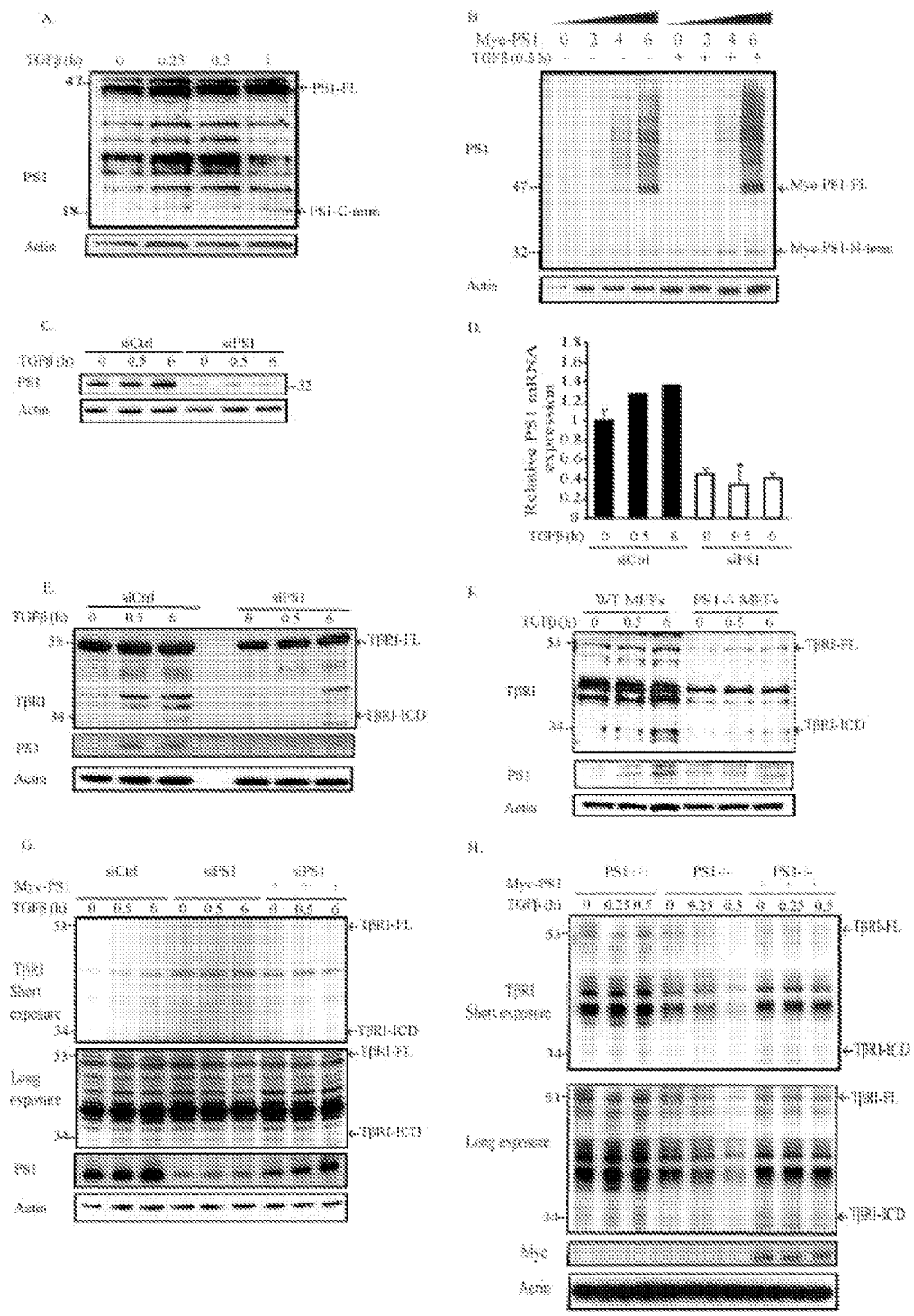
FIG. 22 shows that TGFβ induces expression and activation of PS1 which promotes cleavage of TβRI in human prostate cancer (PC-3U) cells. Panel A: a graph showing levels of PS1-holoprotein (PS1-FL; 45 kDa) and the PS1-C-terminal fragment (CTF) (18 kDa) in cell lysates derived from PC-3U cells by an immunoblotting assay using an antibody that recognizes the PS1-holoprotein. Endogenous expression of PS1-FL was enhanced by TGFβ and PS1 CTF (a band of 18 kDa) was observed after TGFβ treatment for 0.15 h. Panel B: a graph showing levels of PS-1 and the N-terminal fragment of PS1 (PS1-NTF) in cell lysates from PC-3U cells, which were transiently transfected with Myc-PS1 at various amounts (0, 2, 4, 6 µg) in the presence or absence of TGFβ, as determined by an immunoblotting assay. TGFβ was observed to induce expression of both PS1—FL and PS1—NTF, migrating at 32 kDa. Note also the TGFβ-induced increased smear on top of PS1-FL. Panel C: a graph showing levels of PS1, as determined by an immunoblotting assay, in cell lysates derived from PC-3U cells transiently transfected with PS1 specific (siPS1) or non-targeting control siRNA (siCtrl), in the presence or absence of TGFβ. Panel D: a chart showing the levels of PS1 mRNA in the PC-3U cells as described above via RT-PCR analyses. Panel E: a graph showing levels of TβRI and PS1 in PC-3U cells treated as indicated above via immunoblotting. Decrease of TβRI-ICD was observed in cells transfected with siPS1. Panel F: a graph showing levels of TβRI (full-length and ICD) and PS1, determined by immunoblotting, in cell lysates derived from wild type PS1 (+/+) and PS1 deficient (−/−) mouse embryonic fibroblast (MEFs) treated or not treated with TGFβ. Panel G: a graph showing the levels of TβRI (full-length and ICD) and PS1, determined by immunoblotting, in cell lysates derived from PC-3U cells transiently transfected with PS1 specific (siPS1) or a non-targeting control siRNA (siCtrl), or re-transfected with Myc-PS1 in the presence or absence of TGFβ. Panel H: a graph showing the levels of TβRI (full-length and ICD) and PS1 (Myc-tagged), determined by immunoblotting, in cell lysates derived from wild type PS1 (+/+) and PS1 deficient (−/−) MEFs, or re-transfected with Myc-PS1, in the presence or absence of TGFβ. Immunoblotting for β-actin served as internal control for equal loading of proteins in all lanes in A, B, C, E, F and G.

PS1$^{+/+}$ and PS1$^{-/-}$ MEF cells and PS1$^{-/-}$ MEF cells transfected with Myc-PS1 were treated with or without TGFβ; cell lysates were subjected to immunoblotting for TβRI and Myc (PS1). Little TβRI-ICD was observed in cell lysates from PS1$^{-/-}$ MEF cells. FIG. 22, panel H.

(iii) PS1 Interacts with TβRI

Figure 10:
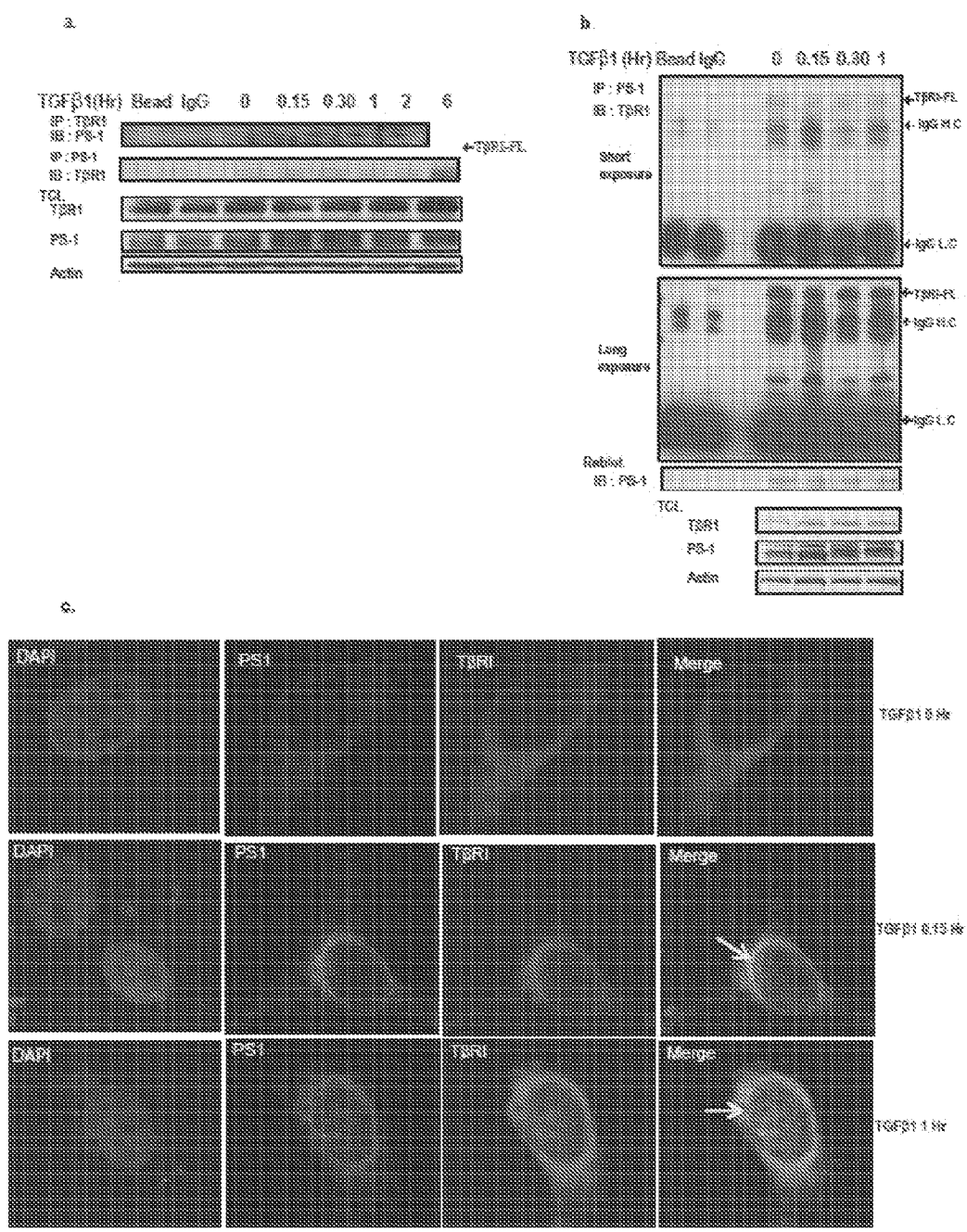
FIG. 10 is a graph showing that endogenous PS1 is associated with TβRI. Panel a: PC-3U was treated with TGFβ and proteins in cell lysates were immunoprecipitated (IP) with an anti-PS1 antibody and immunoblotted with an anti-TβRI antibody. A light-chain specific antibody (IgG L.C.) was used to avoid cross-reaction with the IgG heavy chain. The reverse IP was also conducted. The corresponding total cell lysates (TCL) were immunoblotted with antibodies specific to TβRI and PS1. Panel b: PC-3U cells were stimulated with TGFβ as indicated and the cell lysates were co-immunoprecipitated with the anti-PS1 antibody and immunoblotted with the V22 antibody. An IgG L.C. antibody was used to avoid cross-reaction with the IgG heavy chain. The IP-filter was reblotted with the anti-PS1 antibody to verify the specificity of the PS1 antibody. The TCL-filter was subjected to immunoblotting with antisera against TβRI and PS1. Panel c: PC-3U cells were treated with TGFβ as indicated and subjected to immunofluorescence and confocal imaging. Endogenous PS1 and TβRI was visualised using the anti-PS1 antibody (green) and the V22 antibody (red). Staining with DAPI (blue) was used to visualise cell nuclei (blue, bottom panels). Arrow indicates co-localization of the proteins.

First, subconfluent PC-3U cells were starved and stimulated with TGFβ1 for various time periods as indicated in FIG. 10, panel a. Proteins in the treated cells were immunoprecipitated using an antibody specific to the NTF of PS1 and then immunoblotted using antibody V22 (recognizing the C-terminal fragment of TβRI). As shown in FIG. 10, panel a, both endogenous PS1 and TβRI were precipitated by the anti-PS1 antibody, indicating that these two proteins form a protein complex. Interaction between PS1 and TβRI was confirmed in an co-immunoprecipitation using antibody V22 for immunoprecipitation and the anti-PS1 antibody for immunoblotting. FIG. 10, panel a.

In a further immunoprecipitation assay, a PS1 antibody that recognizes the PS1 holoprotein was used for immunoprecipitation and antibody V22 was used for immunoblotting. As shown in FIG. 10, panel b, PS1 and TβRI were coimmuprecipitated from cell lysates of both untreated PC-3U cells and PC-3U cells stimulated TGFβ1 for various time periods as shown in FIG. 10, pane b.

Co-immunofluorescence and confocal imaging assay was performed to examine subcellular localization of PS1 and TβRI in PC-3U cells treated or not treated with TGFβ1. As shown in FIG. 10, panel c, TGFβ stimulation enhanced co-localization of PS1 and TβRI in the cells.

Taken together, the data shown above demonstrate that PS1 interacts with TβRI in vivo.

(iii) TGFβ Promotes Lys63-Linked Polyubiquitination of PS1 N-Term

Figure 11:
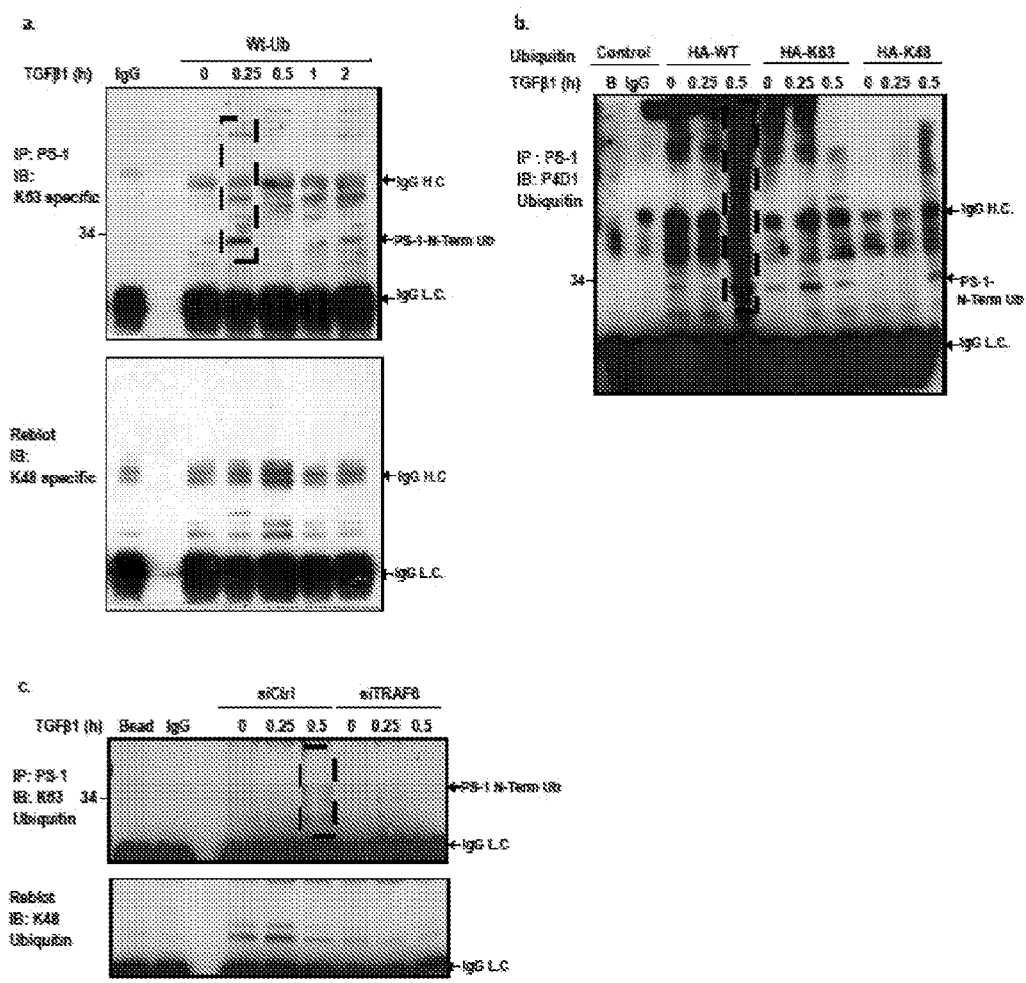
FIG. 11 is a graph showing that TGFβ promotes Lys63-dependent polyubiquitination of PS1 in in vivo ubiquitination assays. Panel a: PC-3U cells were treated with TGFβ. Ubiquitination of PS1 were examined with an in vivo ubiquitination assay as described in Sorrentino et al., 2008. Panel b: In vivo ubiquitination assays were performed in PC-3U cells transiently transfected with HA-tagged wt ubiquitin and the K63 or K48 mutant. Cell lysates were immunoprecipitated with an anti-PS1 antibody. Polyubiquitination was visualised by probing immunoblots with P4D1-antisera. An IgG L.C. antibody was used to avoid cross-reaction with the IgG heavy chain. Panel c: PC-3U cells were transiently transfected with a control siRNA or an anti-TRAF6 siRNA to silence the endogenous TRAF6. The cells were treated with TGFβ. The ubiquitination of PS1 was examined by an in vivo ubiquitination assay as described above.

An in vivo ubiquitination assay was performed in PC-3U cells treated with TGFβ at various time points (i.e., 0, 0.25, 0.5, 1, and 2 hr after TGFβ1 treatment) so as to investigate the mechanism of TGFβ mediated activation of PS1. Cell lysates from the treated cells were heated in the presence of 1% SDS to disrupt non-covalent protein-protein interactions and then diluted with a lysis buffer (1:10). PS1 NTF was immunoprecipitated and analyzed by immunoblotting using an antiserum specific to K63-linked ubiquitins in TβRI. The results indicate that PS1 NTF showed K63 ubiquitination 0.15 hr after TGFβ1 treatment. FIG. 11, panel a. No K48 ubiquitination of PS1 NTF was observed using an antibody specific to K48-linked ubiquitins. The same results were observed in 293T cells.

To confirm the finding that PS1 is ubiquitinated in K63-dependent manner, PC-3U cells were transfected with either wild type ubiquitin or the K63 or K48 ubiquitin mutants described in Example 1 above. As shown in FIG. 11, panel b. TGFβ induced a K63-linked polyubiquitination in PS1, which resulted in PS1 activation.

(iv) TGFβ Promotes TRAF6 Dependent K63 Ubiquitination of PS1 N-Term

Previous reports suggest that PS1 interacts with TRAF6 in a nerve growth factor (NGF) dependent manner, leading to enhanced autoubiquitination of TRAF6. RNA silencing analysis was performed to investigate whether TRAF6 is the E3 ligase that ubiquitinates PS1. PC-3U cells were transfected with a siRNA targeting TRAF6 (siTRAF6). After being treated with TGF-β1, the transfected cells were subjected to an in vivo ubiquitination assays. PS1 NTF was immunoprecipitated and analyzed using an antiserum specific to K63 linked ubiquitin. The result indicates that PS1 underwent K63 linked ubiquitination in cells transfected with siCtrl and treated with TGFβ1 for 0.30 hr. The K63 linked ubiquitination was not observed in cells transfected with siTRAF6. These results demonstrate that TRAF6 is the E3 ligase involved in the ubiquitination of PS1-FL and PS1 NTF.

(v) PS1 Interacts with TRAF6 at the RING Domain

Figure 12:
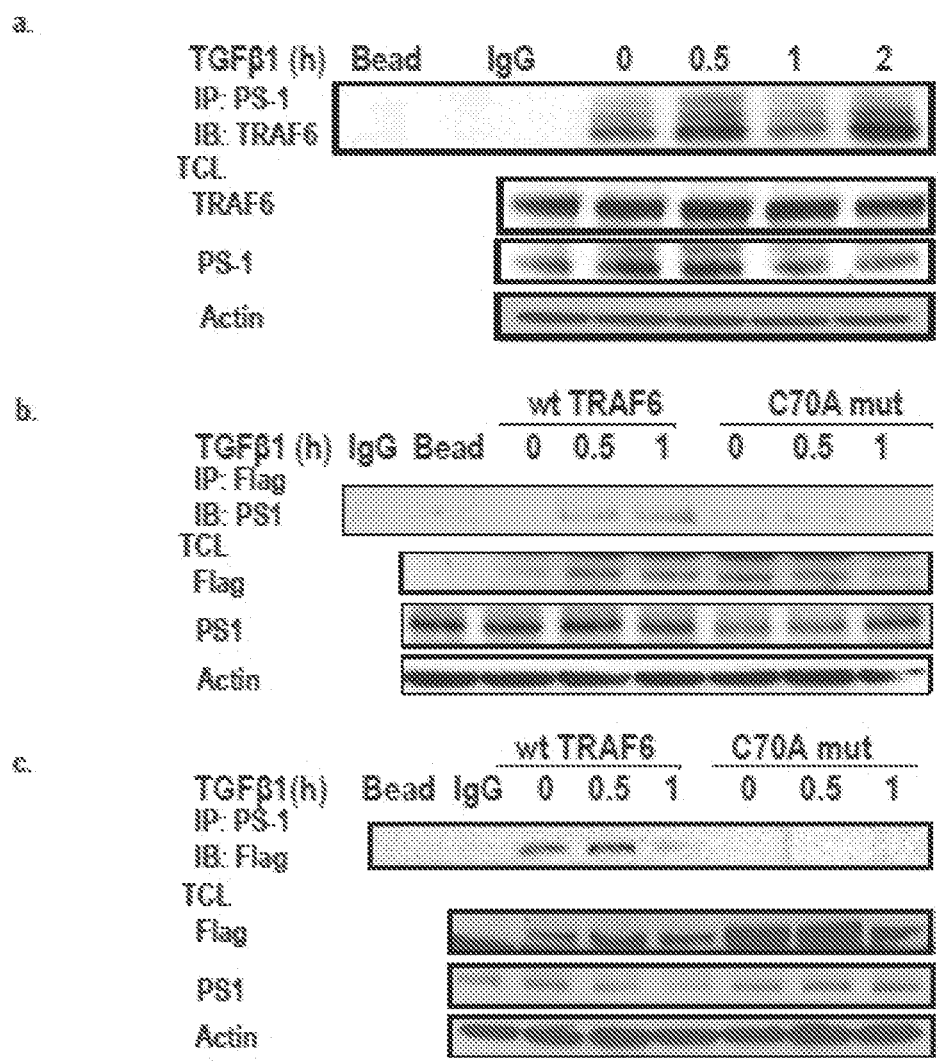
FIG. 12 is graph showing that the association between TRAF6 and PS1 is dependent on the catalytic activity of TRAF6. Panel a: PC-3U cells were treated with or without TGFβ. Proteins were immunoprecipitated (IP) with an antibody specific to the N-terminus of PS1 and immunoblotted with an antibody specific to TRAF6. A light-chain specific antibody (IgG L.C.) was used to avoid cross-reaction with the IgG heavy chain. The corresponding total cell lysates were immunoblotted with antibodies specific to TRAF6 and PS1. The level of β-Actin served as an internal control for equal loading of proteins. Panel b: PC-3U cells were transiently transfected with Flag-tagged wild type (wt) or C70A mutant TRAF6 and treated with TGFβ. Proteins were immunoprecipitated (IP) with an anti-Flag antibody and immunoblotted with an anti-PS1 antibody. A light-chain specific antibody (IgG L.C.) was used to avoid cross-reaction with the IgG heavy chain. The corresponding total cell lysates were immunoblotted with antibodies specific to Flag (TRAF6) and PS1. The level of β-Actin served as an internal control for equal loading of proteins. Panel c: PC-3U cells were transiently transfected with Flag-tagged wild type (wt) or C70A mutant TRAF6 and treated with TGFβ. Proteins were immunoprecipitated (IP) with an anti-PS1 antibody and immunoblotted with antibodies specific to Flag. A light-chain specific antibody (IgG L.C.) was used to avoid cross-reaction with the IgG heavy chain. The corresponding total cell lysates were immunoblotted with antibodies specific for Flag (TRAF6) and PS1. The level of β-Actin served as an internal control for equal loading of proteins.

In line with the previous finding that NGF mediates TRAF6 and PS1 interaction [23], PC-3U cells were stimulated with TGFβ1 and co-immunoprecipitation experiments were performed by immunoprecipitating with an anti-PS1 NTF antibody and immunoblotted with an anti-TRAF6 antisera. As shown in FIG. 12, panel a, endogenous PS1 interacts with TRAF6, the interaction being enhanced by TGFβ. To examine the binding domain in TRAF6 for interaction with PS1, PC3-U cells were transfected with wild-type TRAF6 (Flag tagged) or with TRAF6 C70A mutant, which is deficient in the E3-ligase activity. Cell lysates where subjected to immunoprecipitation with the anti-PS1 NTF antibody and immunoblotted with an anti-Flag antibody to detect association between TRAF6 and PS1 NTF. As shown in FIG. 12, panel b, only wild-type TRAF6 interacted with endogenous PS1, while the TRAF6 C70A mutant did not, indicating that the E3 ligase activity of TRAF6 is required for its interaction and ubiquitination of PS1. Moreover, the interaction between TRAF6 and PS1 was enhanced by TGFβ stimulation. Deletion of the highly conserved RING domain at the N-Terminus of TRAF6 resulted in inhibition of the interaction.

(vi) TRAF6 Mediates Cleavage of TβRI Through PS1

Figure 13:
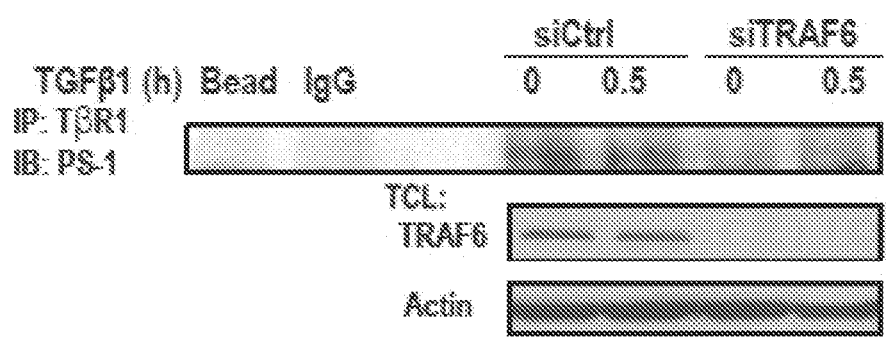
FIG. 13 is a graph showing that TRAF6 is required for the association between TβRI and PS1. Panel a: PC-3U cells were transiently transfected with a control siRNA (siCtrl) or an anti-TRAF6 siRNA (siTRAF6) to silence the endogenous TRAF6. The cells were treated with TGFβ. Proteins were immunoprecipitated (IP) with an anti-TβRI antibody and immunoblotted with an anti-PS1 antibody. A light-chain specific antibody (IgG L.C.) was used to avoid cross-reaction with the IgG heavy chain. The corresponding total cell lysates were immunoblotted with an antibody specific to TRAF6. The level of β-Actin served as an internal control for equal loading of proteins. Panel b: PC-3U cells were transiently transfected with HA-tagged constitutively active (ca) TβRI or the E161A mutant TβRI and treated with TGFβ. Proteins were immunoprecipitated (IP) with an anti-PS1 antibody and immunoblotted with antibodies specific to HA. A light-chain specific antibody (IgG L.C.) was used to avoid cross-reaction with the IgG heavy chain. The corresponding total cell lysates were immunoblotted with antibodies specific to HA (TβRI) and PS1. The level of β-Actin served as an internal control for equal loading of proteins.
Figure 13:
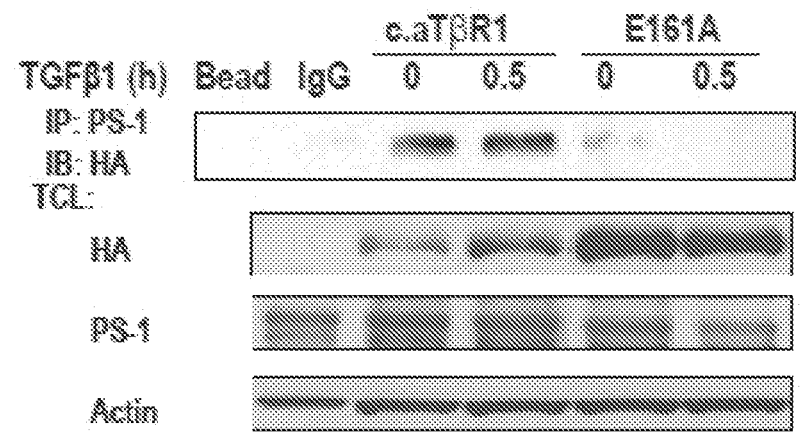

The expression of TRAF6 was silenced by the siTRAF6 siRNA in PC-3U cells to explore whether TRAF6 acts a central mediator in facilitating the interaction between TβRI and PS1. Proteins obtained from the cells transfected with the siRNA were subjected to co-immunoprecipitation to examine whether endogenous TβRI interacts with PS1 when TRAF6 was knocked out. No association of TβRI and PS1 was observed in the TRAF6-knocked out cells, indicating that TRAF6 is required for the interaction between TβRI and PS1. FIG. 13, panel a.

PC-3U cells were transfected with either the wild-type TβRI or the TβRI E161A mutant, which does not bind to TRAF6. Sorrentino et al., 2008. Cell lysates from the transfected cells were subjected to co-immunoprecipitation to examine association between TβRI and PS1 in the transfected cells. As shown in FIG. 13, panel b, the wild-type TβRI, but not the E161A mutant, interacts with PS1.

In sum, the data disclosed above indicates that TRAF6 is a crucial factor in TβRI/PS1 interaction. It plays a major role in recruiting PS1 to interact with TβRI, leading to the cleavage of TβRI and generation of a TβRI ICD.

(vii) Mutation in TβRI Transmembrane Region Inhibits the Cleavage by PS1

Figure 14:
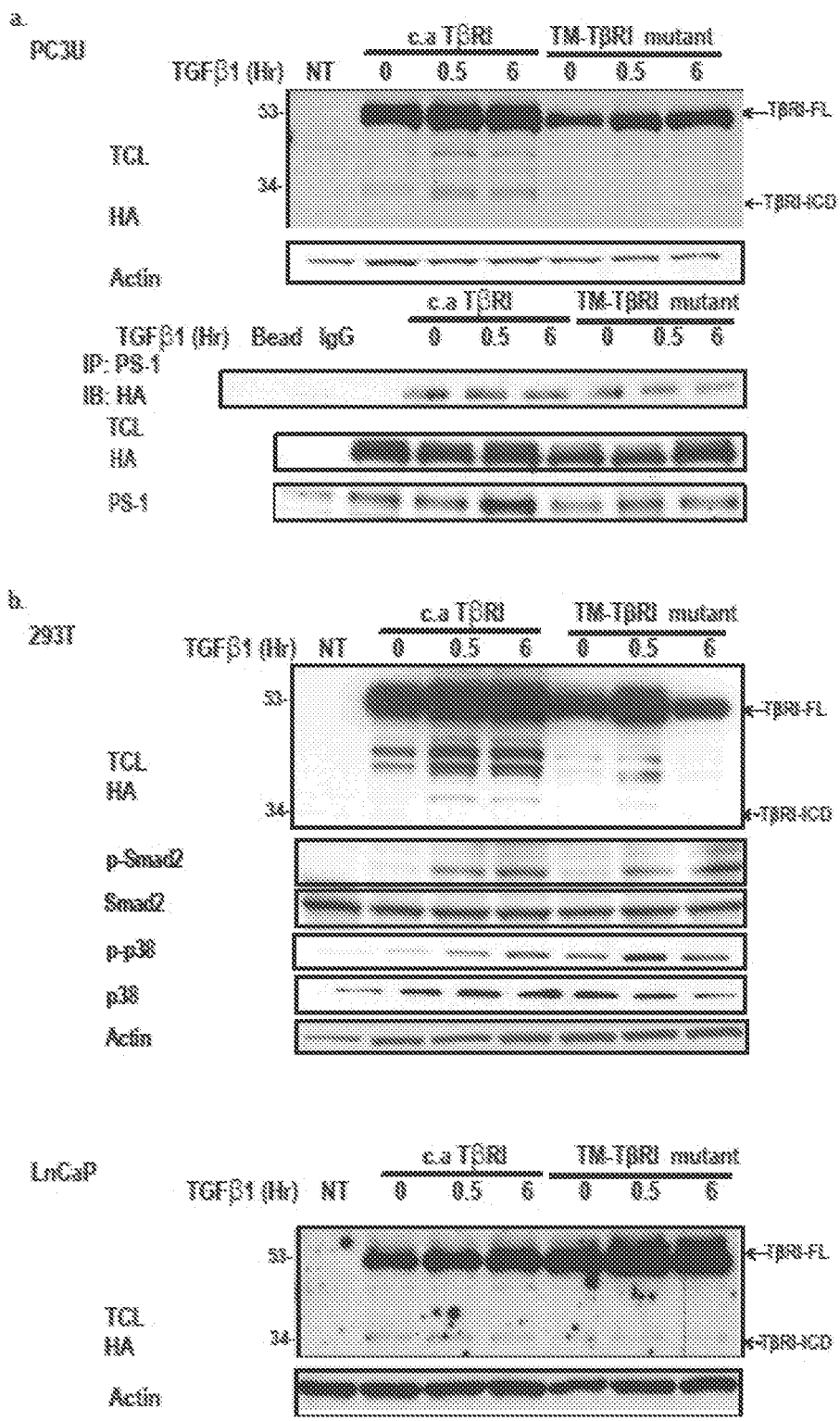
FIG. 14 is a graph showing the identification of the PS1 cleavage site in TβRI. Panel a: PC-3U cells were transiently transfected with HA-tagged constitutively active (ca) or the V129A/I130A TβRI mutant and treated with TGFβ. Non transfected cells (NT) served as a blank control. A fraction of the proteins was extracted from the total cell lysate and immunoblotted with an anti-HA antibody (TβRI). The level of β-Actin served as an internal control for equal loading of proteins. Another fraction of proteins derived from the total cell lysate was immunoprecipitated (IP) with an anti-PS1 antibody and immunoblotted with an antibody specific to HA to investigate the association of PS1 to the ectopically expressed TβRI. A light-chain specific antibody (IgG L.C.) was used to avoid cross-reaction with the IgG heavy chain. Panel b: 293T cells were transiently transfected with HA-tagged constitutively active (ca) or the V129A/I130A TβRI mutant and treated with TGFβ. Total cell lysates (TCL) were subjected to immunoblotting with the anti-HA antibody (TβRI). The importance of TGFβ-induced cleavage of TβRI in activating the Smad2 and p38 pathways was examined by immunoblotting of TCL to detect p-Smad2/Smad2 and p-p38/p38. The level of β-Actin served as an internal control for equal loading of proteins. Panel c: PC-3U cells were transiently transfected with HA-tagged constitutively active (ca) or the V129A/I130A TβRI mutant and treated with TGFβ as indicated. The cells were then subjected to immuno-fluorescence and confocal imaging. HA-tagged constitutively active (ca) and the mutant TβRI were detected using the anti-HA antibody (red). Staining with DAPI (blue) was used to visualise cell nuclei. Panel d: a chart showing the level of TβRI ICD that binds to TβRI promoter as obtained in a ChIP assays.
Figure 14:
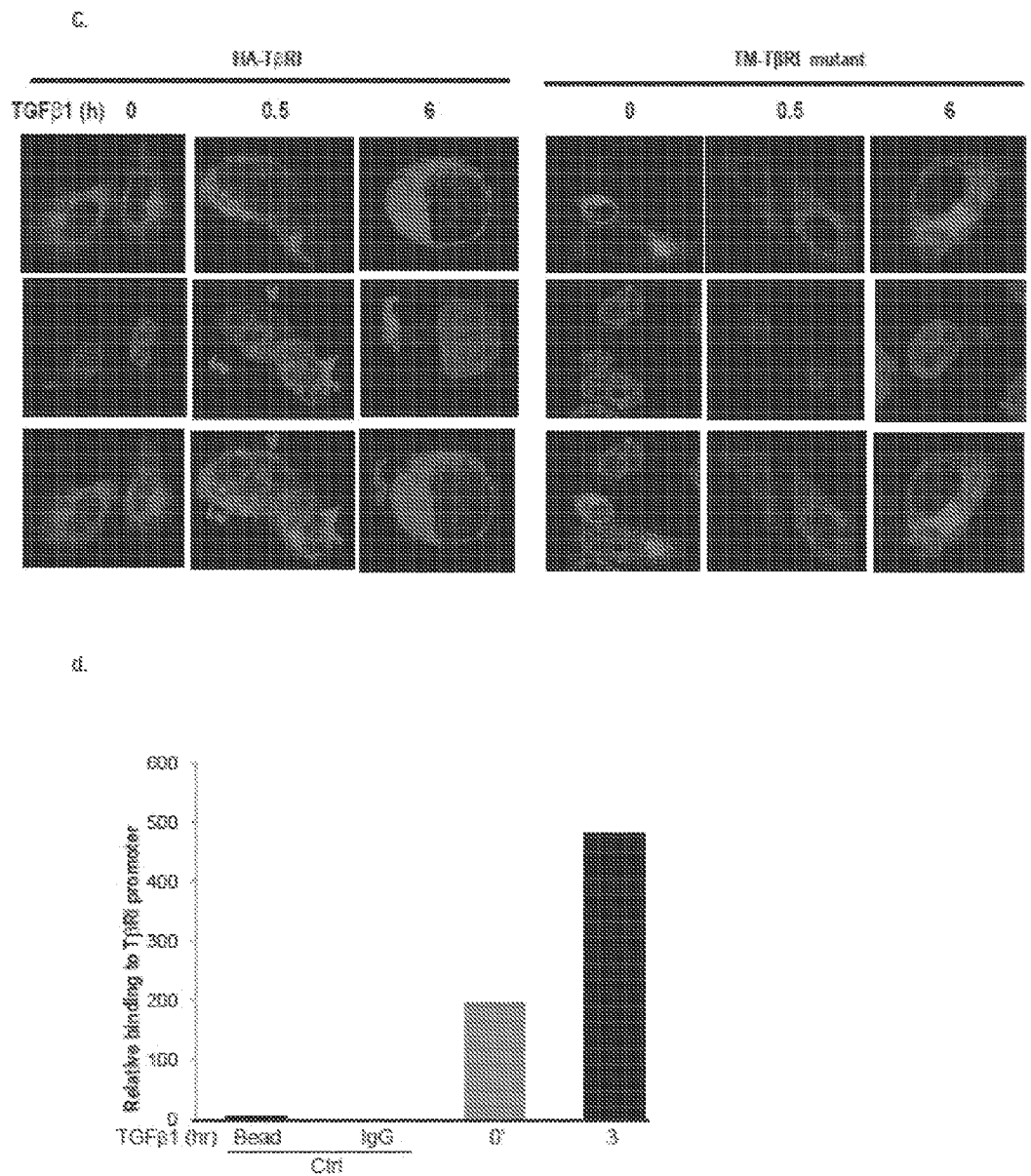
Figure 23:
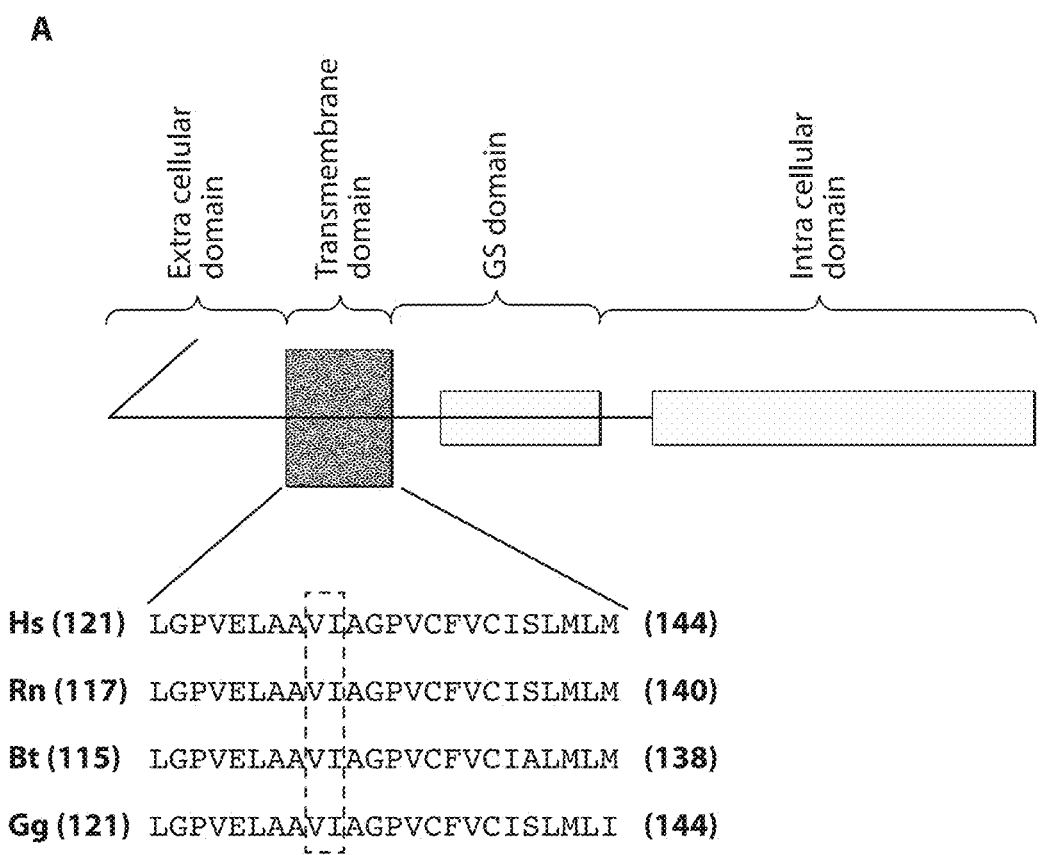
FIG. 23 shows Identification of the PS1 cleavage site in TβRI. Panel A: a schematic illustration showing in silico identification of a cleavage site for PS1 in the transmembrane domain of TβRI. Panel B: a graph showing levels of various proteins in PC-3U cells transiently transfected with HA-tagged constitutively (ca) active or TM-mutant TβRI in the presence or absence of TGFβ, as determined by an HA-specific antibody or antibodies specific to p-Smad2, Smad2, p-p38, p38, and actin. Non-transfected cells (NT) served as control for HA-blots. A fraction of the proteins was extracted as total cell lysates and immunoblotted with antibodies specific for HA (TβRI) (upper panel). Actin served as an internal control for equal loading of proteins. Another fraction of proteins was immunoprecipitated (IP) with anti-PS1 antibodies and immunoblotted with antibodies specific for HA to investigate the association between PS1 and ectopically expressed TβRI. A light-chain specific antibody (IgG L.C.) was used to avoid cross-reaction with the IgG heavy chain. See the bottom panel. Panel C: a photo showing the levels of various proteins in 293T cells transiently transfected and treated as indicated above. Total cell lysates (TCL) were subjected to immunoblotting with HA-specific antibodies specific to detect HA-tagged TβRI (upper panel). TGFβ-induced formation of TβRI-ICD was reduced in cells transfected with the TM-TβRI mutant. The importance of TGFβ-induced cleavage of TβRI for activation of Smad2 and p38 pathways was examined by immunoblotting of TCL to detect the levels of p-Smad2/Smad2 and p-p38/p38. Actin served as an internal control for equal loading of proteins. Panel D: a photo showing presence of TβRI in PC-3U cells transfected and treated as indicated above. The cells were then subjected to immuno-fluorescence and confocal imaging. HA-tagged constitutively active (ca) and mutant TβRI were visualised with HA-antibodies (red). Staining with DAPI (blue) was used to visualize cell nuclei. Panel E: a chart showing the levels of TβRI in PC-3U cells transiently transfected and treated as indicated above via qRT-PCR analysis. Panel F: a chart showing the levels of promoter-binding TβRI in PC-3U cells treated or not treated with TGFβ via a chromatin immunoprecipitation assay, using V22 antibody against the endogenous TβRI. Panel G: a graph showing cell invasion levels of PC-3U cells transfected and treated as indicated above by an invasion assay as described herein. Cells were visualized by staining with crystal violet cell stain solution (left panel). The right panel presents mean values for optical density (OD) of invasive cells. *P<0.05, **P<0.005 and P<0.001(ANOVA).
Figure 23:
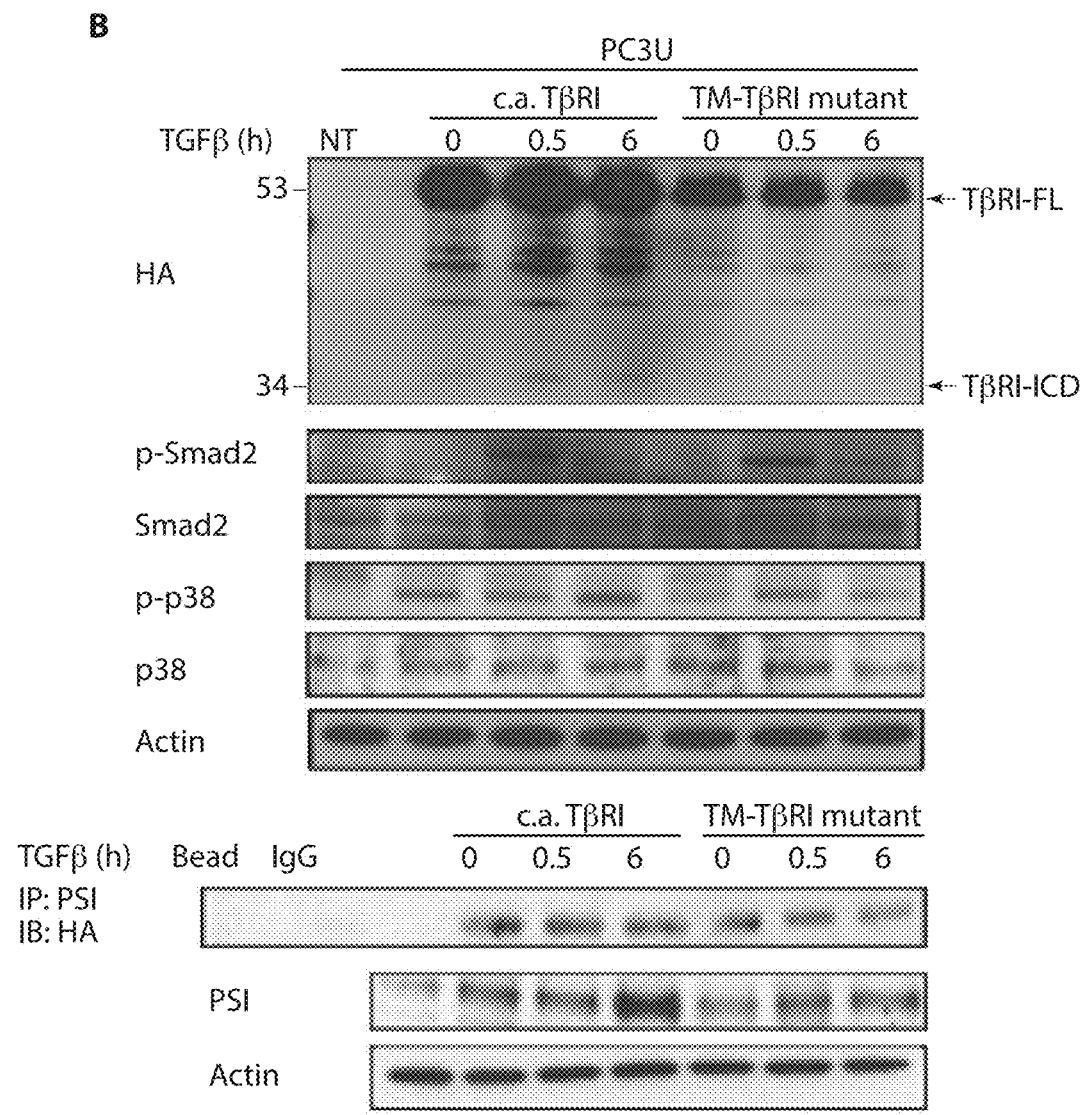
Figure 23:
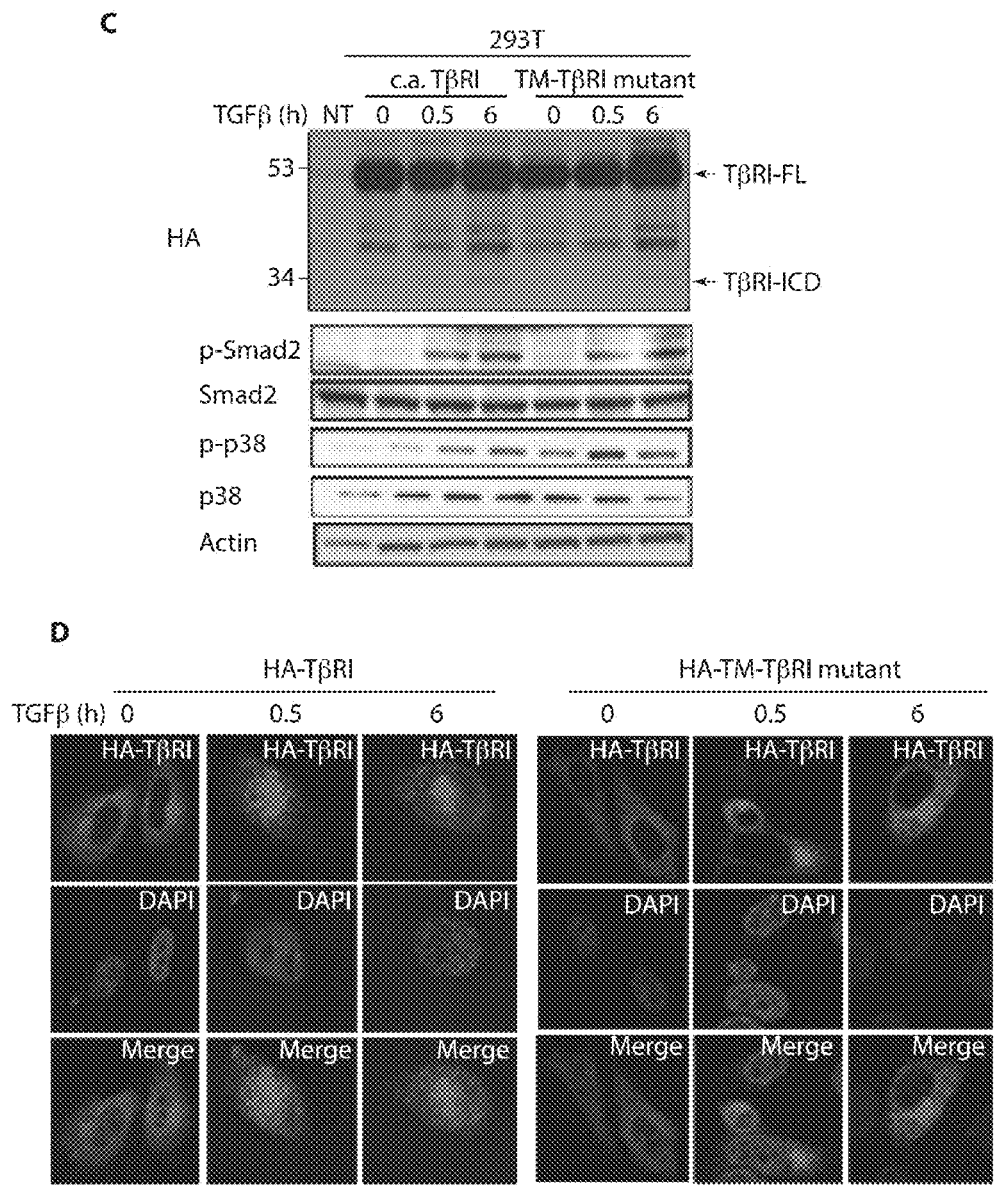
Figure 23:
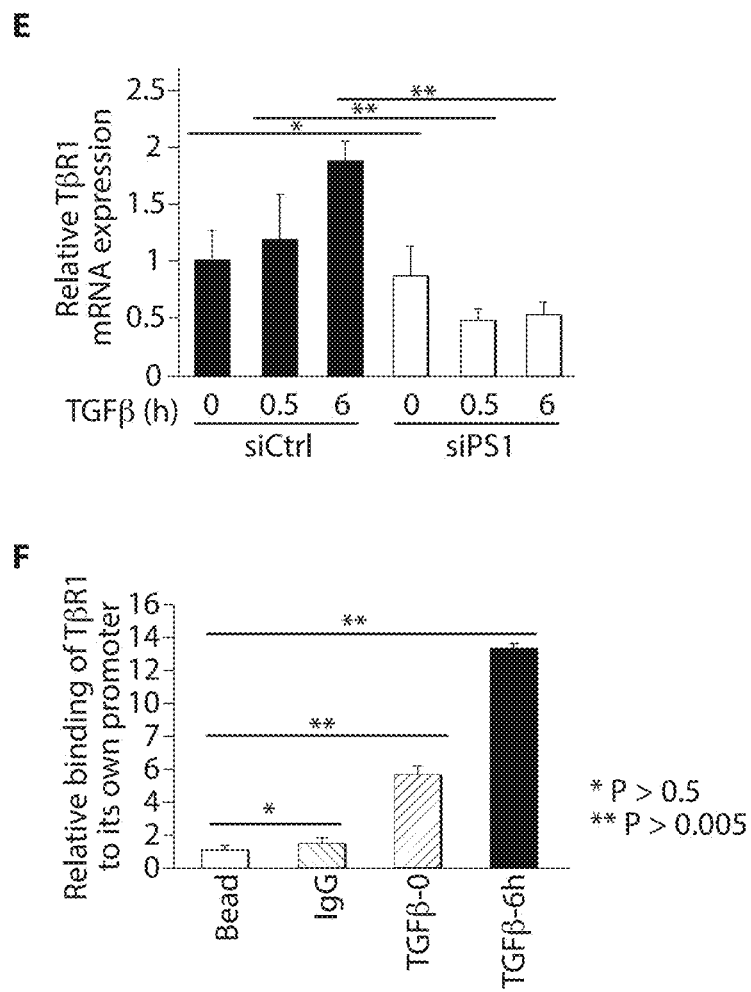
Figure 23:
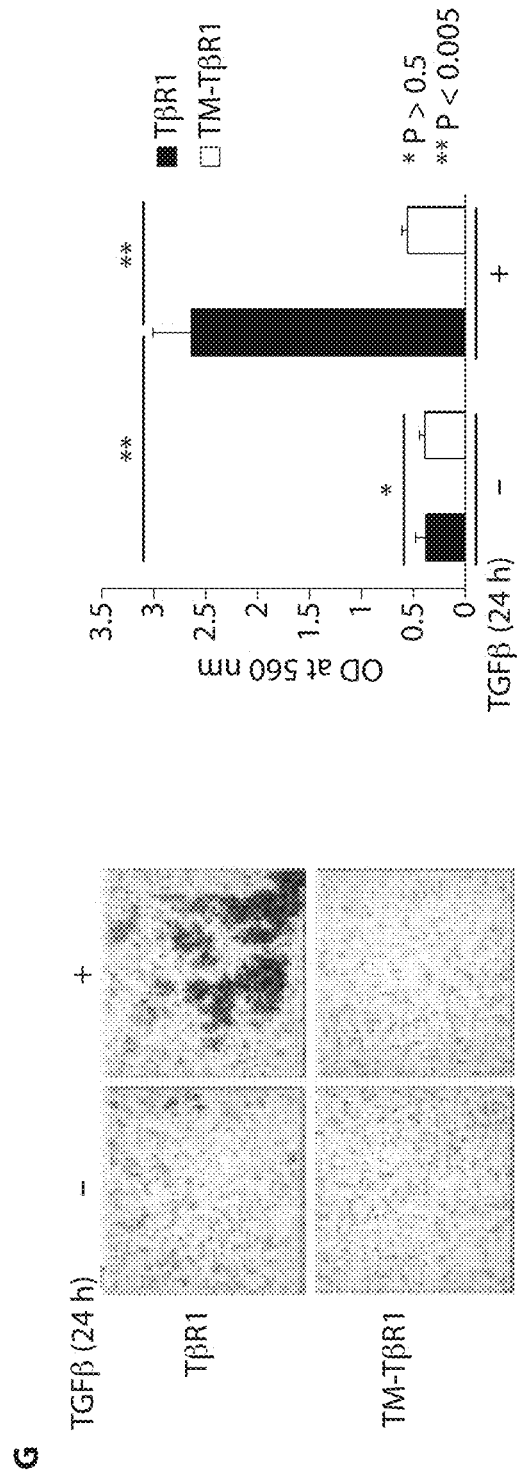

FIG. 23, panel A shows in silico identification of a cleavage site for PS1 in the transmembrane domain of TβRI. It appears that the $V_{129}$-$I_{130}$ in the transmembrane domain of TβRI constitute a possible consensus motif for PS1 cleavage. To verify this, a TM-V129A/I130A double mutant of TβRI was constructed. Constructs expressing caTβRI and the TM-V129A/I130A TβRI mutant were introduced into PC-3U cells and production of TβRI ICD was examined before and after TGFβ stimulation. Production of TβRI ICD was observed only in the TGFβ-treated cells transfected with caTβRI construct, indicating that mutations at the $V_{129}$-$I_{130}$ motif suppressed cleavage of TβRI. FIG. 14, panel a; and FIG. 23, panel B.

Co-immunoprecipitation analysis was performed to examine the interaction between PS1 with caTβRI and the TM-V129A/I130A TβRI mutant. As shown in FIG. 14, panel b, endogenous PS1 interacts with both caTβRI and the mutant.

Finally, the effect of the TM-V129A/I130A TβRI mutant on the TGFβ mediated Smad- and non-Smad (p38) signaling was examined. Neither of these pathways was found to be affected by the cleavage of the TβRI. FIG. 23, panel B. Similar results were observed in 293T cells. FIG. 14, panel b; and FIG. 23, panel C.

Immunofluorescence analysis was performed to examine whether the TM-V129A/I130A TβRI mutant, which is not cleaved by PS1, affects the nuclear translocation of TβRI ICD. The TβRI KD mutant described in Example 1 above and the TM-V129A/I130A TβRI mutant, both being HA-tagged, were transiently transfected into PC-3U cells, which were then treated with TGFβ1 for different time periods (see FIG. 14, panel c). The subcellular localization of both mutants were observed by anti-HA antisera staining and confocal microscopy. As shown in FIG. 14, panel c, and FIG. 23, panel D, nuclear localization of TβRI was only observed in cells transfected with the TβRI KD mutant (after being treated by TGFβ1 for 0.5 or 6 hrs) but not in the cells transfected with the TM-V129A/I130A TβRI mutant. Moreover TGFβ1 treatment enhanced TβRI ICD nuclear translocation, whereas this did not occur in the cells transfected with the TM-V129A/I130A TβRI mutant.

In order to further substantiate the finding that the TM-V129A/I130A TβRI mutant does not translocate to the nuclei, nuclear-cytoplasmic fractionation assays were performed. Data from these assays indicate that only the KD mutant translocated to the nuclei, whereas the TM-V129A/I130A TβRI mutant did not.

qRT-PCR analysis was performed to determine the expression levels of TβRI using mRNAs extracted from PC-3U cells, which were transiently transfected with siCtrl and siPS-1 and treated with TGFβ at various dosages. siPS-1 significantly reduced the level of TβRI as shown in FIG. 23, panel E. Next, chromatin immunoprecipitation assay was performed to detect binding of TβRI to its own promoter, using V22 antibody against the endogenous TβRI in PC-3U cells treated or not with TGFβ. As shown in FIG. 23, panel F, TGFβ significantly increased the level of promoter-bound TβRI. Further, PC-3U cells transiently transfected and treated as indicated in FIG. 23, panel G were subjected to an invasion assay as described above. A much higher level of cancer cell invasion was observed in the presence of TGFβ, which was associated with a higher level of cleaved TβRI. FIG. 23, panel G.

Taken together, the data discussed above demonstrate that mutation of the VI motif to AA inhibits the cleavage of TβRI by PS1, thereby inhibiting TβRI ICD nuclear translocation.

(viii) TβRI Promotes its Own Expression

ChIP assays were performed to investigate whether generation of TβRI ICD and its nuclear translocation promote TβRI expression. The result thus obtained shows that TβRI ICD associates with the promoter of the TβRI gene, thereby up-regulating its expression. FIG. 14, panel d.

Discussion

Presenilin1 (PS1) is a polytransmembrane protein that plays an integral role as catalytic subunit of the γ-secretase complex [12, 13]. The γ-secretase complex cleave various transmembrane receptors, including like Notch receptor, N/E-Cadherin, IL-1, the neurotrophin receptor p75. [14] The inactive PS1 holoprotein (42-43 kDa) undergoes endoproteolytic cleavage by an unknown presenilinase to generate an N-terminal (NTF, 27-28 kDa) and a C-terminal fragment (CTF, 16-17 kDa). [15] PS1 is localized in the endoplamic reticulum (ER), golgi apparatus, ER/Golgi intermediate compartments, endosomes, lysosomes, phagosomes, plasma membrane, and mitochondria. [16-18] The structure of PS1 has been highly debated according to different studies. The recent model proposes PS1 to exist as a nine transmembrane (TM) protein with the cytosolic N-terminal region spanning the first six hydrophobic regions (I-VI TM), a cytosolic loop domain (VII TM) and the C-terminal region spanning three TMDs (VIII-IX TM) localized in the lumen/extracellular space. [19, 20] The association of PS1 with nicastrin, presenilin enhancer 2 (pen-2), and the anterior pharynx defective1 (aph-1) proteins, leads to an active γ-secretase complex. [21] Previous reports suggest that PS1 has a conserved TRAF6 binding motif and its association with TRAF6 leads to enhanced TRAF6 autoubiquitination and thereby promotes ubiquitination of p75 neurotrophin receptor (p75$^{NTR}$). Powell et al, 2009.

As disclosed herein, TRAF6 ubiquitinates TβRI in Lys63-dependent manner, leading to its cleavage at the ectodomain region by TACE. This ectodomain shedding leads to generation of an ICD, which translocates to the nuclei and binds to the transcriptional co-activator p300, thereby regulating the expression of certain TGFβ target genes such as Snail-1. It was known in the art that such genes are involved in cancer cell invasion. It is further disclosed herein that TGFβ regulates PS1 expression, leading to the activation of PS1 by K63 linked polyubiquitination. The activated PS1 in turn leads to cleavage of the TβRI at the transmembrane region in a TGFβ-dependent manner, thereby generating an ICD (34 kDa). This ICD fragment was found to accumulate in nuclei, leading to upregulation of TβRI expression. TRAF6 is the E3 ligase that ubiquitinates PS1 in a Lys63-dependent manner. In addition, TRAF6 is required for the interaction between TβRI and PS1.

As disclosed above, TβRI co-immunoprecipitated with PS1 and this interaction is constitutive and that TGFβ1 treatment enhanced the interaction. TβRI was found to interact with PS1 holoprotein and also with PS1-NTF. These data suggest that TβRI interaction with PS1 is a constitutive interaction. Moreover, overexpression of HA-TβRI and Myc-PS1 and analyses of their subcellular localization by confocal imaging revealed that TβRI and PS1 in deed co-localize and that TGFβ1 treatment enhances their co-localization.

TRAF6 was initially identified for its role as an adaptor protein to activate NF-κB signaling by IL-1[24]. TRAF6 is classified as an E3 ligase as it interacts with the E2 conjugating enzyme (E2) Msm2 and thereby mediates K63 ubiquitination of various proteins. The carboxyl TRAF-domain plays an important role in mediating interaction with various proteins or polyubiquitination of various proteins.

Previously, it was reported that NGF mediates TRAF6 interaction with PS1 and PS1 has a consensus TRAF6-binding motif which leads to enhanced ubiquitination of TRAF6 upon NGF mediated stimulation of p75$^{NTR}$. [23] The disclosure herein that PS1 interacts with TRAF6 at its RING domain is crucial as it leads to ubiquitination of PS1 in a TGFβ-dependent manner. In line with the previous report, the disclosure herein shows that there is constitutive interaction between endogenous PS1 and TRAF6, while TGF-β stimulation enhances the interaction at. Transient transfection of wt TRAF6 and the E3-ligase deficient C70A mutant and co-immunoprecipitation experiments revealed that PS1 interacts with TRAF6 at the RING domain, as the interaction was not observed with the E3 ligase deficient C70A mutant. Moreover, the results herein also demonstrate that TRAF6 ubiquitinates PS1 in a K63 dependent manner as in vivo ubiquitination assays with an anti-PS1 NTF antibody revealed that PS1 ubiquitination was observed only in siCtrl but not in siTRAF6. This indicates that TRAF6 is the E3 ligase that ubiquitinates PS1. Moreover, a time course of in vivo ubiquitination assays revealed that PS1 NTF is ubiquitinated upon TGFβ1 treatment for 0.15 hrs in a K63 dependent manner, while no significant sign of K48 ubiquitination was observed. This result was confirmed in cells transfected with wild type ubiquitin and the K63 and K48 mutants. Together, the data disclosed herein indicate that PS1 NTF is ubiquitinated in a K63 dependent manner by TRAF6, which is mediated by TGFβ.

It was known that TRAF6 interacts with TβRI at a highly conserved motif, leading to TGFβ mediated autoubiquitination of TRAF6 and subsequent activation of the TAK1-p38 pathway, which leads to apoptosis. [9] Moreover, the TRAF proteins act as adaptor proteins in transducing signals to various signaling partners. Suppression of TRAF6 expression via RNA silencing inhibited the endogenous interaction of TβRI and PS1, indicating that TRAF6 is required for their interaction. Moreover, the TβRI E161A mutant, which lacks the ability to bind to TRAF6, completely abolished the interaction between TβRI and PS1. In sum, the data disclosed herein show that TRAF6 plays a central role in regulating the interaction between TβRI and PS1 and thereby promoting cleavage of the TβRI.

In conclusion, the results disclosed in Example 2 demonstrate that (a) the TβRI is cleaved in its transmembrane domain by PS1, (b) TRAF6 plays a major role in the activation of PS1 by K63 linked polyubiquitination and mediates the cleavage of the TβRI by recruiting PS1, (c) the V129A/I130A mutant inhibits the cleavage of the TβRI, and (d) the TβRI ICD generated by the cleavage event translocates to the nuclei and binds to the TβRI promoter and regulates it expression.

References for Example 2

1. Massague, J., *TGFbeta in Cancer*. Cell, 2008. 134(2): p. 215-30.
2. Heldin, C. H., M. Landstrom, and A. Moustakas, *Mechanism of TGF-beta signaling to growth arrest, apoptosis, and epithelial-mesenchymal transition*. Curr Opin Cell Biol, 2009. 21(2): p. 166-76.
3. Wrana, J. L., et al., *Mechanism of activation of the TGF-beta receptor*. Nature, 1994. 370(6488): p. 341-7.
4. Souchelnytskyi, S., et al., *Phosphorylation of Ser465 and Ser467 in the C terminus of Smad2 mediates interaction with Smad4 and is required for transforming growth factor-beta signaling*. J Biol Chem, 1997. 272(44): p. 28107-15.
5. Abdollah, S., et al., *TbetaRI phosphorylation of Smad2 on Ser465 and Ser467 is required for Smad2-Smad4 complex formation and signaling*. J Biol Chem, 1997. 272(44): p. 27678-85.
6. Macias-Silva, M., et al., *MADR2 is a substrate of the TGFbeta receptor and its phosphorylation is required for nuclear accumulation and signaling*. Cell, 1996. 87(7): p. 1215-24.
7. Tsukazaki, T., et al., *SARA, a FYVE domain protein that recruits Smad2 to the TGFbeta receptor*. Cell, 1998. 95(6): p. 779-91.
8. Nakao, A., et al., *TGF-beta receptor-mediated signalling through Smad2, Smad3 and Smad4*. EMBO J, 1997. 16(17): p. 5353-62.
9. Sorrentino, A., et al., *The type I TGF-beta receptor engages TRAF6 to activate TAK1 in a receptor kinase-independent manner*. Nat Cell Biol, 2008. 10(10): p. 1199-207.
10. Thakur, N., et al., *TGF-beta uses the E3-ligase TRAF6 to turn on the kinase TAK1 to kill prostate cancer cells*. Future Oncol, 2009. 5(1): p. 1-3.
11. Landstrom, M., *The TAK1-TRAF6 signalling pathway*. Int J Biochem Cell Biol, 2010. 42(5): p. 585-9.

12. Bergmans, B. A. and B. De Strooper, *gamma-secretases: from cell biology to therapeutic strategies*. Lancet Neurol, 2010. 9(2): p. 215-26.
13. De Strooper, B., et al., *Deficiency of presenilin-1 inhibits the normal cleavage of amyloid precursor protein*. Nature, 1998. 391(6665): p. 387-90.
14. McCarthy, J. V., C. Twomey, and P. Wujek, *Presenilin-dependent regulated intramembrane proteolysis and gamma-secretase activity*. Cell Mol Life Sci, 2009. 66(9): p. 1534-55.
15. Thinakaran, G., et al., *Endoproteolysis of presenilin 1 and accumulation of processed derivatives in vivo*. Neuron, 1996. 17(1): p. 181-90.
16. Vetrivel, K. S., et al., *Pathological and physiological functions of presenilins*. Mol Neurodegener, 2006. 1: p. 4.
17. Brunkan, A. L. and A. M. Goate, *Presenilin function and gamma-secretase activity*. J Neurochem, 2005. 93(4): p. 769-92.
18. De Strooper, B., et al., *Phosphorylation, subcellular localization, and membrane orientation of the Alzheimer's disease-associated presenilins*. J Biol Chem, 1997. 272(6): p. 3590-8.
19. Laudon, H., et al., *A nine-transmembrane domain topology for presenilin 1*. J Biol Chem, 2005. 280(42): p. 35352-60.
20. Spasic, D., et al., *Presenilin-1 maintains a nine-transmembrane topology throughout the secretory pathway*. J Biol Chem, 2006. 281(36): p. 26569-77.
21. Wakabayashi, T. and B. De Strooper, *Presenilins: members of the gamma-secretase quartets, but part-time soloists too*. Physiology (Bethesda), 2008. 23: p. 194-204.
22. Liu, C., et al., *TACE-mediated ectodomain shedding of the type I TGF-beta receptor downregulates TGF-beta signaling*. Mol Cell, 2009. 35(1): p. 26-36.
23. Powell, J. C., et al., *Association between Presenilin-1 and TRAF6 modulates regulated intramembrane proteolysis of the p75NTR neurotrophin receptor*. J Neurochem, 2009. 108(1): p. 216-30.
24. Cao, Z., et al., *TRAF6 is a signal transducer for interleukin-1*. Nature, 1996. 383(6599): p. 443-6.

Example 3

Figure 24:
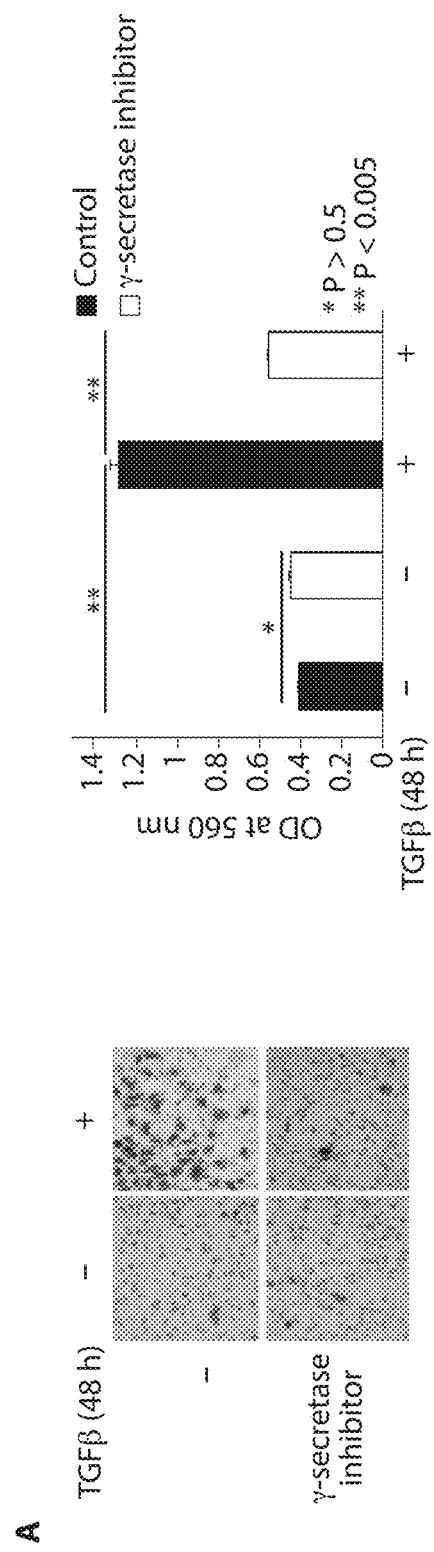
FIG. 24 shows suppression of TGFβ-induced cancer cell invation by of γ-secretase inhibitors. Panels A and B: photos/chart showing the invasion levels of PC-3U, human lung carcinoma cells (A549), and human breast carcinoma (MDA-MB-231) cells treated with TGFβ in the absence or presence of a γ-secretase inhibitor. Cells were visualized by staining with crystal violet cell stain solution. The right part and bottom parts of A and B present mean values for optical density (OD) of invasive cells. Error bars represents mean±s.d. (n=3 independent experiments; *P<0.05, **P<0.005, ANOVA).
Figure 24:
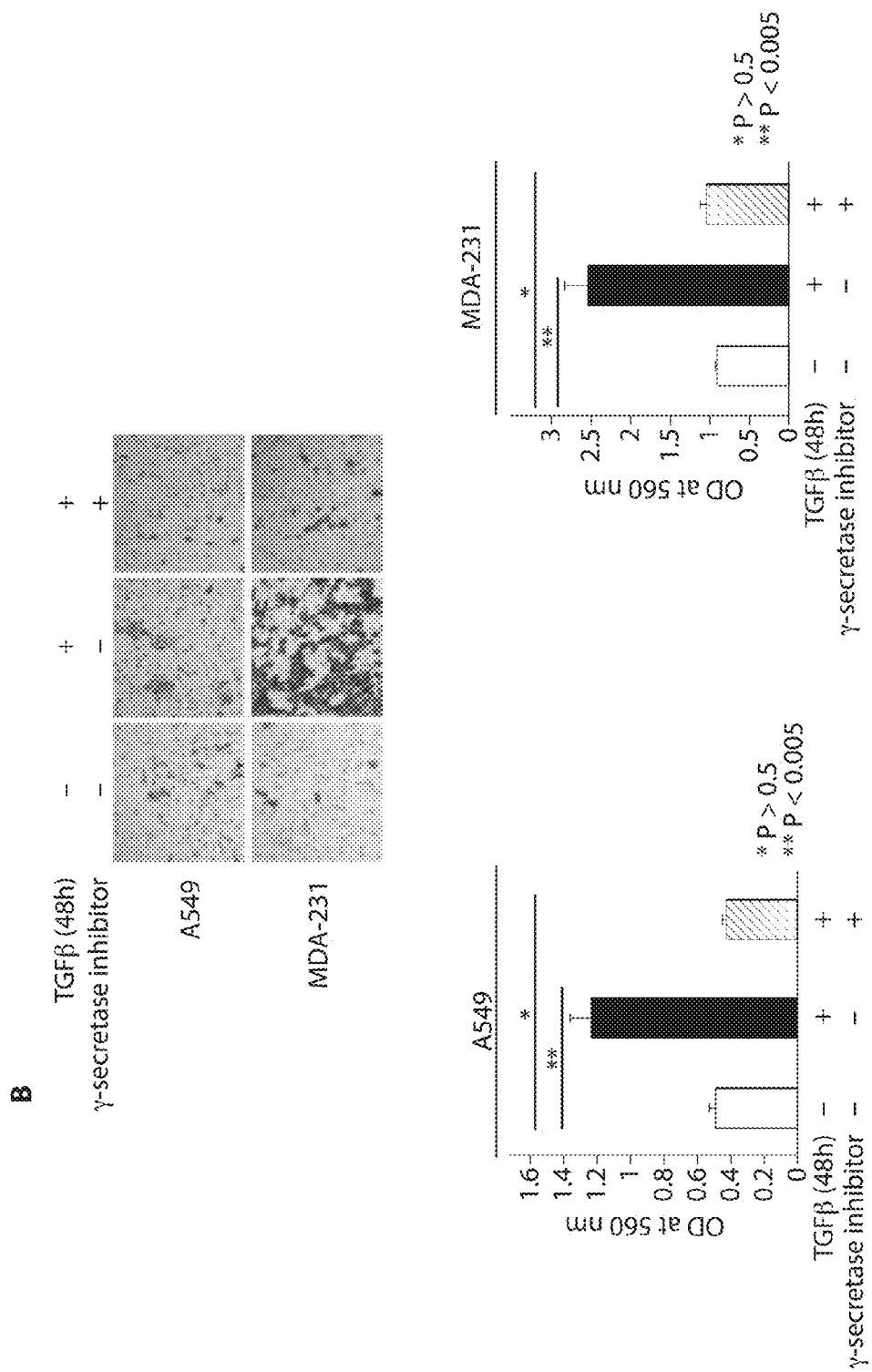

Inhibition of Cancer Cell Invasion Using γ-Secretase Inhibitors and Anti-TβRI Antibodies The cancer cell invasion assay described in Example 1 above was performed to examine the ability of γ-secretase inhibitors in suppressing cancel cell invasion. Prostate cancers cells PC-3U, human lung carcinoma cells A549, and human breast carcinoma cells MDA-MB-231 were cultured following routine procedures, treated with TGFβ in the presence of absence of L-685,458, a γ-secretase inhibitor. Cells were visualized by staining with a crystal violet cell staining solution. As shown in FIG. 24, the γ-secretase inhibitor significantly suppressed TGFβ-induced cancel cell invasion.

Next, polyclonal antibodies specific to amino acid residues 114-124 in the extracellular domain of TβRI (SEQ ID NO: 1) and polyclonal antibodies specific to amino acid residues 490-503 were generated in rabbit, following routine methods.

Figure 25:
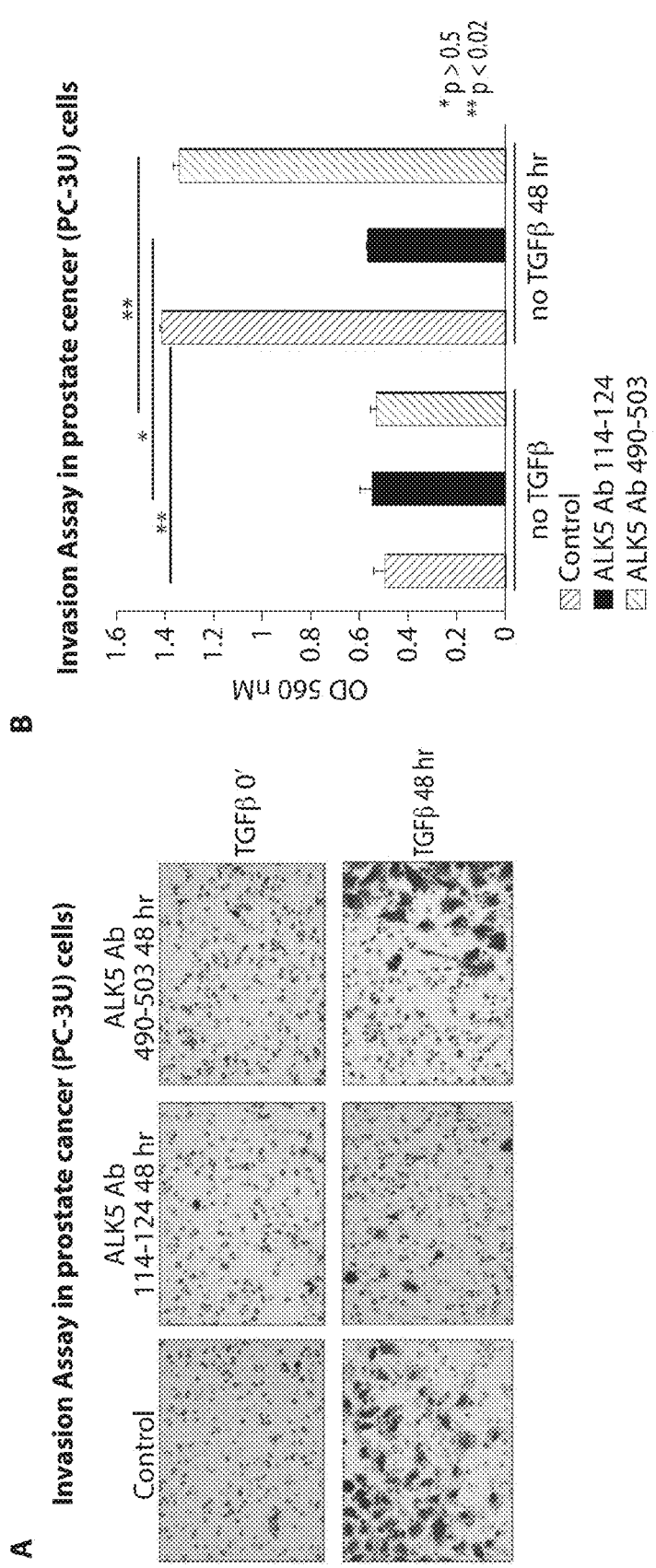
FIG. 25 shows inhibition of cancer cell invasion by antibodies specific to a TACE-cleavage site in TβRI, which encompass. Panel A: a photo showing invasion levels of PC-3U cells in the presence of ALK5 Ab 114-124 or ALK Ab 490-503. Control cells were not treated with antibodies. Cells were visualized by staining with crystal violet cell stain solution. Panel B: a chart presenting mean values for optical density (OD) of invasive cells. Data in the figure are representative of three independent experiments (mean and s.d). *P>0.5 and **P<0.02.

The ability of the above-noted polyclonal antibodies for inhibiting cancer cell invasion was examined by the invasion assay described in Example 1 above. Prostate cancer cells (PC-3U cells) were incubated in the presence of polyclonal antibodies specific to the 114-124 epitope (ALK5 Ab 114-124) or polyclonal antibodies specific to the 490-503 epitope (ALK5 Ab 490-503), or in the absence of antibodies. Cells were visualized by staining with crystal violet cell stain solution. As shown in FIG. 25, panels A and B, ALK5 Ab 114-124 significantly suppressed cancer invasion, while ALK5 Ab 490-503 did not exihibit this inhibitory effect.

Monoclonal antibodies are generated via standard hybridoma technology, using various epitopes of TβRI, such as epitope 114-124 and epitope 490-503. The inhibitory effects of these antibodies on cancer cell invasion are tested by the same invasion assay, using various cancer cell lines, e.g., breast cancer cells, lung cancer cells, prostate cancer cells, and colorectal cancer cells.

After the antibodies' inhibitory effects are confirmed, these antibodies are further analyzed in an animal cancer model such as a rat (Dunning) or mouse (TRAMP) prostate cancer model as described in Johansson et al., 2011, BJU Int. 107 (11):1818-1824 to confirm their activity in suppressing cancer cell invasion in vivo.

The monoclonal antibodies noted above can be modified to produce humanized antibodies by replacing the framework regions in non-human antibodies with the framework regions from a human antibody and retaining regions/residues responsible for antigen binding (e.g., the complementarity determining regions, particularly the specificity-determining residues therein). Methods to identify regions/residues in the heavy and light chains of an antibody are well known in the art. See, e.g., Almagro, J. Mol. Recognit. 17:132-143 (2004); and Chothia et al., J. Mol. Biol. 227:799-817 (1987).

Other Embodiments

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

What is claimed is:

1. An isolated antibody that binds to a type I receptor of transforming growth factor beta (TβRI) and blocks its cleavage to release an intracellular domain (ICD) of the TβRI, thereby blocking the ICD from translocating to the nucleus of the cell, wherein the antibody binds to an epitope within residues 114-124 in SEQ ID NO:1.

2. The isolated antibody of claim 1, wherein the antibody is a humanized antibody or a human antibody.

3. The isolated antibody of claim 1, wherein the antibody is a bispecific antibody that:

(i) binds to both the TβRI and TACE, (ii) binds to both the TβRI and PS1, or (iii) binds to both the TβRI and MMP14.

4. A method for inhibiting cleavage of a type I receptor of transforming growth factor beta (TβRI), the method comprising contacting a cell with a TβRI cleavage inhibitor in an amount sufficient to inhibit cleavage of a TβRI to release an intracellular domain (ICD) of the TβRI, thereby blocking the ICD from translocating to the nucleus of the cell, wherein the cleavage inhibitor is an antibody that binds to an epitope within residues 114-124 in SEQ ID NO:1.

5. The method of claim 4, wherein the antibody is a bispecific antibody that:

(i) binds to both TβRI and TACE, (ii) binds to both the TβRI and PS1, or (iii) binds to both the TβRI and MMP14.

6. The method of claim 4, wherein the cell is a cancer cell.

7. The method of claim 6, wherein the contacting step is performed by administering the TβRI cleavage inhibitor to a patient carrying the cancer cell.

8. A method for reducing invasiveness of cancer cells in a subject, comprising administering to a subject carrying cancer cells a pharmaceutical composition comprising a TβRI cleavage inhibitor in an amount sufficient to inhibit cleavage of a TβRI to release an intracellular domain (ICD) of the TβRI, thereby blocking the ICD from translocating to the nuclei of the cancer cells and reducing their invasiveness, wherein the cleavage inhibitor is an antibody that binds to an epitope within residues 114-124 in SEQ ID NO:1.

9. The method of claim 8, wherein the antibody is a bispecific antibody that:

(iv) binds to both TβRI and TACE, (v) binds to both the TβRI and PS1, or (vi) binds to both the TβRI and MMP14.

10. The method of claim 8, wherein the amount of the TβRI cleavage inhibitor is sufficient to reduce cancer metastasis in a human cancer patient.

* * * * *